(12) United States Patent
Morgenstern

(10) Patent No.: US 11,465,960 B2
(45) Date of Patent: Oct. 11, 2022

(54) LABILE ESTERS OF AGROCHEMICALS FOR CONTROLLED RELEASE AND REDUCTION OF OFF-SITE MOVEMENT

(71) Applicant: Monsanto Technology LLC, St. Louis, MO (US)

(72) Inventor: David A. Morgenstern, Creve Coeur, MO (US)

(73) Assignee: Monsanto Technology LLC, St. Louis, MO (US)

(*) Notice: Subject to any disclaimer, the term of this patent is extended or adjusted under 35 U.S.C. 154(b) by 66 days.

(21) Appl. No.: 17/008,880

(22) Filed: Sep. 1, 2020

(65) Prior Publication Data

US 2020/0392063 A1     Dec. 17, 2020

Related U.S. Application Data

(62) Division of application No. 15/225,396, filed on Aug. 1, 2016, now abandoned, and a division of application No. 15/913,030, filed on Mar. 6, 2018, now Pat. No. 10,793,503, which is a division of application No. 15/225,396, filed on Aug. 1, 2016, now abandoned, (Continued)

(51) Int. Cl.

| | | |
|---|---|---|
| A01N 37/40 | (2006.01) | |
| A01N 37/38 | (2006.01) | |
| A01N 39/04 | (2006.01) | |
| A01N 43/40 | (2006.01) | |
| A01N 43/58 | (2006.01) | |
| A01N 43/60 | (2006.01) | |
| C07D 213/64 | (2006.01) | |
| C07D 237/32 | (2006.01) | |
| C07C 65/21 | (2006.01) | |
| C07C 205/34 | (2006.01) | |
| C07C 205/37 | (2006.01) | |
| C07C 205/42 | (2006.01) | |
| C07C 255/55 | (2006.01) | |
| C07C 205/43 | (2006.01) | |
| C07C 205/56 | (2006.01) | |
| C07C 69/712 | (2006.01) | |
| C07C 69/92 | (2006.01) | |
| A01N 43/42 | (2006.01) | |
| C07D 213/84 | (2006.01) | |
| C07D 215/32 | (2006.01) | |
| C07D 237/16 | (2006.01) | |
| C07D 241/18 | (2006.01) | |
| C07D 213/63 | (2006.01) | |
| C07D 213/69 | (2006.01) | |
| A01N 43/16 | (2006.01) | |
| C07D 213/85 | (2006.01) | |
| C07D 241/44 | (2006.01) | |
| C07D 237/26 | (2006.01) | |

(52) U.S. Cl.
CPC .............. *C07C 65/21* (2013.01); *A01N 37/38* (2013.01); *A01N 37/40* (2013.01); *A01N 39/04* (2013.01); *A01N 43/16* (2013.01); *A01N 43/40* (2013.01); *A01N 43/42* (2013.01); *A01N 43/58* (2013.01); *A01N 43/60* (2013.01); *C07C 69/712* (2013.01); *C07C 69/92* (2013.01); *C07C 205/34* (2013.01); *C07C 205/37* (2013.01); *C07C 205/42* (2013.01); *C07C 205/43* (2013.01); *C07C 205/56* (2013.01); *C07C 255/55* (2013.01); *C07D 213/63* (2013.01); *C07D 213/64* (2013.01); *C07D 213/69* (2013.01); *C07D 213/84* (2013.01); *C07D 213/85* (2013.01); *C07D 215/32* (2013.01); *C07D 237/16* (2013.01); *C07D 237/26* (2013.01); *C07D 237/32* (2013.01); *C07D 241/18* (2013.01); *C07D 241/44* (2013.01); *Y02P 20/55* (2015.11); *Y02P 20/582* (2015.11)

(58) Field of Classification Search
CPC ........ A01N 37/38; A01N 37/40; A01N 39/04; A01N 43/40; A01N 43/42; A01N 43/58; A01N 43/60; C07D 213/64; C07D 237/32
See application file for complete search history.

(56) References Cited

U.S. PATENT DOCUMENTS 5,462,915 A    10/1995   Curtis et al.
5,908,632 A     6/1999   Nastke et al.
(Continued)

FOREIGN PATENT DOCUMENTS

CN      1552695 A    12/2004
CN      1743304 A     3/2006
(Continued)

OTHER PUBLICATIONS

U.S. Appl. No. 15/913,030.
(Continued)

*Primary Examiner* — Abigail Vanhorn
(74) *Attorney, Agent, or Firm* — Harness, Dickey & Pierce, P.L.C.

(57) ABSTRACT

The present invention relates to esters of carboxylic acid agrochemicals comprising a labile protecting group and having formula (I). Certain of the esters of carboxylic acid agrochemicals do not undergo hydrolysis to a significant degree in the dark, but are cleaved to regenerate the parent carboxylic acid agrochemical when exposed to light. Others of the esters of carboxylic acid agrochemicals undergo hydrolysis under both light and dark conditions. The present invention further relates to methods for the controlled release of a carboxylic acid agrochemicals, and to methods of controlling unwanted plants comprising applying to the unwanted plants an ester of a carboxylic acid agrochemical.

21 Claims, 2 Drawing Sheets

Related U.S. Application Data which is a division of application No. 14/351,209, filed as application No. PCT/US2012/059792 on Oct. 11, 2012, now Pat. No. 9,402,396.

(60) Provisional application No. 61/545,731, filed on Oct. 11, 2011.

(56) References Cited

U.S. PATENT DOCUMENTS

| 6,890,888 B2 | 5/2005 | Pursell et al. |
| 2010/0184756 A1 | 7/2010 | Suzuki et al. |

FOREIGN PATENT DOCUMENTS

| FR | 1 375 311 | 10/1964 |
| JP | 49007215 B | 2/1974 |
| JP | 54135734 A | 10/1979 |
| NL | 6404312 A | 10/1965 |
| WO | 03/000644 A1 | 1/2003 |

OTHER PUBLICATIONS

U.S. Appl. No. 15/225,396.
U.S. Appl. No. 14/351,209.
Atta, S., et al., "Fluorescent Caged Compounds of 2,4-Dichlorophenoxyacetic Acid (2,4-D): Photorelease Technology for Controlled Release of 2,4-D," Journal of Agricultural and Food Chemistry, Nov. 2010, pp. 11844-11851, vol. 58, No. 22.
Banerjee, A., et al., "Protecting Groups That Can Be Removed Through Photochemical Electron Transfer: Mechanistic and Product Studies on Photosensitized Release of Carboxylates From Phenacyl Esters," The Journal of Organic Chemistry, 1997, pp. 6245-6251, vol. 62, No. 18.
Bellus, D., et al., "Photochemical Rearrangement of Aryl, Vinyl, and Substituted Vinyl Esters and Amides of Carboxylic Acids," Chemical Reviews, Nov. 24, 1967, pp. 599-609, vol. 67, No. 6.
Bochet, C. G., "Photolabile Protecting Groups and Linkers," Journal of the Chemical Society, Perkin Transactions 1, 2002, pp. 125-142.
Bollich, P. K., et al., "Rice (*Oryza sativa*) Response to the Microencapsulated Formulation of Clomazone," Weed Technology, 2000, pp. 89-93, vol. 14.
Givens, R. S., et al., "New Photoactivated Protecting Groups. 7. p-Hydroxyphenacyl: A Phototrigger for Excitatory Amino Acids and Peptides," Journal of the American Chemical Society, 1997, pp. 8369-8370, vol. 119, No. 35.
Givens, R. S., et al., "The Photo-Favorskii Reaction of p-Hydroxyphenacyl Compounds is Initiated by Water-Assisted, Adiabatic Extrusion of A Triplet Biradical," Journal of the American Chemical Society, 2008, pp. 3307-3309, vol. 130, No. 11.
Hasan, A., et al., "Photolabile Protecting Groups for Nuclesides: Synthesis and Photodeprotection Rates," Tetrahedron, 1997, pp. 4247-4264, vol. 53, No. 12.
International Search Report and Written Opinion issued for PCT/US2012/059792 dated Jun. 6, 2013, 21 pages.
Invitation to Pay Additional Fees and,Where Applicable, Protest Fee issued for PCT/US2012/059792 dated Mar. 1, 2013, 12 pages.
Kenawy, E.-R., et al., "Controlled Release of Polymer Conjugated Agrochemicals. System Based on Poly(Methyl Vinyl Ether-alt-Maleic Anhydride)," Journal of Applied Polymer Science, 2001, pp. 415-421, vol. 80.
Miranda, M. A., et al., "The Photo-Fries Rearrangement," Chapter 2, Molecular and Supramolecular Photochemistry, 2003, pp. 43-131.
Newman, M. S., et al., "New Compounds as Plant Growth Regulators," Journal of the American Chemical Society, Mar. 1947, pp. 718-723, vol. 69, No. 3.
Pasapera A., M., "Preparation of The Herbicide 2,4-D and Derivatives," Anales de la Facultad de Farmacia y Bioquimica (1950-1957), 1952, pp. 437-448, vol. 3 (Abstract only).
Patchornik, A., et al., "Photosensitive Protecting Groups," Journal of the American Chemical Society, Communications to the Editor, Oct. 1970, pp. 6333-6335, vol. 92, No. 21.
Pelliccioli, A. P., et al., "Photoremovable Protecting Groups: Reaction Mechanisms and Applications," Photochemical & Photobiological Sciences, Jul. 2002, pp. 441-458, vol. 1, No. 7.
Reichmanis, E., et al., "o-Nitrobenzyl Photochemistry: Solution vs. Solid-State Behavior," Journal of Polymer Science: Polymer Chemistry Edition, Jan. 1985, pp. 1-8, vol. 23, No. 1.
Senseman, S. A., Editor, Herbicide Handbook, Ninth Edition, 2007, pp. 25-31, 141-142, and 322-328, Weed Science Society of America.
Sheehan, J. C., et al., "Phenacyl Photosensitive Blocking Groups," The Journal of Organic Chemistry, 1973, pp. 3771-3774, vol. 38, No. 21.
Wagner, C. R., et al., "Some New Esters of 2,4-dichlorophenoxyacetic Acid and Their Herbicidal Activity," Journal of the American Chemical Society, 1953, pp. 4861-4862, vol. 75 (Abstract only).
Wang, P., et al., "Novel Photolabile Protecting Group for Carbonyl Compounds," Organic Letters, 2007, Pages A-C, vol. 0, No. 0.
Pillai, V.N. et al., Photoremovable Protecting Groups in Organic Synthesis, Synthesis (1980), pp. 1-26.
Flint, J.L. et al., Effects of Glyphosate Combinations with 2,4-D or Dicamba on Field Bindweed (*Convolvulus arvensis*). Weed Science (1989) vol. 37, pp. 12-18.
Yang, G-q., et al., "Synthesis and Bioactivity of (aryloxy)phenoxypropionate Compounds Containing a,Beta Unsaturated Carboxylates," 2010, Modern Agrochemicals, 9/6:9-14, 6 pages.

LABILE ESTERS OF AGROCHEMICALS FOR CONTROLLED RELEASE AND REDUCTION OF OFF-SITE MOVEMENT

CROSS-REFERENCES TO RELATED APPLICATIONS

This application is a divisional of U.S. patent application Ser. No. 15/913,030, filed on Mar. 6, 2018, which is a divisional of U.S. patent application Ser. No. 15/225,396, filed on Aug. 1, 2016, now abandoned, which is a divisional of U.S. patent application Ser. No. 14/351,209, filed on Apr. 11, 2014, now issued as U.S. Pat. No. 9,402,396, which is a U.S. National of PCT Application No. PCT/US2012/059792, filed Oct. 11, 2012, which claims the benefit of U.S. Provisional Patent Application No. 61/545,731, filed on Oct. 11, 2011. Each of the above-cited applications is incorporated herein by reference in its entirety.

FIELD OF THE INVENTION

The present invention relates to the field of agrochemistry, and more particularly to esters of carboxylic acid agrochemicals comprising a labile protecting group. The present invention further relates to methods for the controlled release of a carboxylic acid agrochemicals, and to methods of controlling unwanted plants comprising applying to the unwanted plants an ester of a carboxylic acid agrochemical.

BACKGROUND OF THE INVENTION

Agrochemicals are typically applied either as a solution or as a suspension of a fine powder. It is often desirable for the agrochemical to remain either near the surface of the soil (in the case of many insecticides and pre-emergent herbicides, for example) or within the root zone for active agents that are taken up through the roots, such as fertilizers and certain herbicides. However, in many cases, agrochemicals are rapidly depleted from the soil zone in which they are most effective. Among the mechanisms of depletion are metabolism by bacteria, surface runoff and wash-down deep into the soil by rain, and volatilization. Such depletion leads to a loss of efficacy, and can also result in contamination of surface and groundwater.

One approach to extending residual activity and reducing the offsite movement of an agrochemical involves impregnating the agrochemical into an inert matrix. Under favorable conditions, controlled release of the agrochemical can take place. For example, U.S. Pat. No. 6,890,888 describes impregnating urea and other fertilizers into expanded perlite, which can be soil-applied to achieve controlled release. Agrochemicals can also be impregnated into clays or polymer particles, as described, for example, in U.S. Pat. No. 5,908,632 and the references cited therein. Alternatively, an agrochemical can be chemically linked to a polymer. For example, Kenawy et al. (*J. Appl. Polymer Sci.* 80: 415-21 (2001)) describes linking 2,4-dichlorophenoxyacetic acid (2,4-D) to a polymer backbone via an amide linkage.

For herbicides that can cause crop injury at high rate, micro-encapsulation can reduce crop injury by providing controlled release while reducing off-site movement. For example, Bollich et al. (*Weed Technology* 14:89-93 (2000)) describes micro-encapsulation of clomazone. Several commercial microencapsulated herbicides are also available, for example, the COMMAND® (FMC Corp, clomazone) and WARRANT® (Monsanto, acetochlor) products.

Achieving controlled release is particularly challenging for agrochemicals that contain carboxylic acid groups. Such agrochemicals are referred to herein as "carboxylic acid agrochemicals." Carboxylic acid agrochemicals exist in the form of salts or zwitterions when released in the field, rendering them water soluble. Waterborne movement of agrochemicals containing carboxylic acid groups is therefore facile. In addition, the water solubility of these compounds leads to rapid leaching from matrices which can be used for controlled release of other molecules and complicates formation of microcapsules, a process which is typically conducted in a 2-phase, water-organic mixture with the active in the organic phase.

Alkyl esters of carboxylic acid agrochemicals exhibit reduced water solubility. For example, as described in the *Herbicide Handbook* ($9^{th}$ ed., 2007), the methyl ester of diclofop, the ethyl esters of fenoxaprop-P and desmedipham, and the butyl ester of cyhalofop along with many alkyl esters of 2,4-D are used as herbicides. However, alkyl esters of certain carboxylic acid agrochemicals hydrolyze rapidly in the soil, rendering them more susceptible to microbial degradation. As a result, alkyl esters of such carboxylic acid agrochemicals seldom if ever have significant residual activity. On the other hand, hindered aromatic esters previously known in the art typically hydrolyze far too slowly and are not practical for controlled release of agrochemicals.

Thus, there exists a need in the art for a method of achieving controlled release of carboxylic acid agrochemicals. This need is particularly acute for molecules which can cause damage to crops in neighboring fields by volatilization, for example, the auxin-mimic herbicides dicamba and 2,4-D.

SUMMARY OF THE INVENTION

The present invention is directed to esters of a carboxylic acid agrochemicals comprising a photolabile or hydrolytically labile protecting group and having the formula (I):

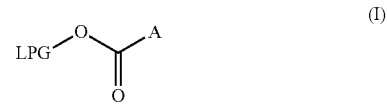

(I)

In formula (I), LPG is the labile protecting group, and the carboxylic acid agrochemical has the formula (II):

(II)

wherein A represents the remainder of the carboxylic acid agrochemical bonded to the carboxylic acid moiety.

In various embodiments, the ester of a carboxylic acid agrochemical has a photolabile group that comprises a nitrophenyl moiety. For example, in some embodiments, the ester of a carboxylic acid agrochemical has the formula (III):

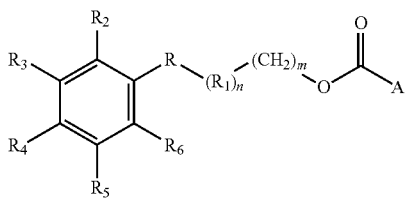

wherein R is C(R$_7$R$_8$), O, or S;
R$_1$ is C(R$_9$R$_{10}$), O, or S;
provided that when R is O or S, R$_1$ must be C(R$_9$R$_{10}$), and when R$_1$ is O or S, R must be C(R$_7$R$_8$);
R$_7$, R$_8$, R$_9$, and R$_{10}$ are independently H, CH$_3$, or CH$_2$CH$_3$;
at least one of R$_2$ and R$_3$ is NO$_2$ and the other is H, acyclic aliphatic, amine, NO$_2$ or alkoxy; R$_4$ is H, alkoxy, acyclic aliphatic, amine, NO$_2$, or an ester having the formula (IV):

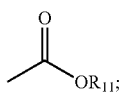

wherein R$_{11}$ is C$_1$-C$_{18}$ acyclic aliphatic;
R$_5$ and R$_6$ are independently H, alkoxy, acyclic aliphatic, amine, or NO$_2$;
provided that if any of R$_2$, R$_3$, R$_4$, R$_5$ and R$_6$ is acyclic aliphatic, the acyclic aliphatic does not comprise a double or triple bond between the α and β carbons;
n is 0 or 1; and
m is 0-3, provided that if R is O and n is 0, m is at least 1.

In other embodiments, the ester of a carboxylic acid agrochemical has a photolabile group that comprises a phenacylmethyl ester moiety. In some such embodiments, the ester of a carboxylic acid agrochemical has the formula (V):

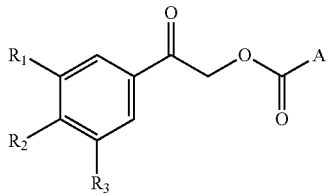

wherein R$_2$ is hydroxy, alkoxy, or substituted alkoxy; and R$_1$ and R$_3$ are independently H, hydroxy, alkoxy, substituted alkoxy, or C$_1$-C$_{18}$ unsubstituted or substituted acyclic aliphatic, provided that if either of R$_1$ and R$_3$ is C$_1$-C$_{18}$ unsubstituted or substituted acyclic aliphatic, the acyclic aliphatic does not comprise a double or triple bond between the α and β carbons.

In yet other embodiments, the ester of a carboxylic acid agrochemical has the formula (VI):

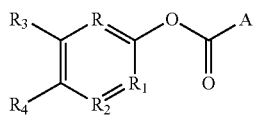

wherein at least one of R and R$_1$ is N, and the other of R and R$_1$ is N or C—R$_5$;
R$_2$ is N or CH;
R$_3$ and R$_4$ are H, acyclic alkyl, substituted acyclic alkyl, or together form a phenyl ring;
and R$_5$ is H, acyclic alkyl, or substituted acyclic alkyl.

In still other embodiments, the ester of a carboxylic acid agrochemical has the formula (VII):

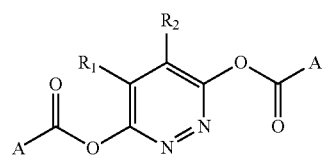

wherein R$_1$ and R$_2$ are independently H or C$_1$-C$_8$ alkyl, or together form a phenyl ring.

In various other embodiments, the ester of a carboxylic acid agrochemical has the formula (VIII):

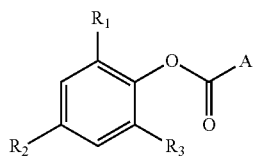

wherein R$_1$, R$_2$, and R$_3$ are alkyl.

Moreover, in some embodiments, the ester of a carboxylic acid agrochemical has the formula (IX):

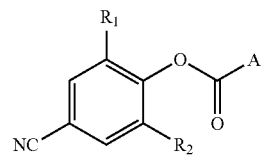

wherein R$_1$ and R$_2$ are halogen.

In other embodiments, the ester of a carboxylic acid agrochemical has the formula (X):

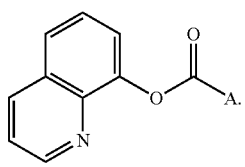

In yet other embodiments, the ester of a carboxylic acid agrochemical has the formula (XI):

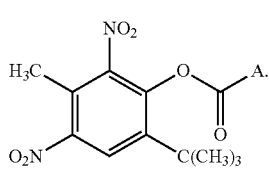

In other embodiments, the ester of a carboxylic acid agrochemical has the formula (XII):

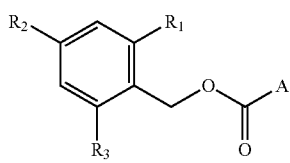

wherein at least one of $R_1$, $R_2$, and $R_3$ is an electron-donating group;
and the others of $R_1$, $R_2$, and $R_3$ are independently H or an electron-donating group;
provided that none of $R_1$, $R_2$, and $R_3$ is an electron-withdrawing group.

In still other embodiments, the ester of a carboxylic acid agrochemical has the formula (XIII):

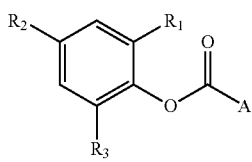

wherein at least one of $R_1$, $R_2$, and $R_3$ is an electron-donating group;
and the others of $R_1$, $R_2$, and $R_3$ are independently H or an electron-donating group;
provided that none of $R_1$, $R_2$, and $R_3$ is an electron-withdrawing group.

In other embodiments, the ester of a carboxylic acid agrochemical has the formula (XIV):

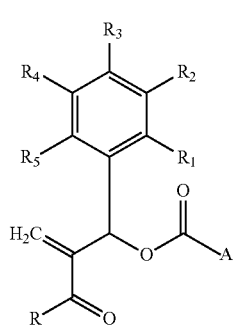

wherein R is alkyl, aryl, or alkoxy;
at least one of $R_1$, $R_2$, $R_3$, $R_4$, and $R_5$ is an electron-withdrawing group;
and the others of $R_1$, $R_2$, $R_3$, $R_4$, and $R_5$ are independently H, alkyl, alkoxy, dialkylamino, or halogen.

In further embodiments, the ester of a carboxylic acid agrochemical has the formula (XV):

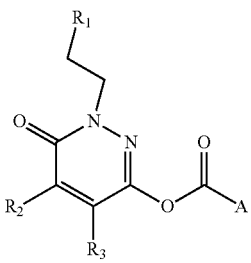

wherein $R_1$ is an electron-withdrawing group;
and wherein $R_2$ and $R_3$ are independently H or alkyl.

In still further embodiments, the ester of a carboxylic acid agrochemical has the formula (XVI):

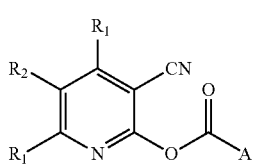

wherein $R_1$ is alkyl and $R_2$ is H, alkyl, or aryl.

In yet other embodiments, the ester of a carboxylic acid agrochemical has the formula (XVII):

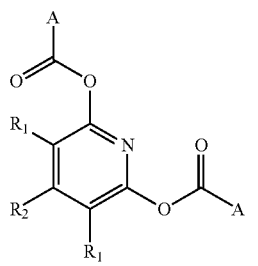

wherein $R_1$ is an electron-withdrawing group;
and $R_2$ is H, a hydrocarbon, or an aromatic group.

In addition, in various embodiments, the ester of a carboxylic acid agrochemical is a substituted or unsubstituted aromatic ester of dicamba or 2,4-dichlorophenoxyacetic acid (2,4-D).

The present invention is further directed to agrochemical compositions comprising any of the esters of carboxylic acid agrochemicals described herein.

The present invention is also directed to methods for the use of the esters of carboxylic acid agrochemicals. In some embodiments, the present invention is directed to methods for the controlled release of a carboxylic acid agrochemical. Some such methods comprise exposing an ester of a carboxylic acid agrochemical as described herein to artificial or natural light. Other of these methods comprise exposing an ester of a carboxylic acid agrochemical as described herein to aqueous conditions.

In other embodiments, the present invention is directed to a method of controlling unwanted plants. Such methods comprise applying to the unwanted plants an ester of a carboxylic acid agrochemical as described herein.

In yet other embodiments, the invention relates to a method for the controlled release of a compound comprising exposing the compound to natural or artificial light or exposing the compound to aqueous conditions, wherein the compound has been chemically modified to have an ester linkage to a labile protecting group having one of the following structures:

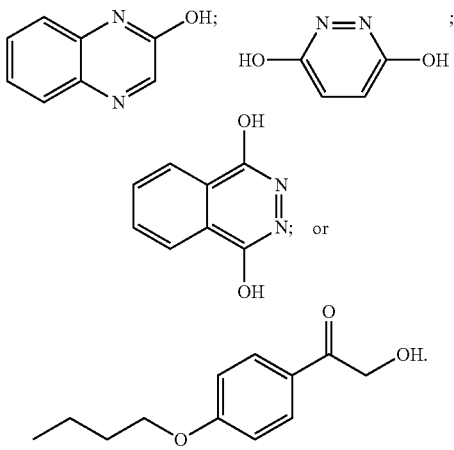

DETAILED DESCRIPTION OF THE PREFERRED EMBODIMENTS

Figure 1:
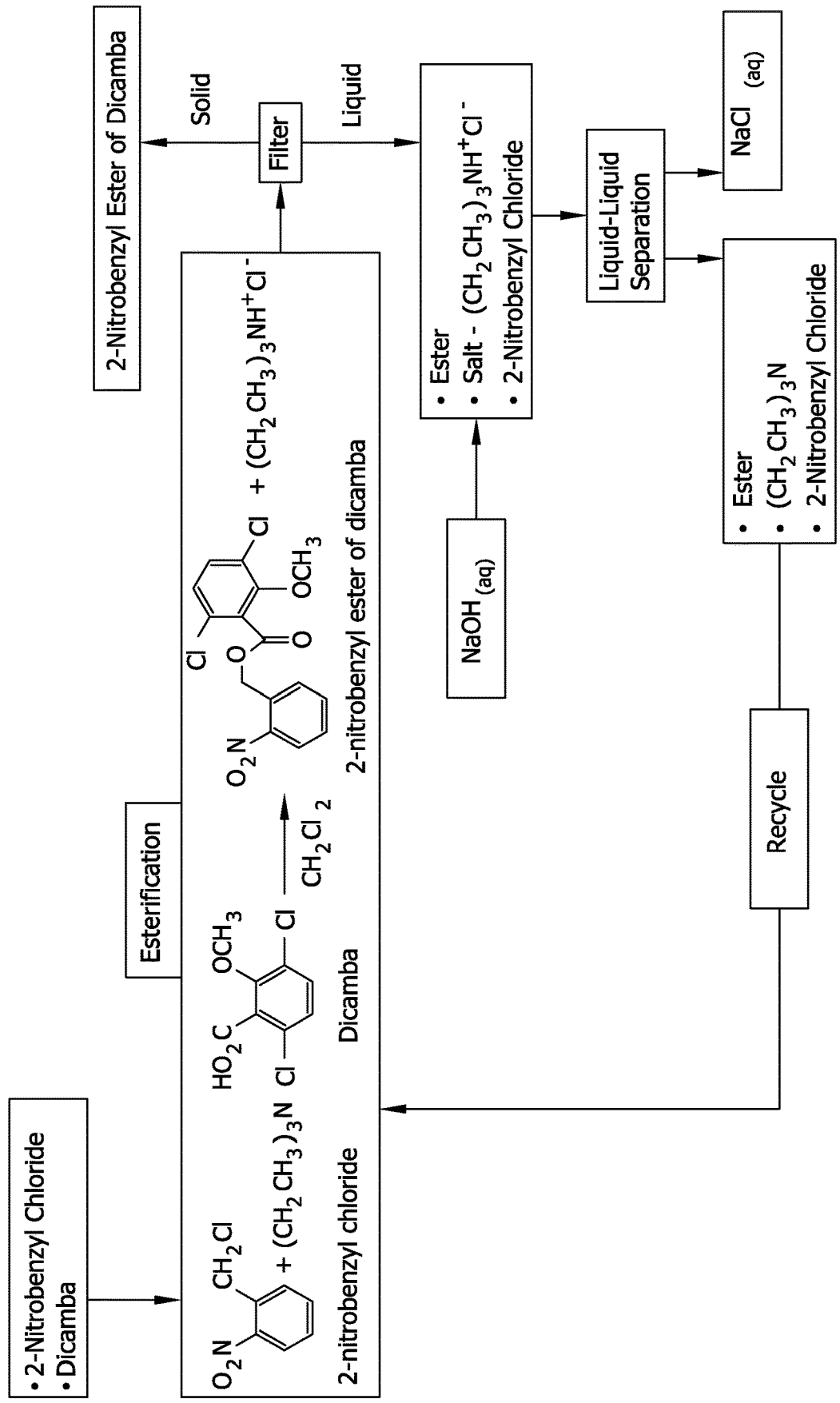
FIG. 1 is a schematic diagram showing a process for the preparation of 2-nitrobenzyl esters of carboxylic acid agrochemicals.

It has now been discovered that certain esters of carboxylic acid agrochemicals do not undergo hydrolysis to a significant degree in the dark, but are cleaved to regenerate the parent carboxylic acid compound when exposed to light. Such esters of carboxylic acid agrochemicals are of value for reducing volatility, off-site movement, and aqueous solubility of the agrochemical. Reducing the aqueous solubility improves residual activity by reducing washoff and washdown into the soil and facilitating controlled release technologies such as suspension concentrates and micro-encapsulation.

It has additionally been discovered that certain esters of carboxylic acid agrochemicals undergo conversion to the agronomically active acid by hydrolysis under typical agronomic conditions, while still others undergo both hydrolysis and photolysis.

Described herein are esters of carboxylic acid agrochemicals comprising a photolabile or hydrolytically labile protecting group having the formula (I):

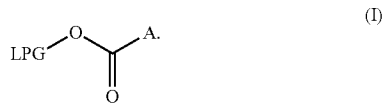

In formula (I), LPG represents the labile protecting group, and the carboxylic acid agrochemical has the formula (II):

wherein A represents the remainder of the carboxylic acid agrochemical bonded to the carboxylic acid moiety. Some of these esters of carboxylic acid agrochemicals undergo photo-induced cleavage substantially to a carboxylic acid agrochemical of formula (II) when exposed to natural or artificial light. Others of these esters undergo hydrolytic conversion substantially to a carboxylic acid agrochemical of formula (II) when exposed to moisture in the environment. These hydrolytically labile esters are suitably formulated as an emulsifiable concentrates in non-aqueous organic solvents in order to prevent premature hydrolysis.

The photolabile protecting groups of the esters of carboxylic acid agrochemicals described herein contain an aromatic moiety. The aromatic moiety is typically somewhat hindered to prevent rapid hydrolysis of the ester in the absence of light. These esters are stable to hydrolysis so long as they are not exposed to high levels of light during storage, but convert to the agronomically active compound when exposed to natural or artificial light, for example when exposed to sunlight following application of an agrochemical formulation containing the ester to a field (e.g., by spraying). Esters of formulas (III), (V), (VI) (VIII), (IX), (X), (XI), (XIII), (XIV), and (XV) undergo photolysis.

Esters of aromatic carboxylic acid agrochemicals, such as dicamba, are typically resistant to hydrolysis under typical agronomic conditions. However, esters of carboxylic acid agrochemicals of formulas (VI), (VII), (XII), (XIV), (XV), (XVI), and (XVII) undergo hydrolysis at typical agronomic temperatures at rates (days to weeks) which provide good activity while reducing offsite movement. The esters of formulas (VI), (XIV), and (XV) undergo both hydrolysis and photolysis.

Carboxylic Acid Agrochemicals

Generally, any agrochemical that contains a carboxylic acid moiety can be esterified to form the labile esters described herein. Thus, many different types of agrochemicals can be esterified to form the labile esters. For example, the agrochemical can be a herbicide, a fungicide, an insecticide, a plant health agent, or a plant growth regulator. Other types of agrochemicals can also be used to form the labile esters, so long as the agrochemical has a carboxylic acid moiety.

In various embodiments, the carboxylic acid agrochemical is an auxin-mimic herbicide such as dicamba or 2,4-dichlorophenoxyacetic acid (2,4-D). For example, in certain embodiments of the present invention, the ester of a carboxylic acid agrochemical is a substituted or unsubstituted aromatic ester of dicamba or 2,4-D.

Suitable herbicides also include, but are not limited to fenoxaprop, fenoxaprop-P, desmedipham, cyhalofop, carfentrazone, flufenpyr, fluthiacet, fluroglycofen, pyraflufen, flumiclorac, 4-(4-chloro-2-methylphenoxy)butanoic acid (MCPB), fluroxypyr, picloram, quinclorac, benazolin, clodinafop, 4-(2,4-dichlorophenoxy)butanoic acid (2,4-DB), 2,4,5-trichlorophenoxyacetic acid (2,4,5-T), dichlorprop, dichlorprop-P, diethatyl, endothall, fluazifop, flufenpyr, flumiclorac, fluoroglycofen, haloxyfop, indole-3-acetic acid, indole-3-butyric acid, mecoprop, mecoprop-P, pyrafluren, fenoprop, triclopyr, aminopyralid, bispyribac, chlorthal, imazamethabenz, pyrothiobac, quinmerac, quizalofop, quizalofop-P, diclofop, and lactofen. The structure of lactofen includes an ethyl ester which is hydrolyzed rapidly in situ to form the active form of the herbicide. The term "lactofen" as used herein refers to the active form of the herbicide, which includes a carboxylic acid moiety.

Suitable fungicides include, but are not limited to, benalaxyl and picoxystrobin. The terms "benalaxyl" and "picoxystrobin" are used in the art to refer to both the active forms of the compounds, which include carboxylic acid moieties, and to the methyl esters of the compounds. As used herein, the terms "benalaxyl" and "picoxystrobin" refer to the active forms of the compounds.

Suitable plant health agents include, but are not limited to, salicylic acid and 3,6-dichlorosalicylic acid. Suitable plant growth regulators include, but are not limited to cloprop and 4-chlorophenoxyacetic acid (4-CPA).

Typically, the labile esters are esters of agrochemicals that contain an aromatic carboxylic acid (e.g., dicamba). Aromatic carboxylic acids are more resistant to hydrolysis, thus providing better control of the release rate.

Although the following description of the labile esters and their synthesis, formulation, and use focuses on esters of dicamba and 2,4-D, the person having ordinary skill in the art will recognize that the same principles and methodology are applicable to other carboxylic acid agrochemicals.

Esters of Carboxylic Acid Agrochemicals Comprising a Labile Protecting Group

A. Nitrophenyl Esters

Several classes of esters of carboxylic acid agrochemicals have been found to undergo photo-induced cleavage to form the agronomically active carboxylic acid agrochemical when exposed to natural or artificial light. The first of these classes are the nitrophenyl esters. In the nitrophenyl esters, the photolabile protecting group of the ester of a carboxylic acid agrochemical comprises a nitrophenyl moiety. These nitrophenyl esters of carboxylic acid agrochemicals typically have the formula (III):

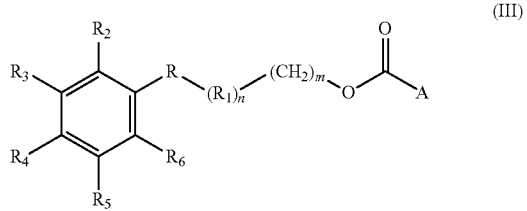

(III)

wherein

R is $C(R_7R_8)$, O, or S;

$R_1$ is $C(R_9R_{10})$, O, or S;

provided that when R is O or S, $R_1$ must be $C(R_9R_{10})$, and when $R_1$ is O or S, R must be $C(R_7R_8)$;

$R_7$, $R_8$, $R_9$, and $R_{10}$ are independently H, $CH_3$, or $CH_2CH_3$;

at least one of $R_2$ and $R_3$ is $NO_2$ and the other is H, acyclic aliphatic, amine, $NO_2$ or alkoxy;

$R_4$ is H, alkoxy, acyclic aliphatic, amine, $NO_2$, or an ester having the formula (IV):

(IV)

wherein $R_{11}$ is $C_1$-$C_{18}$ acyclic aliphatic;

$R_5$ and $R_6$ are independently H, alkoxy, acyclic aliphatic, amine, or $NO_2$;

provided that if any of $R_2$, $R_3$, $R_4$, $R_5$ and $R_6$ is acyclic aliphatic, the acyclic aliphatic does not comprise a double or triple bond between the α and β carbons;

n is 0 or 1; and m is 0-3, provided that if R is O and n is 0, m is at least 1.

The nitrophenyl esters contain a nitrophenyl group linked to the oxygen of the carboxylate moiety by a chain that typically comprises no more than five bonds in the main chain (i.e., exclusive of any branching). Typically, the nitrophenyl esters are 2-nitrophenyl esters, but 3-nitrophenyl esters have also been found to undergo photolysis. Thus, in various embodiments, $R_2$ is $NO_2$. In other embodiments, $R_3$ is $NO_2$.

The chain linking the nitrophenyl group to the carboxylate typically comprises two to five bonds in the main chain, and may also comprise one or more alkyl branches. The linker chain typically comprises carbon, oxygen, and/or sulfur atoms, and more typically comprises carbon and oxygen atoms. Thus, in various embodiments, R is $C(R_7R_8)$ or oxygen. If the linker chain comprises one or more alkyl branches, the alkyl branches are typically methyl or ethyl. In certain embodiments, it is preferred that there are no branches or one branch at any given carbon atom in the linker chain. Thus, for example, in various embodiments, R is $C(R_7R_8)$ and one of $R_7$ and $R_8$ is H and the other is H, $CH_3$, or $CH_2CH_3$. Similarly, in various other embodiments, $R_1$ is $C(R_9R_{10})$ and one of $R_9$ and $R_{10}$ is H and the other is H, $CH_3$, or $CH_2CH_3$. In some other embodiments, the chain linking the nitrophenyl group to the carboxylate does not have any branching. For example, in some embodiments, R is $C(R_7R_8)$ and $R_7$ and $R_8$ are both H.

In some embodiments, the linker chain is unbranched and comprises a $C_1$-$C_4$ alkyl chain. For example, in various embodiments, R is $C(R_7R_8)$, $R_7$ and $R_8$ are both H, n is 0, and m is 0, and the linker chain thus comprises a single $CH_2$ moiety. In other embodiments, R is $C(R_7R_8)$; $R_1$ is $C(R_9R_{10})$; $R_7$, $R_8$, $R_9$, and $R_{10}$ are all H; n is 1; and m is 0. In these embodiments, the linker chain comprises a $C_2$ alkyl moiety. In yet other embodiments, R is $C(R_7R_8)$, $R_7$ and $R_8$ are both H, n is 0, and m is 1-3, and the linker chain comprises a $C_2$-$C_4$ alkyl moiety.

In still other embodiments, the linker chain comprises an oxygen or sulfur atom. In some embodiments, R is $C(R_7R_8)$ and $R_1$ is O. In other embodiments, R is O and $R_1$ is $C(R_9R_{10})$. For example, in various embodiments, R is $C(R_7R_8)$, $R_7$ and $R_8$ are both H, $R_1$ is O, n is 1, and m is 2. In various other embodiments, R is O, $R_1$ is $C(R_9R_{10})$, $R_9$ and $R_{10}$ are both H, n is 1, and m is 1.

In addition to the nitro group(s) that must be present at one or both of the 2- and 3-positions, the nitrophenyl esters may also have additional substituents on the phenyl ring. For example, in some embodiments, at least one of $R_2$, $R_3$, $R_4$, $R_5$, and $R_6$ is acyclic aliphatic. However, if any of $R_2$, $R_3$, $R_4$, $R_5$, and $R_6$ is acyclic aliphatic, it is preferred that the acyclic aliphatic does not comprise a double or triple bond between the α and β carbons. In embodiments where at least one of $R_2$, $R_3$, $R_4$, $R_5$, and $R_6$ is acyclic aliphatic, the acyclic aliphatic typically is $C_1$-$C_{18}$ acyclic aliphatic, and more typically $C_1$-$C_{18}$ alkyl.

In various other embodiments, at least one of $R_2$, $R_3$, $R_4$, $R_5$, and $R_6$ is alkoxy. In such embodiments, the alkoxy is typically $C_1$-$C_{18}$ alkoxy, for example methoxy. In some embodiments, both of $R_4$ and $R_5$ are alkoxy, for example methoxy.

In yet other embodiments, at least one of $R_2$, $R_3$, $R_4$, $R_5$, and $R_6$ is amine. In such embodiments, the amine may be $NH_2$ or a substituted amine. If the amine is a substituted amine, it is preferred that there is not an amide at the ring position adjacent to the nitro group, because such an amide would be susceptible to photocleavage.

Particular examples of nitrophenyl esters of carboxylic acid agrochemicals of formula (III) include compounds wherein:

$R_2$ is $NO_2$; each of $R_3$, $R_4$, $R_5$, and $R_6$ is H; R is $C(R_7R_8)$; $R_7$ and $R_8$ are both H; n is 0; and m is 0;

$R_2$ is $NO_2$, each of $R_3$ and $R_6$ is H, each of $R_4$ and $R_5$ are methoxy, R is $C(R_7R_8)$, $R_7$ and $R_8$ are both H, n is 0, and m is 0;

$R_3$ is $NO_2$; each of $R_2$, $R_4$, $R_5$, and $R_6$ is H; R is $C(R_7R_8)$; $R_7$ and $R_8$ are both H; n is 0; and m is 0;

$R_2$ is $NO_2$; each of $R_3$, $R_4$, $R_5$, and $R_6$ is H; R is $C(R_7R_8)$; $R_1$ is $C(R_9R_{10})$; $R_7$, $R_8$, $R_9$, and $R_{10}$ are all H; n is 1; and m is 0;

$R_2$ is $NO_2$; each of $R_3$, $R_4$, $R_5$, and $R_6$ is H; R is O; $R_1$ is $C(R_9R_{10})$; $R_9$ and $R_{10}$ are both H; n is 1; and m is 1; or $R_2$ is $NO_2$; each of $R_3$, $R_4$, $R_5$, and $R_6$ is H; R is $C(R_7R_8)$; $R_7$ and $R_8$ are both H; $R_1$ is O, n is 1, and m is 2.

Thus, where the carboxylic acid agrochemical is dicamba, particular examples of the nitrophenyl esters of formula (III) include the following compounds:

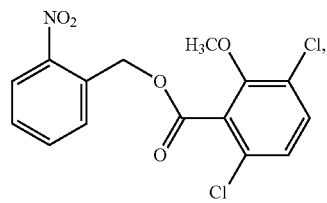

2-nitrobenzyl ester of dicamba

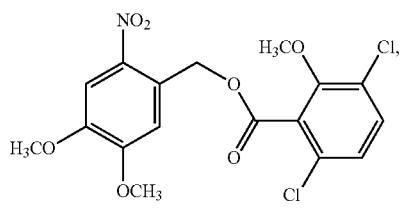

6-nitrovertarul ester of dicamba

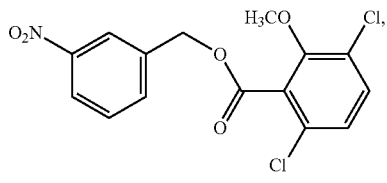

3-nitrobenzyl ester of dicamba

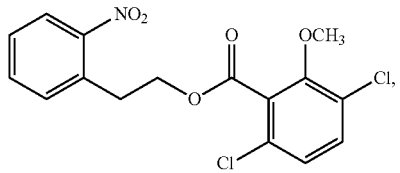

2-nitrophenethyl ester of dicamba

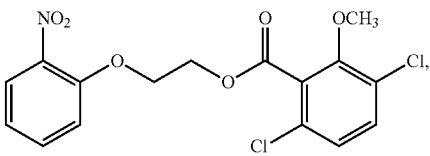

2-(2-nitrophenoxy)ethyl ester of dicamba

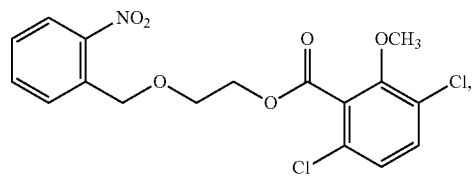

2-(2-nitrophenoxy)ethyl ester of dicamba

The 2-nitrobenzyl (1a) and 2-nitrophenethyl (2) esters of dicamba can readily be prepared by esterification with the parent alcohol or, in the case of the 2-nitrobenzyl ester, by halide displacement from 2-nitrobenzyl chloride or 2-nitrobenzyl bromide. Syntheses for these compounds are described in the Examples below.

The solubility of the nitrophenyl esters in organic solvents increases as the length of the linker chain increases, and this increased solubility enables higher loading to be achieved in emulsifiable concentrate formulations. However, for nitrophenyl esters having linkers comprising more than two atoms (for example, compounds 3 and 4 above) the rate of photolysis decreases. A compound such as compound 2 would be suitable for emulsifiable concentrate formulations intended for post-emergent weed control. On the other hand, a compound such as compound 1a would be suitable for suspension concentrate or wettable granule formulations due to its higher melting point and lower cost.

It has also been discovered that analogs of 1a, such as 1b and 1c, are also effective herbicides. Compound 1b, the 6-nitroveratryl ester of dicamba, is significantly less soluble than 1a and is therefore better suited to suspension concentrates. Compound 1c, the 3-nitrobenzyl ester of dicamba, undergoes slower and less efficient photolysis than the 2-nitrobenzyl ester, 1a.

Field tests of emulsifiable concentrates of compounds 1a and 2 showed them to be slightly more effective than the diglycolamine salt of dicamba for control of broadleaf weeds. Similar activity was seen in greenhouse tests of post-emergent control of velvetleaf, described in further detail in the Examples below. Without being bound to any particular theory, the somewhat better performance in the field is thought to be due to the availability of ultraviolet light outdoors. Thus, compounds 1a and 2 are particularly suitable for post-emergent control of broadleaf weeds, especially where minimizing off-site movement is a priority.

In other embodiments, the carboxylic acid agrochemical is 2,4-D. In such embodiments, particular examples of the nitrophenyl esters of formula (III) include the following compounds:

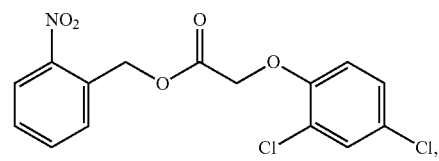

2-nitrobenzyl ester of 2,4-D

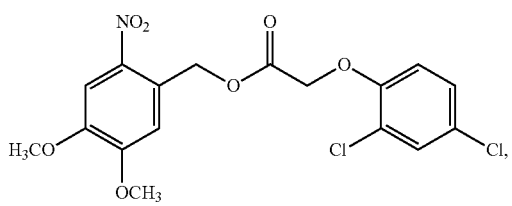

6-nitroveratryl ester of 2,4-D

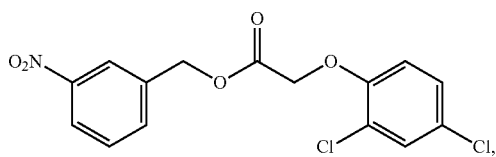

3-nitrobenzyl estser of 2,4-D

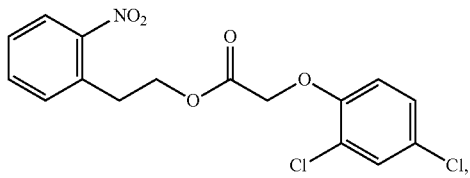

2-nitrophenethyl ester of 2,4-D

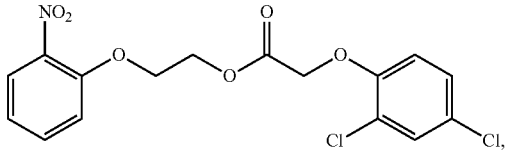

2-(2-nitrophenoxy)ethyl ester of 2,4-D

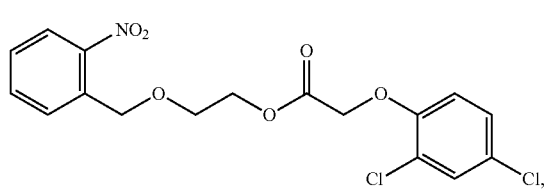

2-(2-nitrobenzyoxy)ethyl ester of 2,4-D

B. Phenacylmethyl Esters

Another class of esters of carboxylic acid agrochemicals that have been found to undergo photo-induced cleavage to form the agronomically active carboxylic acid agrochemical when exposed to natural or artificial light are the phenacylmethyl esters. This class of esters includes esters of carboxylic acid agrochemicals comprising a photolabile protecting group which includes a phenacylmethyl ester moiety. The phenacylmethyl esters typically have the formula (V):

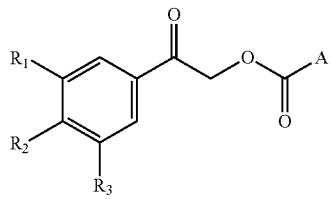

wherein $R_2$ is hydroxy, alkoxy, or substituted alkoxy; and $R_1$ and $R_3$ are independently H, hydroxy, alkoxy, substituted alkoxy, or $C_1$-$C_{18}$ unsubstituted or substituted acyclic aliphatic, provided that if either of $R_1$ and $R_3$ is $C_1$-$C_{18}$ unsubstituted or substituted acyclic aliphatic, the acyclic aliphatic does not comprise a double or triple bond between the α and β carbons.

In various embodiments, at least one of $R_1$, $R_2$, and $R_3$ is alkoxy or substituted alkoxy. In such embodiments, the alkoxy or substituted alkoxy can have the formula: —O—CH$_2$—$R_4$, wherein $R_4$ is H, $C_1$-$C_{17}$ unsubstituted or substituted acyclic aliphatic, an amine, an aliphatic amine, an aliphatic diamine, a carboxylic acid, a sulfonic acid, hydroxy, an aliphatic ring, or an aromatic ring.

For example, in some embodiments, $R_2$ is alkoxy and $R_1$ and $R_3$ are both H. In various other embodiments, $R_2$ is hydroxy and $R_1$ and $R_3$ are both H.

Particular examples of phenacylmethyl esters of formula (V) include compounds wherein $R_2$ is methoxy or n-butoxy, and $R_1$ and $R_3$ are both H. For example, where the carboxylic acid agrochemical is dicamba, particular examples of the phenacylmethyl esters of formula (V) include the following compounds.

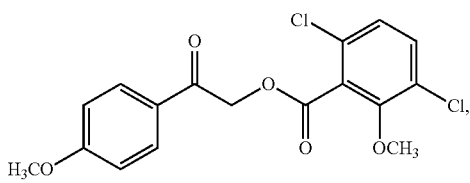

4-methoxyphenacylmethyl ester of dicamba

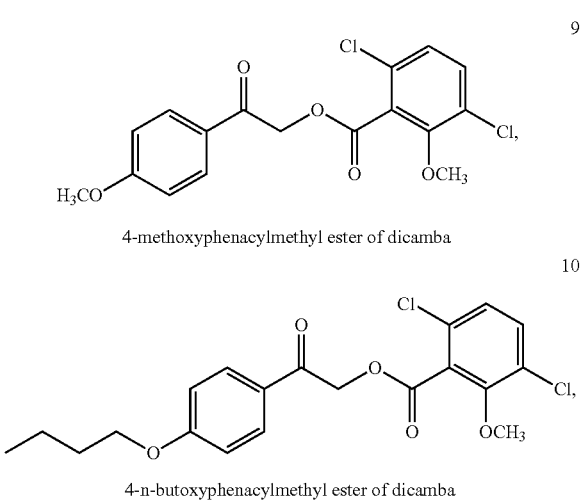

4-n-butoxyphenacylmethyl ester of dicamba

The 4-methoxyphenacyl methyl ester of dicamba (9) and the analogous 4-n-butoxyphenacyl methyl ester (10) can readily be prepared from dicamba in high yield, as described below in the Examples. Both of these compounds undergo photo-release to release dicamba. In vitro studies described below in the Examples indicate that the photo-efficiency of dicamba generation from compound 9 is virtually 100%. Compound 9 is relatively insoluble and is best suited for use in suspension concentrates; however, an emulsifiable concentrate of 9 in monochlorobenzene was shown to be effective for post-emergent control of broadleaf weeds, as described in the Examples below. It has also been found that efficient photo-release of 9 in a suspension concentrate formulation occurs over several weeks, further demonstrating the ability of 9 to provide extended pre-emergent weed control.

Compound 10 is a liquid at room temperature and is also effective for post-emergent broadleaf weed control when formulated as an emulsifiable concentrate, as described in the Example below.

In other embodiments, the carboxylic acid agrochemical is 2,4-D. In such embodiments, particular examples of the phenacylmethyl esters of formula (V) include the following compounds:

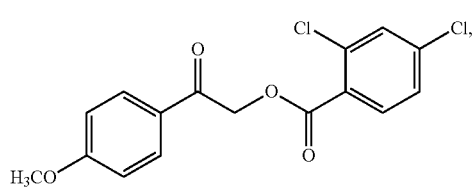

4-methoxyphenacylmethyl ester of 2,4-D

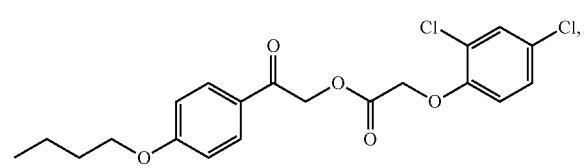

4-n-butoxyphenacylmethyl ester of 2,4-D

C. Other Esters

It has further been discovered that certain other aromatic esters of carboxylic acid agrochemicals also provide for efficient release of an active agrochemical. For example, in various embodiments, the esters of the carboxylic acid agrochemicals have the formula (VI):

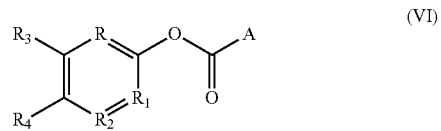

wherein at least one of R and $R_1$ is N, and the other of R and $R_1$ is N or C—$R_5$;
$R_2$ is N or CH;
$R_3$ and $R_4$ are H, acyclic alkyl, substituted acyclic alkyl, or together form a phenyl ring;
and $R_5$ is H, acyclic alkyl, or substituted acyclic alkyl.

In the esters of carboxylic acid agrochemicals of formula (VI), one or both of R and $R_1$ are nitrogen. It has been discovered that compounds having a nitrogen atom at one or both of these positions achieve efficient release of the agrochemical. Such release generally occurs through hydrolysis, although photolysis can also contribute. Compounds of formulas VII, XII, and XIII, discussed below, also have nitrogen-containing aromatic rings and undergo hydrolysis under typical agronomic conditions. Without being bound to any particular theory, it is believed that a ring nitrogen atom adjacent to the phenolic carbon of the ester stabilizes adducts with water or hydroxide by a mechanism similar to that shown below for the 2-hydroxypyridine ester of dicamba:

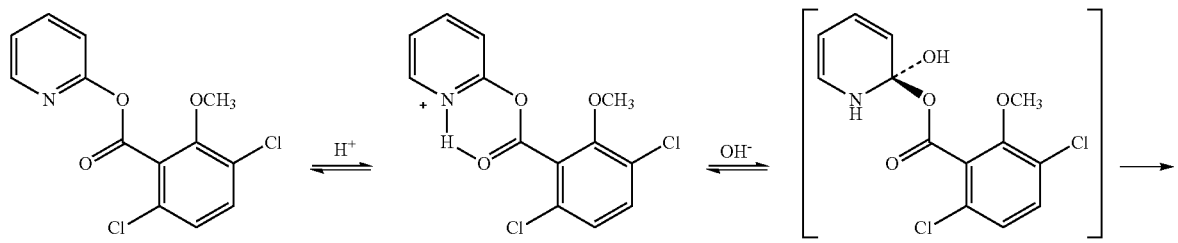

14, 2-hydroxypyridine ester of dicamba

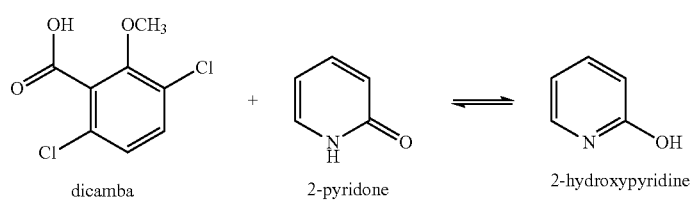

dicamba    2-pyridone    2-hydroxypyridine

As described below, some esters of this type, such as the 2-quinoxalinol ester of dicamba, also under photolysis to yield the carboxylic acid agrochemical. Without being bound to any particular theory, it is believed that in the case of photolysis, the nitrogen atoms at the R and/or $R_1$ positions serve two functions: (1) blocking sites α to the ester in order to prevent recombination and ketone formation after photo-induced cleavage of the ester; and (2) inhibiting recombination by enabling the aromatic hydroxy group to tautomerize to the keto form, preventing recombination.

In various embodiments of the esters of carboxylic acid agrochemicals of formula (VI), $R_1$ is C—$R_5$ and $R_5$ is H, alkyl (e.g., methyl), or substituted alkyl.

In addition, in various embodiments, $R_2$ can also be nitrogen. In other embodiments, $R_2$ is CH.

In the esters of carboxylic acid agrochemicals of formula (VI), $R_3$ and $R_4$ are H, acyclic alkyl, substituted acyclic alkyl, or together form a phenyl ring. Typically, $R_3$ and $R_4$ are both H or together form a phenyl ring.

In various embodiments of the esters of carboxylic acid agrochemicals of formula (VI), at least one of $R_3$, $R_4$, and $R_5$ is $C_1$-$C_{18}$ acyclic alkyl or $C_1$-$C_{18}$ substituted acyclic alkyl. The $C_1$-$C_{18}$ substituted acyclic alkyl can be substituted with, for example, one or more hydroxy groups or one or more sulfonic acid groups.

Particular examples of the esters of carboxylic acid agrochemicals of formula (VI) include compounds wherein:

R and $R_2$ are N; $R_1$ is C—$R_5$; $R_3$ and $R_4$ together form a phenyl ring; and $R_5$ is H;

R and $R_2$ are N; $R_1$ is C—$R_5$; $R_3$ and $R_4$ together form a phenyl ring; and $R_5$ is methyl; or R is N; $R_1$ is C—$R_5$; $R_2$ is CH; and $R_3$, $R_4$, and $R_5$ are all H.

Thus, for example, where the carboxylic acid agrochemical is dicamba, particular examples of the esters of carboxylic acid agrochemicals of formula (VI) include the following compounds:

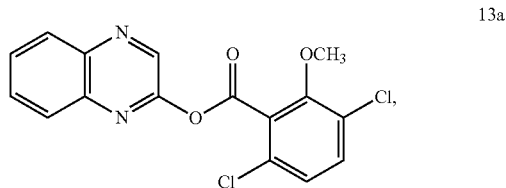

2-Quinoxalinol ester of dicamba

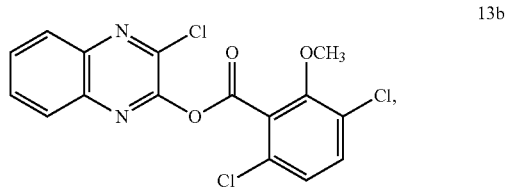

3-methyl-2-quinoxalinol ester of dicamba

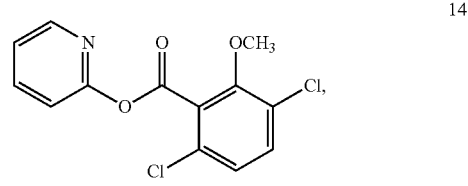

2-hydroxypyridine ester of dicamba

A proposed scheme for the photo release of dicamba from the 2-quinoxalinol ester 13a is shown below:

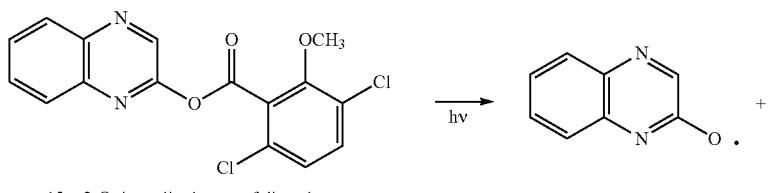

13a, 2-Quinoxalinol ester of dicamba

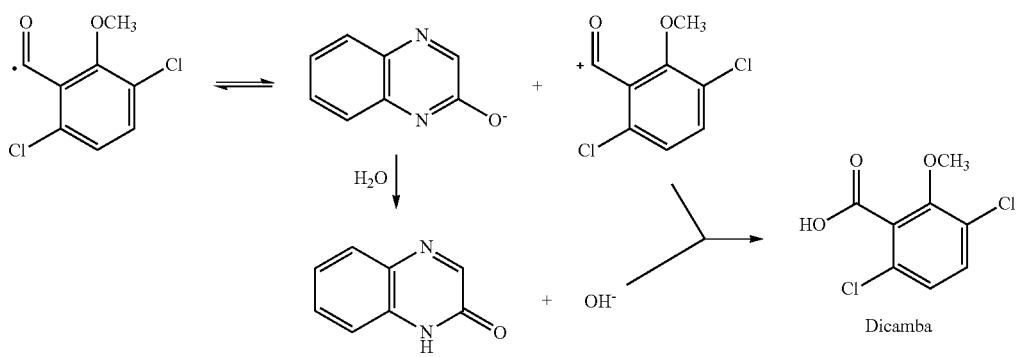

Although the mechanistic detail in this scheme is not firmly established, the outstanding efficacy of the photo and hydrolytically-labile 2-quinoxalinol protecting group is shown in the Examples below.

When used as an emulsifiable concentrate, the 2-quinoxalinol ester of dicamba, 13a, has similar post-emergent activity for control of broadleaf weeds as the diglycolamine salt of dicamba, while exhibiting superior extended pre-emergent control of Palmer amaranth at 21 and 44 days after treatment. The 2-hydroxypyridine ester 14 also undergoes efficient cleavage to form dicamba, as shown in the Examples below. Ester 14 is readily soluble in organic solvents and can be formulated as an emulsifiable concentrate or a suspension concentrate.

In other embodiments, the carboxylic acid agrochemical is 2,4-D. In such embodiments, particular examples of the esters of formula (VI) include the following compounds:

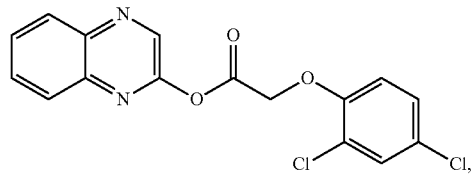

2-Quinoxalinol ester of 2,4-D

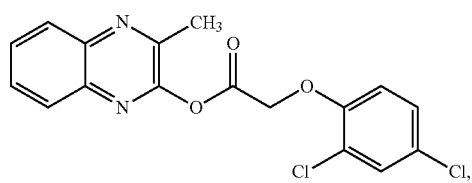

3-methyl-2-quinoxalinol ester of 2,4-D

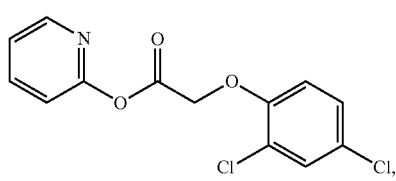

2-hydroxypyridine ester of 2,4-D

In other various embodiments, the ester is a diester of a carboxylic acid agrochemical having the formula (VII):

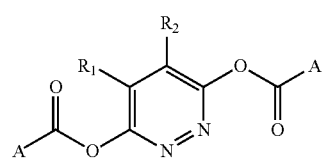

wherein $R_1$ and $R_2$ are independently H or $C_1$-$C_8$ alkyl, or together form a phenyl ring. $R_1$ and $R_2$ are typically both H, or together form a phenyl ring.

In various embodiments, the carboxylic acid agrochemical is dicamba, and examples of the diesters of formula (VII) include the following compounds:

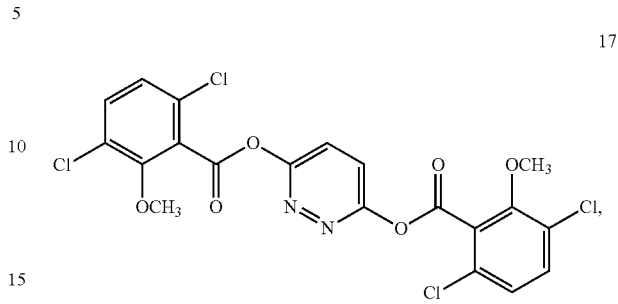

Maleic hydrazide diester of dicamba

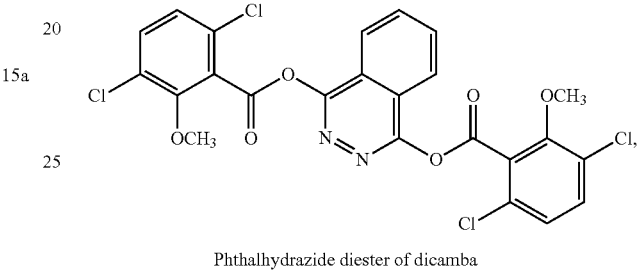

Phthalhydrazide diester of dicamba

Like the esters of formula VI, the esters of formula VII generally revert to the parent carboxylic acid by hydrolysis rather than by photolysis. The maleic hydrazide and phthalhydrazide diesters (17 and 18) undergo efficient cleavage to form dicamba. The phthalhydrazide diester, 18, is highly insoluble and is preferably formulated as a suspension concentrate. The maleic hydrazide diester, 17, is readily soluble in organic solvents and can be formulated as an emulsifiable concentrate or a suspension concentrate.

In various other embodiments, the carboxylic acid agrochemical is 2,4-D, and examples of the diesters of formula (VII) include the following compounds:

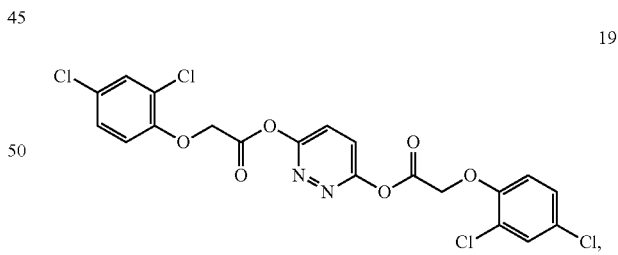

Maleic hydrazide diester of 2,4-D

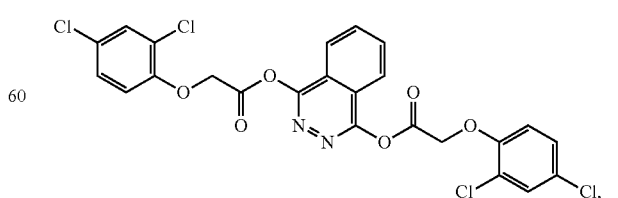

Phthalhydrazide diester of 2,4-D

In yet other embodiments, the ester of a carboxylic acid agrochemical has the formula (VIII):

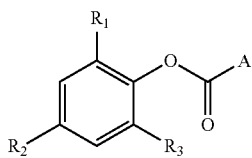

(VIII)

wherein $R_1$, $R_2$, and $R_3$ are alkyl.

In the esters of formula (VIII), the substitutions ortho and para to the ester block ketone formation. Typically, at least one of the ortho substituents is branched to prevent recombination of the phenol and acyl photo-fragments. For example, an isopropyl or tertiary butyl substituent can be present at the ortho position. Thus, typically at least one of $R_1$ and $R_3$ is branched alkyl, e.g., isopropyl or t-butyl.

In addition, in various embodiments of the esters of formula (VIII), at least one of $R_1$ and $R_2$ is methyl. As one example, in a particular embodiment $R_1$ and $R_2$ are both methyl and $R_3$ is t-butyl. Where the carboxylic acid agrochemical is dicamba, this ester of formula (VIII) has the following structure:

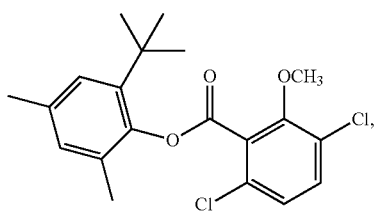

21

2-t-butyl-4,6-dimethylphenyl ester of dicamba

Ester 21 has been shown to undergo photo-release of dicamba in vitro. In addition, the substituted phenol byproducts formed upon photo-release of the agrochemical from the esters of formula (VIII) are effective anti-oxidants and can provide plant health benefits under some circumstances.

In other embodiments of the esters of formula (VIII), the carboxylic acid agrochemical is 2,4-D. Thus, for example, an ester of formula (VIII) can have the following structure:

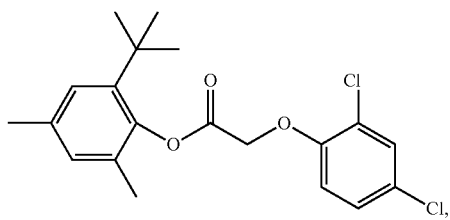

22

2-t-butyl-4,6-dimethylphenyl ester of 2,4-D

In yet other various embodiments, a phenolic agrochemical can be incorporated into the photolabile ester of a carboxylic acid agrochemical, thereby affording a photolabile ester which provides photo-release of two different agrochemicals that may have different modes of action. In some such embodiments, the ester of a carboxylic acid agrochemical has the formula (IX):

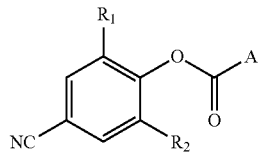

(IX)

wherein $R_1$ and $R_2$ are halogen.

In the esters of formula (IX), the phenolic agrochemical is typically chloroxynil, bromoxynil, or ioxynil. Thus, typically, $R_1$ and $R_2$ are both chloro (where the phenolic agrochemical is chloroxynil), $R_1$ and $R_2$ are both bromo (where the phenolic agrochemical is bromoxynil), or $R_1$ and $R_2$ are both iodo (where the phenolic agrochemical is ioxynil). The chloroxynil, bromoxynil, and ioxynil esters of dicamba have the following structures:

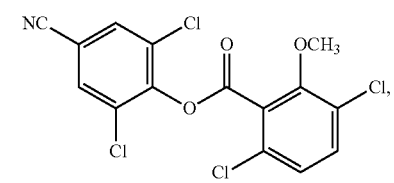

23a chloroxynil ester of dicamba

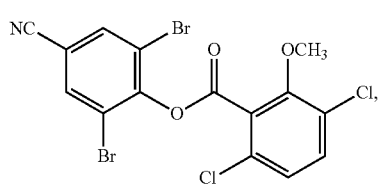

23b bromoxynil ester of dicamba

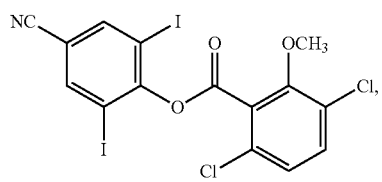

23c ioxynil ester of dicamba

The chloroxynil, bromoxynil and ioxynil esters of dicamba (23a, 23b, and 23c) provide photo-release of dicamba and an herbicide with a second mode of action. Chloroxynil, bromoxynil, and ioxynil esters can also be used to provide photo-release of other carboxylic acid agrochemicals. For example, the chloroxynil, bromoxynil, and ioxynil esters of 2,4-D have the following structures:

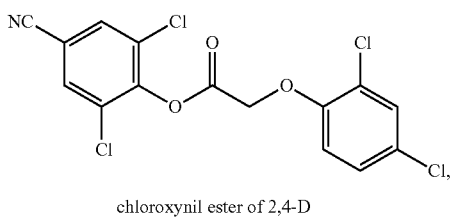

chloroxynil ester of 2,4-D

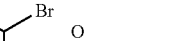

bromoxynil ester of 2,4-D

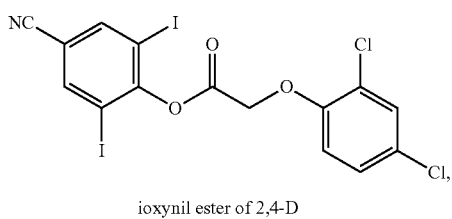

ioxynil ester of 2,4-D

Similarly, the fungicide quinolinol can be used to form a photo-labile ester of a carboxylic acid agrochemical. In such embodiments, the ester of a carboxylic acid agrochemical has the formula (X):

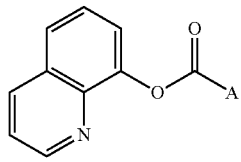

(X)

For example, the quinolinol esters of dicamba and 2,4-D have the following structures:

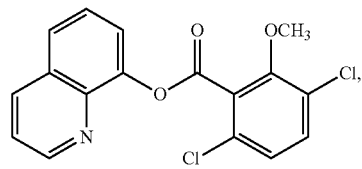

quinolinol ester of dicamba

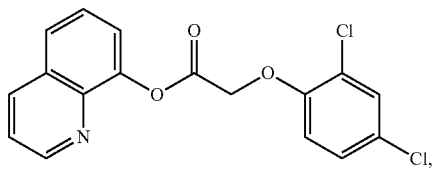

quinolinol ester of 2,4-D

In other embodiments, the herbicide medinoterb can be used to form a photo-labile ester of a carboxylic acid agrochemical. In such embodiments, the ester of a carboxylic acid agrochemical has the formula (XI):

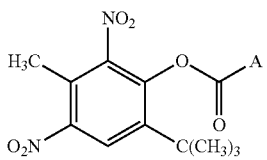

(XI)

For example, the medinoterb esters of dicamba and 2,4-D have the following structures:

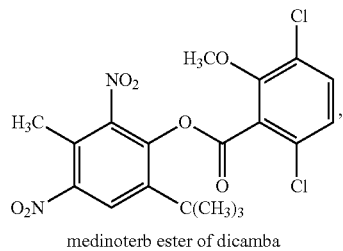

medinoterb ester of dicamba

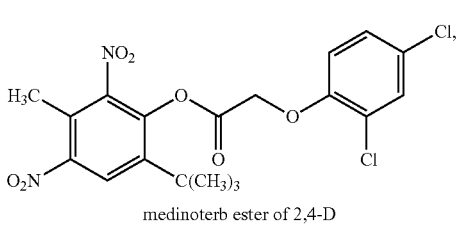

medinoterb ester of 2,4-D

D. Activated Benzylic Esters

In some embodiments, the ester of a carboxylic acid agrochemical has the formula (XII):

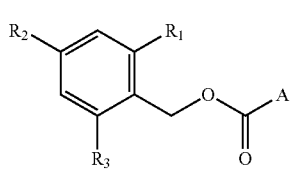

(XII)

wherein at least one of $R_1$, $R_2$, and $R_3$ is an electron-donating group;

and the others of $R_1$, $R_2$, and $R_3$ are independently H or an electron-donating group;

provided that none of $R_1$, $R_2$, and $R_3$ is an electron-withdrawing group.

Suitable electron-donating groups include alkoxy (e.g. methoxy), alkyl, amino, alkylamino, and dialkylamino.

In embodiments wherein the electron-donating group is alkyl, alkylamino, or dialkylamino the alkyl is typically $C_1$-$C_{18}$ alkyl.

In embodiments wherein the electron-donating group is alkoxy, the alkoxy is typically $C_1$-$C_{18}$ alkoxy. For instance, in certain embodiments, at least one of $R_1$, $R_2$, and $R_3$ is methoxy. For example, in some embodiments, $R_2$ is methoxy and $R_1$ and $R_3$ are both H. Where the carboxylic acid agrochemical is dicamba, this ester of formula (XII) has the following structure:

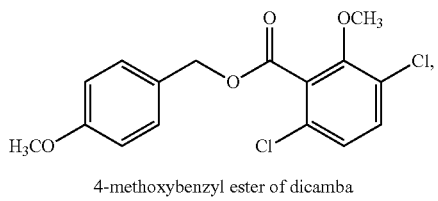

4-methoxybenzyl ester of dicamba

In other embodiments of the esters of formula (XII), the carboxylic acid agrochemical is 2,4-D. Where the carboxylic acid agrochemical is 2,4-D, a particular example of a compound of formula (XII) has the following structure:

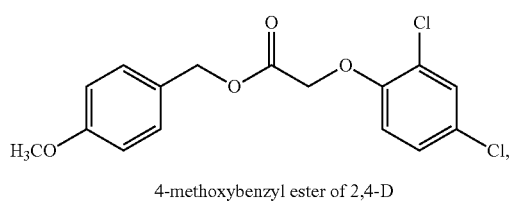

4-methoxybenzyl ester of 2,4-D

Unactivated benzylic esters of aromatic carboxylic acids such as dicamba are resistant to hydrolysis under typical agronomic conditions. However, activated benzylic esters of formula (XII), particularly those containing alkoxy or dialkylamino groups in the ortho or para position, undergo hydrolysis by the mechanism shown below, in which elimination of the dicamba anion occurs directly followed by hydrolysis of the stabilized benzylic cation. The 4-methoxybenzyl ester of dicamba, 29a, is suitable for the fast release of dicamba. Such rapid hydrolysis is useful in dry soil (which slows the rate of hydrolysis) or when physical methods such as encapsulation are used to govern the rate of ester release to the environment.

E. Activated Phenolic Esters

In still other embodiments, the ester of a carboxylic acid agrochemical has the formula (XIII):

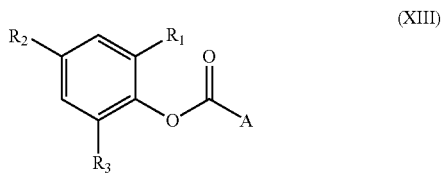

wherein at least one of $R_1$, $R_2$, and $R_3$ is an electron-donating group;

and the others of $R_1$, $R_2$, and $R_3$ are independently H or an electron-donating group;

provided that none of $R_1$, $R_2$, and $R_3$ is an electron-withdrawing group.

Suitable electron-donating groups include alkoxy (e.g., methoxy), alkyl, amino, alkylamino, and dialkylamino.

In embodiments wherein the electron-donating group is alkyl, alkylamino, or dialkylamino the alkyl is typically $C_1$-$C_{18}$ alkyl.

In embodiments wherein the electron-donating group is alkoxy, the alkoxy is typically $C_1$-$C_{18}$ alkoxy. For instance, in certain embodiments, at least one of $R_1$, $R_2$, and $R_3$ is methoxy. For example, in some embodiments, $R_2$ is methoxy and $R_1$ and $R_3$ are H. Where the carboxylic acid agrochemical is dicamba, this ester of formula (XIII) has the following structure:

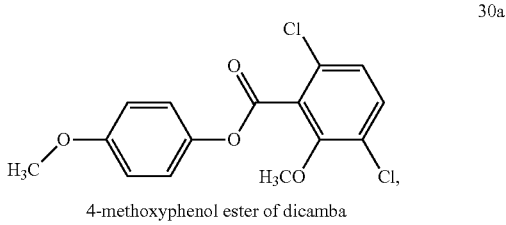

4-methoxyphenol ester of dicamba

In other embodiments of the esters of formula (XIII), the carboxylic acid agrochemical is 2,4-D. Where the carboxylic acid agrochemical is 2,4-D, a particular example of a compound of formula (XIII) has the following structure:

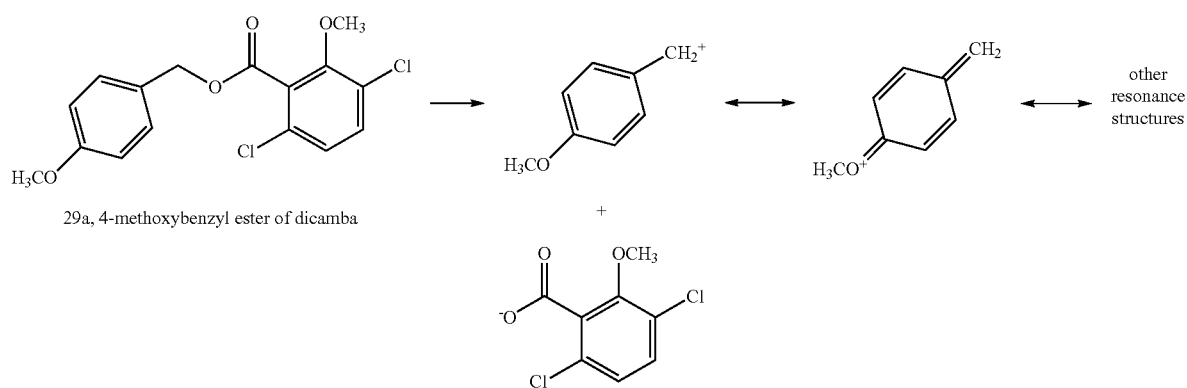

29a, 4-methoxybenzyl ester of dicamba

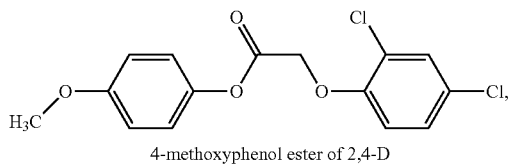

4-methoxyphenol ester of 2,4-D

Methoxy and dialkylamino groups promote the photolysis of phenolic esters of carboxylic acid agrochemicals by a mechanism similar to that by which they promote hydrolysis of benzylic esters. In both cases, the effect is to promote the elimination of the carboxylate anion and a stabilized cation, as shown below for the 4-methoxyphenyl ester of dicamba, 30a. Thus esters of structural formula (XIII) undergo photo-release of carboxylic acids. Photo-release is significantly slower than for esters of formula (III) or (V), providing further suppression of volatility and a more extended release of the active agrochemical.

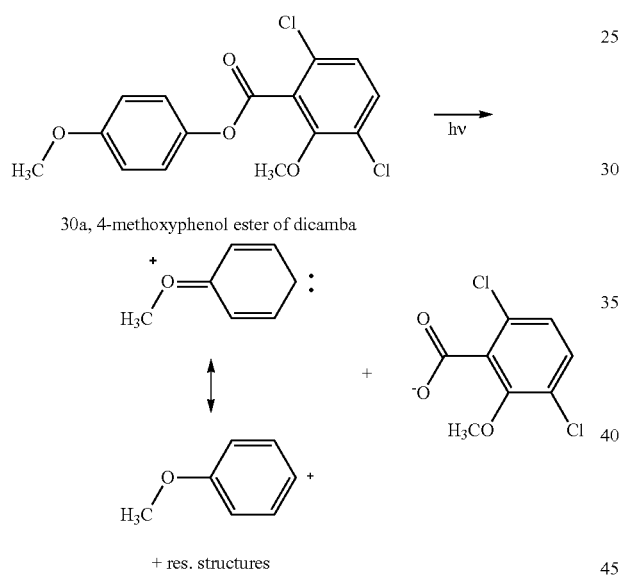

30a, 4-methoxyphenol ester of dicamba

+ res. structures

F. Benzylic Esters Prepared by the Baylis-Hillman Reaction

In other embodiments, the ester of a carboxylic acid agrochemical is a benzylic ester having the formula (XIV):

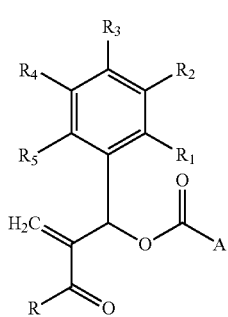

(XIV)

wherein R is alkyl, aryl, or alkoxy;

at least one of $R_1$, $R_2$, $R_3$, $R_4$, and $R_5$ is an electron-withdrawing group;

and the others of $R_1$, $R_2$, $R_3$, $R_4$, and $R_5$ are independently H, alkyl, alkoxy, dialkylamino, or halogen.

Suitable electron withdrawing groups include nitro, ester, and sulfonate. Thus, for example, in certain compounds of formula (XIV), at least one of $R_1$, $R_2$, $R_3$, $R_4$, and $R_5$ is nitro.

In embodiments wherein one or more of R, $R_1$, $R_2$, $R_3$, $R_4$, and $R_5$ is alkyl, the alkyl is typically $C_1$-$C_{18}$ alkyl. Thus, for example, in some embodiments, one or more of R, $R_1$, $R_2$, $R_3$, $R_4$, and $R_5$ is methyl or ethyl.

When one or more of R, $R_1$, $R_2$, $R_3$, $R_4$, and $R_5$ is alkoxy, the alkoxy is suitably $C_1$-$C_{18}$ alkoxy (e.g., methoxy or ethoxy).

Typical R substituents include methyl, ethyl, substituted phenoxy, and $C_1$-$C_{18}$ alkoxy. For example, in certain embodiments, R is ethoxy.

Particular examples of esters of formula (XIV) include compounds wherein:

R is ethoxy, $R_1$ is nitro, and each of $R_2$, $R_3$, $R_4$, and $R_5$ are H;

R is ethoxy, $R_2$ is nitro, and each of $R_1$, $R_3$, $R_4$, and $R_5$ are H; or R is ethoxy, $R_3$ is nitro, and each of $R_1$, $R_2$, $R_4$, and $R_5$ are H.

Thus, where the carboxylic acid agrochemical is dicamba, particular examples of the esters of formula (XIV) include the following compounds:

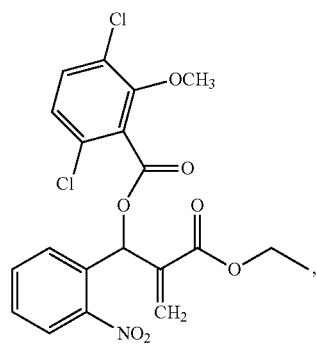

Ethyl-2-(2-nitrobenzyl dicambyl) acrylate

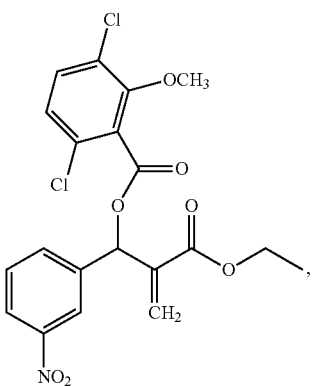

Ethyl-2-(3-nitrobenzyl dicambyl) acrylate

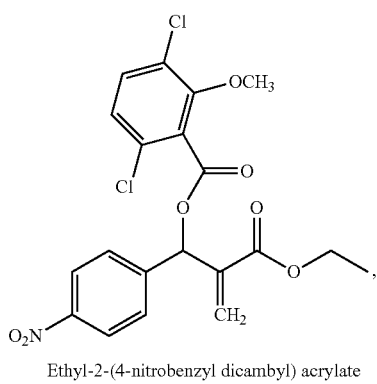

Ethyl-2-(4-nitrobenzyl dicambyl) acrylate

In other embodiments of the esters of formula (XIV), the carboxylic acid agrochemical is 2,4-D. For such embodiments, particular examples of the esters of formula (XIV) include the following compounds:

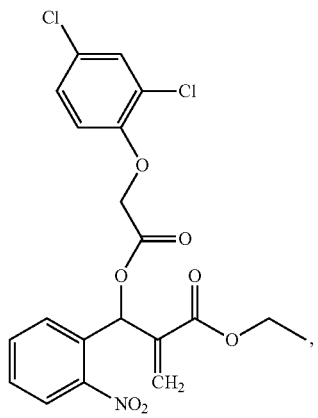

Ethyl-2-(2-nitrobenzyl 2,4-dichlorophenoxyacetyl) acrylate

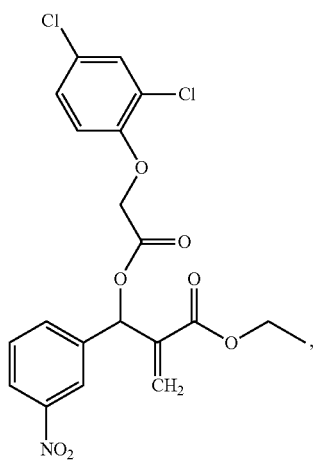

Ethyl-2-(3-nitrobenzyl 2,4-dichlorophenoxyacetyl) acrylate

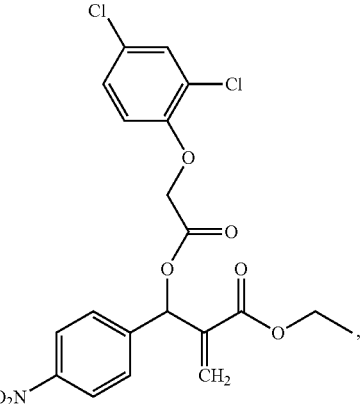

Ethyl-2-(4-nitrobenzyl 2,4-dichlorophenoxyacetyl) acrylate

Hydrolytically labile esters of aromatic carboxylic acids of formula (XIV) can be conveniently prepared via the Baylis-Hillman reaction followed by esterification with the carboxylic acid agrochemical. The Baylis-Hillman reaction is reviewed in Drewes S. E., Roos G. H. P., "Synthetic Potential of the Tertiary Amine-Catalysed Reaction of Activated Vinyl Carbanions with Aldehyde," *Tetrahedron*, 1988, 44, 4653-70) and Basavaiah, D., Rao, P. D., Hyma, R. S., "The Baylis-Hillman Reaction: A Novel Carbon-Carbon Bond Forming Reaction," *Tetrahdedron*, 1996, 8001-62. The parent alcohols of the present invention are obtained by reaction of a vinyl compounds with an electron-withdrawing group and a substituted benzaldehyde catalyzed by a tertiary amine, preferably diazabicyclo[2,2,2] octane, commonly known as "DABCO" or quinuclidine. Suitable benzaldehydes include nitrobenzaldehydes, particularly when substituted in an ortho orientation. Suitable vinyl compounds include vinyl esters, particularly ethyl acrylate.

The synthesis of a typical parent alcohol by the Baylis-Hillman pathway is shown below. The dicamba ester of this alcohol is designated structure 31a. Two related structures, 31b and 31c, shown above, are also useful for controlled release of dicamba. Laboratory synthetic procedures for esters 31a, 31b, and 31c are given below in the Examples, using reaction times of several days at room temperature. For larger-scale production, it is suitable to conduct the reactions at elevated pressure, which greatly accelerates the rate of the Baylis-Hillman reaction, as described in the literature (Hill, J. S., Isaacs, N. S., *Tetr. Lett.*, 1986, 5007.)

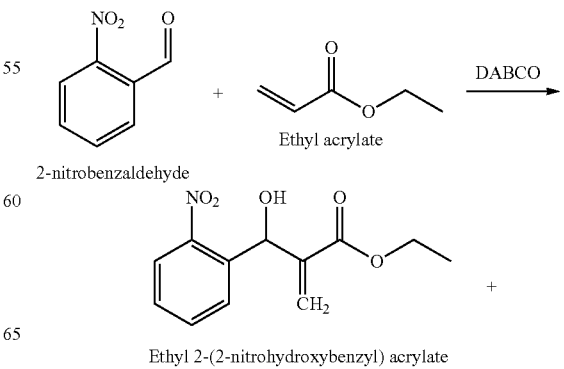

-continued

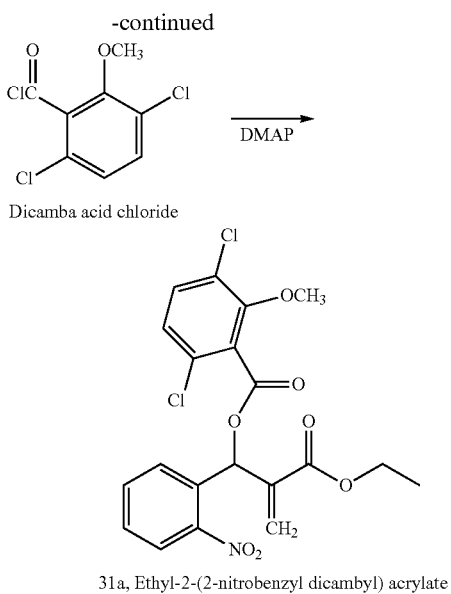

Dicamba acid chloride

31a, Ethyl-2-(2-nitrobenzyl dicambyl) acrylate

The Baylis-Hillman synthesis represents a high yield conversion of low-cost benzaldehydes to benzylic alcohols. In addition, the carbonyl group introduced beta to the benzylic carbon renders the agrochemical ester more hydrolytically labile. The rate of hydrolysis can be enhanced by adding activating groups such as methoxy or dialkylamino to the ortho or para positions of the aromatic ring or conversely reduced by the addition of electron-withdrawing groups such as esters, sulfonates, or nitro groups. Moreover, when a nitro group is present on the ring alpha to the benzylic position, the ester is rendered photo-labile.

G. Esters Obtained by Michael Addition of Activated Olefins to Maleic Hydrazide

In further embodiments, the ester of a carboxylic acid agrochemical has the formula (XV):

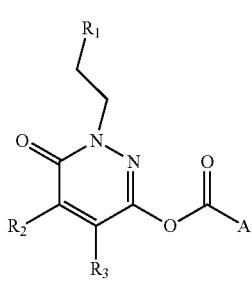

(XV)

wherein $R_1$ is an electron-withdrawing group;
and wherein $R_2$ and $R_3$ are independently H or alkyl.

Suitable electron-withdrawing groups include, for example, nitriles, ketones, aldehydes, esters, carboxylates, and nitro.

In some embodiments of the compounds of formula (XV), both $R_2$ and $R_3$ are H. In other embodiments, one or both of $R_2$ and $R_3$ are alkyl, typically $C_1$-$C_{18}$ alkyl.

Particular examples of carboxylic acid agrochemicals of formula (XV) include compounds wherein:
$R_1$ is —$COCH_3$ and $R_2$ and $R_3$ are both H;
$R_1$ is —CH=O and $R_2$ and $R_3$ are both H; or
$R_1$ is —CN and $R_2$ and $R_3$ are both H;
$R_1$ is —$COOCH_2CH_3$ and $R_2$ and $R_3$ are both H.

Thus, where the carboxylic acid agrochemical is dicamba, particular examples of the esters of formula (XV) include the following compounds:

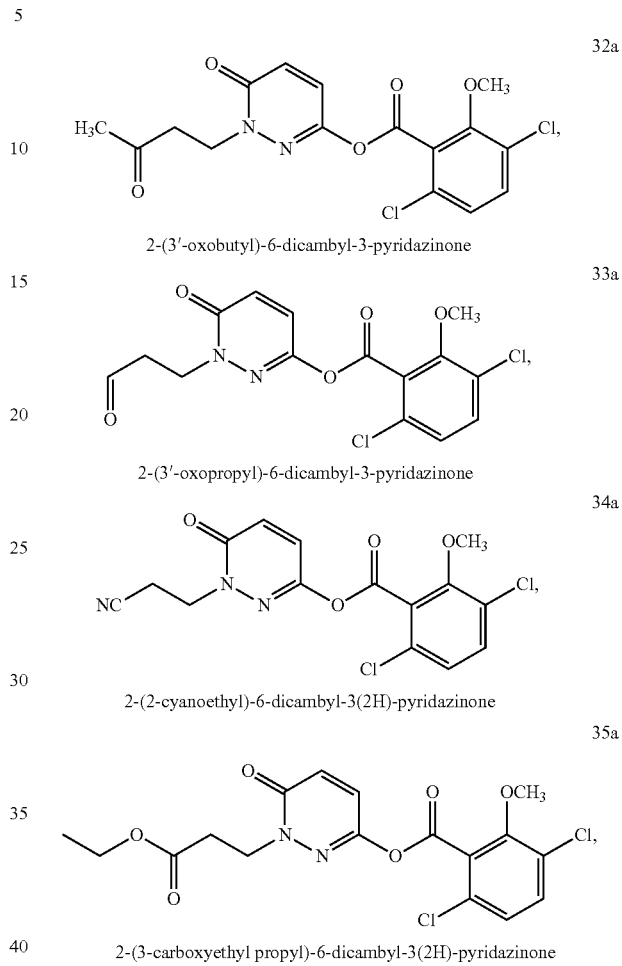

32a
2-(3′-oxobutyl)-6-dicambyl-3-pyridazinone 33a
2-(3′-oxopropyl)-6-dicambyl-3-pyridazinone 34a
2-(2-cyanoethyl)-6-dicambyl-3(2H)-pyridazinone 35a
2-(3-carboxyethyl propyl)-6-dicambyl-3(2H)-pyridazinone In other embodiments of the esters of formula (XV), the carboxylic acid agrochemical is 2,4-D. For such embodiments, particular examples of the esters of formula (XV) include the following compounds:

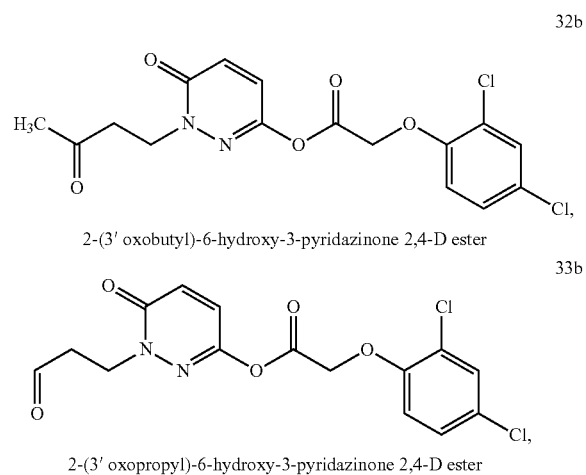

32b
2-(3′ oxobutyl)-6-hydroxy-3-pyridazinone 2,4-D ester 33b
2-(3′ oxopropyl)-6-hydroxy-3-pyridazinone 2,4-D ester

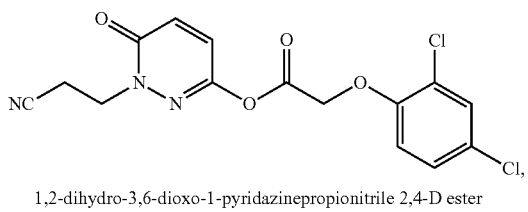

1,2-dihydro-3,6-dioxo-1-pyridazinepropionitrile 2,4-D ester

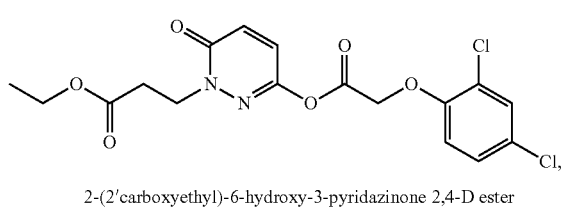

2-(2'carboxyethyl)-6-hydroxy-3-pyridazinone 2,4-D ester

The useful class of esters of structural formula (XV) is obtained by forming an ester of a carboxylic acid agrochemical with an alcohol obtained by base-catalyzed Michael addition of maleic hydrazide to vinyl compounds activated with electron-withdrawing groups. Esters 32a, 33a and 34a, shown above, are obtained by Michael addition of methyl vinyl ketone, acrolein, and acrylonitrile, respectively to maleic hydrazide. The dicamba esters of the Michael adducts can release dicamba by hydrolysis (since there is a nitrogen alpha to the ester linkage) or a combination of hydrolysis and photolysis. The utility of esters of formula (XV) is also due to the fact that the physical properties of the ester can be modified. Ester 34a is an insoluble solid which can be formulated as a suspension concentrate while esters 32a and 33a are effectively room-temperature liquids (although 32a undergoes some crystallization over a period of weeks) and can be formulated as high-loading emulsifiable concentrates. The synthesis of these esters is described in the Examples.

H. Di-Alkylated Hydroxypyridine Esters of Carboxylic Acid Agrochemicals

In still further embodiments, the ester of a carboxylic acid agrochemical has the formula (XVI):

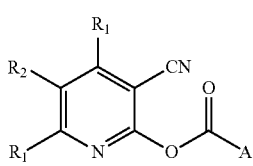

(XVI)

wherein $R_1$ is alkyl and $R_2$ is H, alkyl, or aryl.

The compounds of formula (XVI) are symmetrically substituted with alkyl groups at the $R_1$ positions. $R_1$ is typically $C_1$-$C_{18}$ alkyl. For example, in some esters of formula (XVI), $R_1$ is tertiary-butyl.

In some embodiments, $R_2$ is H. In other embodiments, $R_2$ is alkyl, typically $C_1$-$C_{18}$ alkyl. In still other embodiments, $R_2$ is aryl. When $R_2$ is aryl, the aromatic ring optionally contains nitrogen and is optionally substituted with up to three $C_1$-$C_{18}$ alkyl groups.

In a particular example of an ester of a carboxylic acid agrochemical of formula (XVI), $R_1$ is tertiary-butyl and $R_2$ is H. Thus, where the carboxylic acid agrochemical is dicamba, a particular example of a compound of formula (XVI) has the structure:

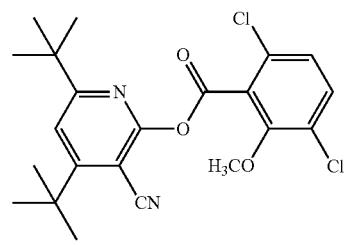

3-cyano-4,6-di-t-butyl-2-pyridone, dicamba ester

In other embodiments of the esters of formula (XVI), the carboxylic acid agrochemical is 2,4-D. Where the carboxylic acid agrochemical is 2,4-D, a particular example of a compound of formula (XVI) has the following structure:

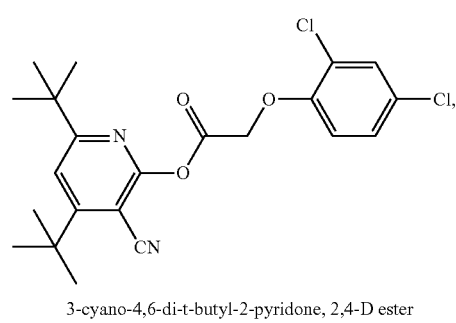

3-cyano-4,6-di-t-butyl-2-pyridone, 2,4-D ester

The solubility of the 2-hydroxypyridine ester of dicamba (compound 14) and other carboxylic acid agrochemicals can be improved and the activity modulated by symmetrical substitution of the ring with alkyl groups ($R_1$ in formula XVI). A convenient synthetic route involving condensation of beta-diketones with 2-cyanoacetamide also adds a nitrile group to the ring. A typical ester of formula (XVI) is the dicamba ester designated compound 36a, where $R_1$ is tertiary butyl and $R_2$ is hydrogen. The synthesis and activity of 36a are described in the Examples.

I. Pyridine Diesters of Carboxylic Acid Agrochemicals

In yet other embodiments, the ester of a carboxylic acid agrochemical has the formula (XVII):

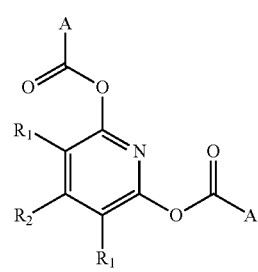

(XVII)

wherein $R_1$ is an electron-withdrawing group;
and $R_2$ is H, a hydrocarbon, or an aromatic group.

Suitable electron-withdrawing groups include, for example, cyano, carboxylalkyl, aldehyde, and nitro. In certain embodiments, $R_1$ is cyano. Where $R_1$ is carboxylalkyl, the alkyl is typically $C_1$ to $C_{12}$ alkyl.

In some embodiments of the esters of formula (XVII), $R_2$ is H. In other embodiments, $R_2$ is a hydrocarbon. Suitable hydrocarbons include $C_1$-$C_{18}$ alkyl. In still other embodiments, $R_2$ is an aromatic group. The aromatic ring optionally contains nitrogen and is optionally substituted with up to three $C_1$-$C_{18}$ alkyl groups. In certain embodiments, $R_2$ is phenyl.

In a particular example of an ester of a carboxylic acid agrochemical of formula (XVII), both $R_1$ is cyano and $R_2$ is phenyl. Thus, where the carboxylic acid agrochemical is dicamba, a particular example of a compound of formula (XVII) has the structure:

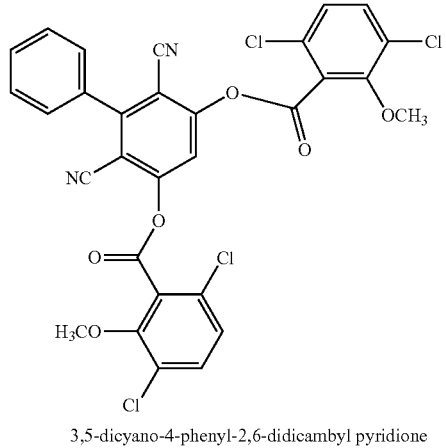

3,5-dicyano-4-phenyl-2,6-didicambyl pyridione

In other embodiments of the esters of formula (XVII), the carboxylic acid agrochemical is 2,4-D. Where the carboxylic acid agrochemical is 2,4-D, a particular example of a compound of formula (XVII) has the following structure:

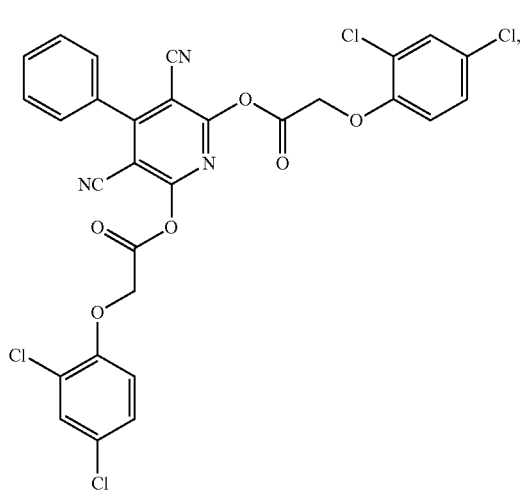

3,5-dicyano-2,6-bis-(2,4-dichlorophenoxyacetyl)-4 phenyl pyridione

The liquid, hydrolytically labile esters of carboxylic acid agrochemicals of formula (XVII) can be obtained by a method involving the double Knoevagel condensation of an aldehyde with two equivalents of 2-cyanoacetamide, yielding a nucleus with two phenolic groups which can be esterified, both adjacent to a ring nitrogen which sensitizes the ester to hydrolysis. A general outline of the synthesis is shown below. Two equivalents of 2-cyanoacetamide are condensed with an aldehyde under basic conditions which is followed, without isolation, by ring closure under neutral conditions. Ring oxidation is facile in the presence of air or other oxidants.

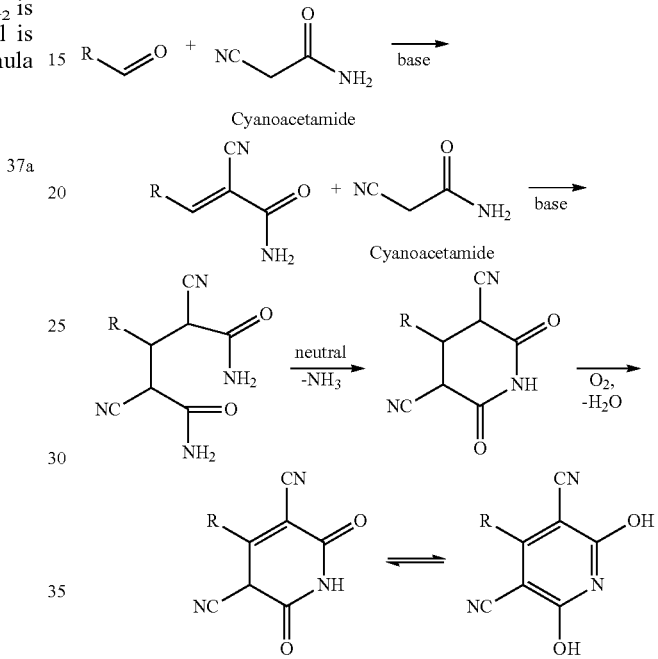

A useful example of esters of formula (XVII) is the ester designated 37a (shown above). Its synthesis and hydrolysis under typical agronomic conditions are described in the Examples.

Synthesis of the Esters of Carboxylic Acid Agrochemicals

As explained in greater detail in the Examples below, the esters of the present invention can be prepared by esterification of the appropriate alcohol with the carboxylic acid agrochemical or reaction of the acid chloride of the agrochemical with the alcohol. The use of dimethylamino pyridine ("DMAP") improves reaction rates and yields when using the acid chloride route, as illustrated in the Examples below for dicamba and 2,4-D esters.

Photo-labile esters of 2,4-D can be prepared similarly to the dicamba esters. Most esters are easily prepared from the acid chloride of 2,4-D. 2,4-D acid chloride and ester synthesis is described in M. S. Newman, et al., *J. Am. Chem. Soc.* 69:718-23 (1947). The synthesis of the 2,4-D esters 5a, 11, and 15a is described in the Examples below.

Thus, the esters of the present invention can be prepared from the acid chloride of dicamba, 2,4-D and other herbicides. The acid chloride is also a convenient intermediate to other esters of the present invention.

The 2-nitrobenzyl esters of dicamba (1) and 2,4-D (5a) are economically prepared from the reaction of 2-nitrobenzyl chloride with dicamba or 2,4-D in the presence of a base as described in Example 4 below. The bases are typically organic amines, particularly triethylamine. It has been found that use of a slightly substoichiometric amount of base relative to dicamba or 2,4-D is preferred as this prevents reaction of free amine with 2-nitrobenzyl chloride.

A typical process for the preparation of 1a is illustrated in FIG. 1. The process can be performed continuously or semi-continuously, but in either case the amine base is regenerated by reaction with a strong aqueous base such as sodium hydroxide and is recycled along with unreacted starting materials and ester that has not precipitated. This method is also applicable to the 2-nitrobenzyl ester of 2,4-D, 5a. Preferably, an excess of 2-nitrobenzyl chloride is present in the reaction mixture and a polar, hydrophobic solvent such a methylene chloride or 1,2-dichlorobenzene is utilized. 2-nitrobenzyl bromide can also be used in this process, as described in Example 14.

2-nitrobenzyl chloride is typically prepared by chlorination of 2-nitrotoluene. Selective monochlorination of toluene at partial conversion is known and is described in *Chlorotoluenes, in Kirk-Othmer Encyclopedia of Chemical Technology* (5th ed. 2004). An alternative synthetic method is o-nitration of benzyl chloride, but para nitration also occurs, reducing yield.

Figure 2:
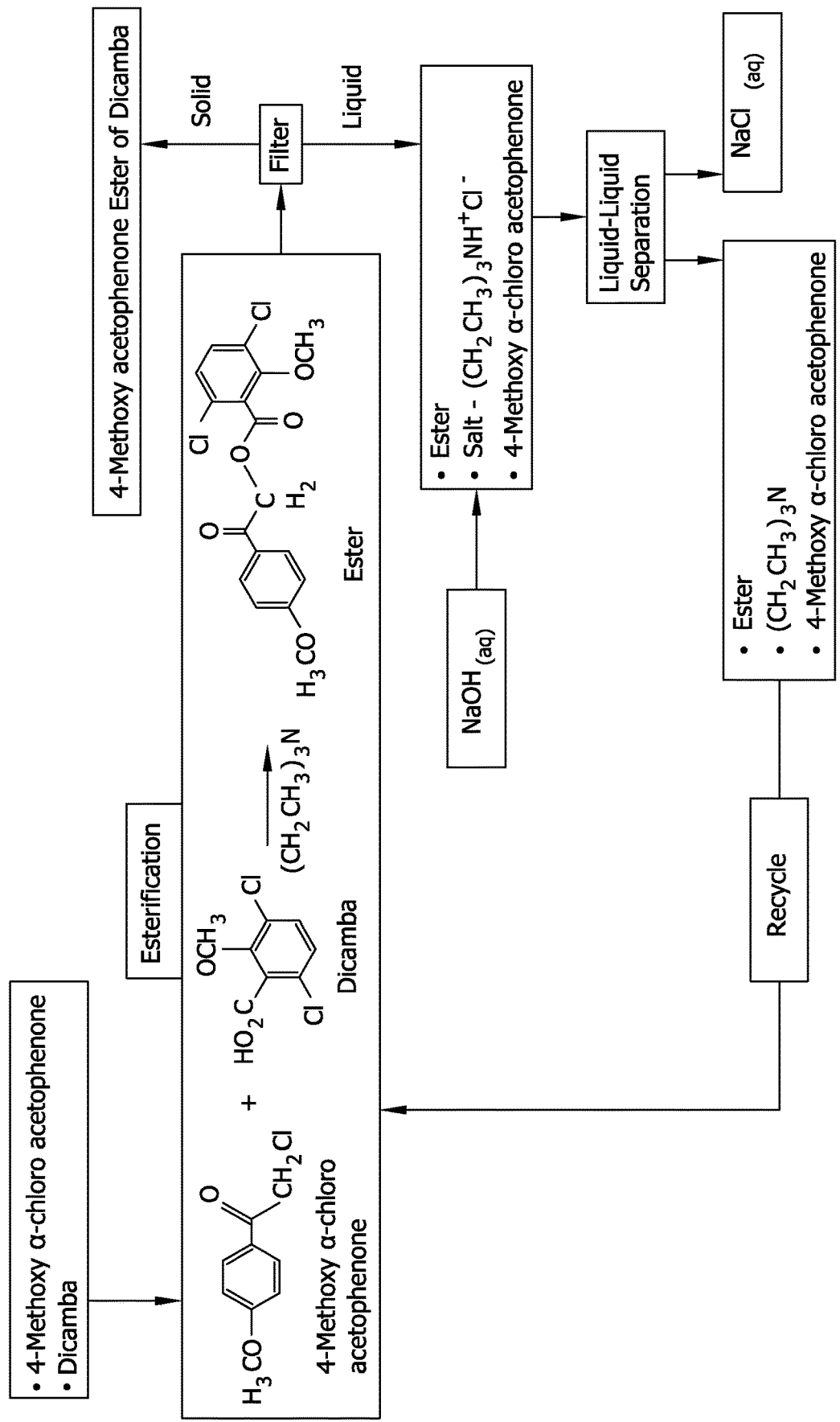
FIG. 2 is a schematic diagram showing a process for the preparation of 4-methyoxyphenacylmethyl esters of carboxylic acid agrochemicals.

A similar process can be used for the synthesis of the 4-methoxyphenacylmethyl esters 9 and 11. FIG. 2 illustrates this process for the 4-methoxyphenacylmethyl ester of dicamba (9). The primary difference is that 4-methoxy-α-chloroacetophenone is reacted with the carboxylate. As described in Example 8, this intermediate is conveniently prepared by Friedel Crafts acylation of anisole with chloroacetyl chloride. Either polar or non-polar hydrophobic solvents can be used.

Compositions

The esters of carboxylic acid agrochemicals described herein can be incorporated into useful agrochemical compositions. The esters are typically formulated as emulsifiable concentrates in organic solvents or as suspension concentrates. In several cases, the emulsifiable concentrate formulations of the dicamba esters provide equal or superior post-emergent control of broadleaf weeds as compared to the diglycolamine salt of dicamba, while greatly reducing dicamba volatility. In addition, improved pre-emergent control of broadleaf weeds can be achieved. The 2,4-D esters are significantly less soluble than dicamba esters, however, and are therefore typically formulated as suspension concentrates.

The compositions of the esters of carboxylic acid agrochemicals typically comprise one or more adjuvants. Typical adjuvants include, but are not limited to, solvents, surfactants, dispersants, antifreeze agents, antifoam agents, thickeners, bacteriostats, wetting agents, dyes, and combinations or mixtures thereof.

The solvent may comprise, for example, an aromatic hydrocarbon, monochlorobenzene, a naphthalenic organic solvent, isophorone, a carboxylic acid esters, a carboxylic acid diesters, a pyrrolidone, or a combination or mixture thereof.

Typical surfactants include nonionic surfactants and anionic surfactants, and typically a mixture of a nonionic surfactant and an anionic surfactant is used. Typical surfactants include, but are not limited to, ethoxylated alkyl alcohols, ethoxylated vegetable oils (e.g., ethoxylated castor oil), sulfonates (e.g., an alkylbenzene sulfonate calcium salt), or a combination or mixture thereof.

Dispersants that are typically used in the ester compositions include, but are not limited to lignosulfonate, sulfonated naphthalene-formaldehyde condensates, polymeric dispersants, or a combination or mixture thereof.

Typical antifreeze agents include, but are not limited to, propylene glycol, glycerin, or a combination or mixture thereof. The antifoam agent is typically a silicone antifoam agent, but other antifoam agents may also be used. Typical thickeners include, but are not limited to, xanthan gum, silicas, clays, or a combination or mixture thereof.

For most applications, particularly for fungicides and post-emergent herbicides, the esters are typically formulated as emulsifiable concentrates in agronomically acceptable organic solvents. The solvents typically have a flashpoint above 65° C. and reasonable solubility for the ester. The choice of solvent depends on various factors, including solubility, other actives that may be included in the formulation, and cost. Typical solvents include naphthalenic organic solvents, isophorone, monochlorobenzene, carboxylic acid esters and diesters, and pyrrolidones. The use of a mixture of a nonionic surfactant, preferably ethoxylated alkyl alcohols or vegetable oils and an anionic surfactant, preferably a sulfonate, is typical for the emulsification system. Typically, the ester is present at a concentration of from about 20 percent to about 50 percent in the emulsifiable concentrate formulations.

For pre-emergent herbicides, suspension concentrates are the typical formulations. Relatively high-melting and water-insoluble esters such as 2-nitrobenzyl, 4-methoxyphenacylmethyl, and 2-quinoxalinol esters (such as 1a, 9, and 13a, respectively, for dicamba) are typically formulated as suspension concentrates. The concentration of the ester particles in the suspension concentrate formulations is typically about 20 percent to about 50 percent.

Formulation of suspension concentrates of water-insoluble solids is known in the art and is discussed in T. F. Tadros, *Surfactants in Agrochemicals*, pp. 133-82 (1995). The photo-labile esters of the present invention are typically milled to a mean particle size of from about 0.5 to about 10 μm, more typically from about 1 to about 5 μm, for ease of formulation and in order to achieve efficient photo-release in the field. Bead milling is the preferred milling method.

The particles are typically dispersed using a polymeric dispersant. Such dispersants are known in the art and typically have a comb structure with hydrophobic backbone. Hydrophilic "teeth" protruding from the backbone can be anionic, such as maleic or acrylic acid salts or nonionic polyethylene oxide chains. Lignosulfonates are also typical dispersants and have similar properties. The formulations also typically include an antifreeze, for example propylene glycol or glycerin, as well as agents to raise viscosity such as xanthan gum, silicas or clays. Bacteriostats, antifoam agents, wetting agents, and dyes can also be added to the formulation as appropriate.

An alternative approach for the formulation of pre-emergent herbicides is micro-encapsulation of a solution of the photo-labile esters. In this case, high solubility esters such as 2 and 3 are typically used.

In various embodiments, the ester of a carboxylic acid agrochemical in the composition is an ester of dicamba or 2,4-D. The compositions may also comprise one or more additional agrochemicals. For example, the compositions may include a second agrochemical, such as a herbicide, a fungicide, an insecticide, a plant health agent, or a plant growth regulator. In some embodiments, the second agrochemical is an herbicide, such as glyphosate or an agronomically acceptable salt or ester thereof. Thus, for example, in some embodiments, the ester of a carboxylic acid agrochemical in the composition is an ester of dicamba, and the composition further comprises glyphosate or an agronomically acceptable salt or ester of glyphosate. In concentrate compositions, the glyphosate concentration is typically about 200 grams acid equivalent (a.e.)/L to about 400 grams a.e./L.

Determination of the Efficacy of Labile Esters

The efficacy of the photolabile esters can be assayed in vitro, or in greenhouse or field experiments. A useful in vitro assay for post-emergent activity involves photolysis of a dilute solution of the esters using simulated sunlight. This is conveniently achieved by photolysis of a solution of the ester in an organic solvent which is miscible with water and to which some water has been added. As described in the Examples, photolysis in acetonitrile or tetrahydrofuran containing 10% water by weight is effective. Low concentrations of the ester should be used so that the entire volume is exposed to sunlight. Since the maximum extinction coefficient of the typical esters above 220 nm is in the range of 1000-10,000 $M^{-1}$ $cm^{-1}$, a concentration of 0.1 mM is effective. Photolysis in a quartz tube exposed to simulated or actual sunlight is a typical protocol.

Suspension concentrate formulations of photo-labile esters can be screened in vitro for pre-emergent activity by a similar protocol. The suspension concentrate is typically diluted in water to a concentration of about 0.1 mM and photolyzed in a quartz tube. The samples are typically filtered before analysis.

The in vitro assay is a useful screening tool for esters and formulations and has proven generally effective at predicting greenhouse and field performance. Formulations of photo-labile esters of agrochemicals can be tested under greenhouse and field conditions under the same protocols used for other agrochemicals. However, as can be seen in the Examples below, esters such as the 4-methoxy and 4-n-butoxyphenacyl methyl esters (9 and 10 in the case of dicamba), whose absorbance spectrum is predominantly in the ultraviolet range, perform worse in the greenhouse than in in vitro or field experiments due to screening of ultraviolet light by the greenhouse roof.

Similar assays can be performed using water instead of organic solvents. Because of the limited solubility of some esters in water, the assay is performed at lower concentrations, e.g., 0.01 mM, as in the Examples below. This assay can identify photo-labile esters, but is more effective in characterizing hydrolytically labile esters and ranking their rates of hydrolysis.

Emulsifiable and suspension concentrates of 1a, 2, 9, 13a, 14, 17, 30a, 32a, and 36a have proven effective for the control of a number of broadleaf weeds in field testing, as have emulsifiable concentrates of 2 and 10. These weeds include *Sesbania macrocarpa*, morning glory, velvetleaf, Palmer amaranth, fat hen, and sicklepod.

Use of the Esters

The esters of carboxylic acid agrochemicals described herein can be used for the controlled release of the carboxylic acid agrochemical. In particular, in various embodiments, the invention relates to a method for the controlled release of a carboxylic acid agrochemical comprising exposing a photolabile ester of the carboxylic acid agrochemical to natural light (e.g., sunlight) or artificial light (e.g., incandescent or fluorescent light). In other embodiments, the invention relates to a method for the controlled release of a carboxylic acid agrochemical comprising exposing a hydrolytically labile ester of the carboxylic acid agrochemical to aqueous conditions (e.g., rainwater or irrigation water).

The esters of carboxylic acid herbicides described herein can also be used to control unwanted plants. In various embodiments, such methods comprise applying to the unwanted plants a herbicidal composition of the present invention comprising an ester of a carboxylic acid herbicide, for example, an ester of dicamba or 2,4-D. This may be accomplished, for example, by diluting, as necessary, the emulsion concentrate or suspension concentrate compositions described above to produce an application mixture, and applying the mixture to the unwanted plants. Such methods may further comprise applying a second herbicide to the unwanted plants, e.g., glyphosate or an agronomically acceptable salt or ester of glyphosate. In various embodiments, the carboxylic acid herbicide is dicamba and the second herbicide is glyphosate or an agronomically acceptable salt or ester thereof. The second herbicide can be applied to the unwanted plants before, concurrently with, or after application of the ester of a carboxylic acid herbicide. As described above, in some embodiments, the ester of a carboxylic acid herbicide and the second herbicide are combined into a single formulation prior to application to the unwanted plants.

Herbicidal Methods of Use

In herbicidal methods of the present invention, an application mixture (e.g., comprising a dilution of an ester of a carboxylic acid herbicide concentrate composition of the present invention), typically comprising from about 0.1 to about 50 g a.e./L herbicide, is formed and then applied to the foliage of a plant or plants or an area where plants are to be planted at an application rate sufficient to give a commercially acceptable rate of weed control. This application rate is usually expressed as amount of herbicide per unit area treated, e.g., grams acid equivalent per hectare (g a.e./ha). Depending on plant species and growing conditions, the period of time required to achieve a commercially acceptable rate of weed control can be as short as a week or as long as three weeks, four weeks or longer.

In some embodiments of the present invention, crop plants include, for example, corn, peanuts, potatoes, soybeans, canola, alfalfa, sugarcane, sugarbeets, peanuts, grain sorghum (milo), field beans, rice, sunflowers, wheat and cotton. In certain embodiments, the crop plant is selected from the group consisting of soybeans, cotton, peanuts, rice, wheat, canola, alfalfa, sugarcane, sorghum, and sunflowers. In various embodiments, the crop plant is selected from the group consisting of corn, soybean and cotton.

Crop plants include hybrids, inbreds, and transgenic or genetically modified plants having specific traits or combinations of traits including, without limitation, herbicide tolerance (e.g., resistance to carboxylic acid herbicides or other herbicides), *Bacillus thuringiensis* (Bt), high oil, high lysine, high starch, nutritional density, and drought resistance. In some embodiments, the crop plants are resistant to carboxylic acid herbicides (e.g., dicamba and/or 2,4-D) and/or other herbicides (e.g., glyphosate).

The application mixture comprising an ester of a carboxylic acid herbicide of the present invention can be applied prior to planting of crop plants that are susceptible to the carboxylic acid herbicide (e.g., dicamba-susceptible or 2,4-D-susceptible crop plants not having a trait providing tolerance to the carboxylic acid herbicide), such as, for example, from about two to about three weeks before planting. Crop plants that are not susceptible to the carboxylic acid herbicide (e.g., corn with respect to auxin herbicides), or transgenic or genetically modified crop plants having one or more traits providing tolerance to the carboxylic acid herbicide typically have no pre-planting restriction and the application mixture can be applied before planting such crops, at planting, pre-emergence (i.e., during the interval after planting of the crop plant up to, but not including, emergence of the crop plant) or post-emergence to the crop plants. For example, the application mixture comprising an ester of a carboxylic acid herbicide of the present invention can be applied at planting or post-emergence to the crop plants having a trait providing tolerance to the carboxylic acid herbicide to control weeds susceptible to the carboxylic acid herbicide in a field of the crop plants and/or adjacent to a field of the crop plants. In another example, in some embodiments of the present invention, an ester of a carboxylic acid herbicide of the present invention (e.g., an ester of dicamba or 2,4-D) is combined with glyphosate co-herbicide (or a salt or ester thereof) in the application mixture and the crop plant comprises a glyphosate-tolerant trait and the crop plant is further either (i) a plant species not susceptible to the carboxylic acid herbicide or (ii) comprises one or more traits providing tolerance to the carboxylic acid herbicide. Accordingly, such embodiments are useful to control (i) glyphosate susceptible plants and (ii) glyphosate resistant volunteer crop plants and/or weeds that are susceptible to the carboxylic acid herbicide growing in a field of (iii) crop plants tolerant to glyphosate and the carboxylic acid herbicide.

The application mixture comprising an ester of a carboxylic acid herbicide of the present invention can be applied pre-emergent or post-emergent to the weeds. Applying pre-emergent to the weeds generally refers applying the application mixture formulation at any time during an interval from about 40 days, from about 30, from about 25 days, from about 20 days, from about 15 days, from about 10 days, or from about 5 days pre-emergence of the weeds. Applying post-emergent to the weeds generally refers to applying the formulation at any time during an interval up to about 1 day after emergence, up to about 2 days after emergence, up to about 3 days after emergence, up to about 4 days after emergence, up to about 5 days after emergence, up to about 10 days after emergence, up to about 15 days after emergence, or up to about 20 days or longer after emergence of the weeds.

Weed control mentioned herein refers to any observable measure of control of plant growth, which can include one or more of the actions of (1) killing, (2) inhibiting growth, reproduction or proliferation, and (3) removing, destroying, or otherwise diminishing the occurrence and activity of plants. Weed control can be measured by any of the various methods known in the art. For example, weed control can be determined as a percentage as compared to untreated plants following a standard procedure wherein a visual assessment of plant mortality and growth reduction is made by one skilled in the art specially trained to make such assessments. In another control measurement method, control is defined as a mean plant weight reduction percentage between treated and untreated plants. In yet another control measurement method, control can be defined as the percentage of plants that fail to emerge following a pre-emergence herbicide application. A "commercially acceptable rate of weed control" varies with the weed species, degree of infestation, environmental conditions, and the associated crop plant. Typically, commercially effective weed control is defined as the destruction (or inhibition) of at least about 60%, about 65%, about 70%, about 75%, about 80%, or even at least about 85%, or even at least about 90%. Although it is generally preferable from a commercial viewpoint that about 80-85% or more of the weeds be destroyed, commercially acceptable weed control can occur at much lower destruction or inhibition levels, particularly with some very noxious, herbicide-resistant plants.

Novel Photo-Labile Protecting Groups

It has also been discovered that 2-quinoxalinol, maleic hydrazide, and phthalhydrazide moieties can be used as photolabile protecting groups. These moieties can be used in a method for the photo-release of a compound, wherein the method comprises exposing the compound to natural or artificial light, and the compound has been chemically modified to have an ester linkage to a photolabile protecting group having one of the following structures:

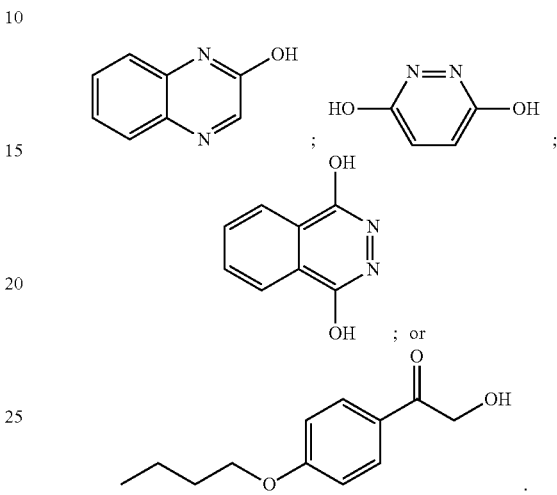

EXAMPLES

Example 1: Synthesis of the Acid Chloride of Dicamba

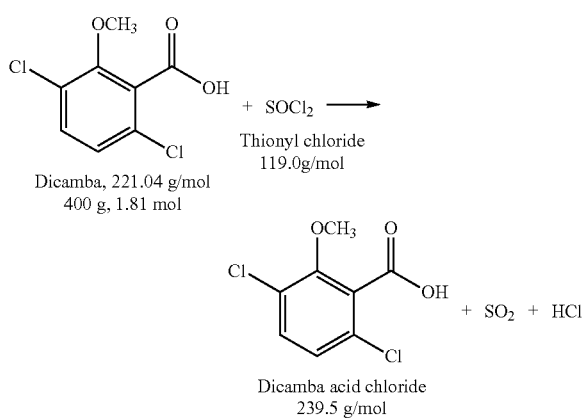

The reaction was performed in a 1-liter, 3-neck round-bottom flask with a mechanical stirrer. The flask was immersed in an oil bath that was initially at room temperature. In order to avoid loss of thionyl chloride from the reaction mixture, a water-cooled reflux condenser was attached to one neck of the flask and the other neck was plugged after dicamba addition was complete. 323 g of thionyl chloride was added to the flask and the oil bath heater was switched on with a setpoint of 80° C. 400 g of dicamba was added through one neck over about ten minutes. Evolution of HCl gas began during addition and subsided after about 90 minutes. The reaction was continued for about an hour after gas evolution subsided. About 475 g of crude liquid product was recovered.

Two batches of crude dicamba acid chloride were combined in a 2-liter flask that was connected to a vacuum distillation apparatus. The flask was insulated with glass wool and placed in a heating mantle. Heat was applied and a small (40 g) fore-run containing residual thionyl chloride was discarded. Vacuum was then applied and the product distilled at 210° C., 220 torr (29.3 kPa). 793 g of product was recovered.

Example 2: Synthesis of the Acid Chloride of 2,4-D

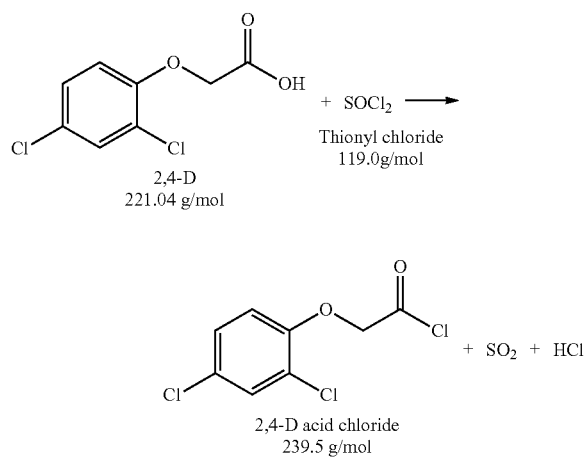

The reaction was performed in a mechanically stirred 1-liter, 3-neck round-bottom flask. One neck was connected to a 500 ml, 3-neck round-bottom flask through a latex tube connected to a glass gas dispersion tube immersed in 350 g of 50% NaOH plus 150 ml of water within the flask. The caustic flask was connected to vacuum through a tube with a pinchcock clamp to control the vacuum.

The reaction flask was immersed in an oil bath that was not heated initially. 350 g of thionyl chloride was added and heating and stirring initiated. 500 g of 2,4-D acid was added over 51 minutes.

The acid chloride was purified by vacuum distillation between 145° C. and 180° C. at pressure from 104 to 160 torr (13.9 to 21.3 kPa). 291 g of acid chloride was recovered from the distillation.

Example 3: Synthesis of the 2-Nitrobenzyl Ester of Dicamba, 1a, from the Alcohol

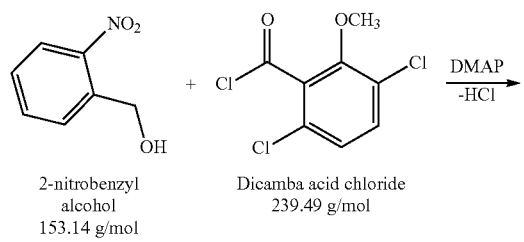

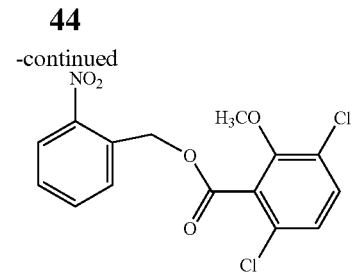

2-nitrobenzyl ester of dicamba
356.16 g/mol 76.6 g of 2-nitrobenzyl alcohol (0.5 mol, Aldrich), 52.6 g of triethylamine (0.52 mol), and 1.9 g of DMAP (Aldrich, 0.03 equiv.) were combined with 200 ml of $CH_2Cl_2$ in a 1-liter flask equipped with a stirbar. 119.7 g of dicamba acid chloride (0.5 mol). The mixture grew warm over five minutes but no refluxing occurred.

After stirring for four hours, 20 g of $NaHCO_3$ in 300 ml of water was added in order to extract the DMAP and most of the $((CH_2CH_3)_3NH^+)(Cl^-)$ as well as free dicamba. The organic phase was separated and dried over 10 g of $MgSO_4$. After filtration, the solvent was removed using a rotary evaporator. The product precipitated in the flask. It was scraped out, rinsed with $CH_2Cl_2$ and methyl-t-butyl ether and dried overnight at 80° C. under 24" Hg (81.3 kPa) vacuum with nitrogen purge. 110.2 g were recovered (62% yield).

Example 4: Synthesis of the 2-Nitrobenzyl Ester of Dicamba, 1a, Via 2-Nitrobenzyl Chloride

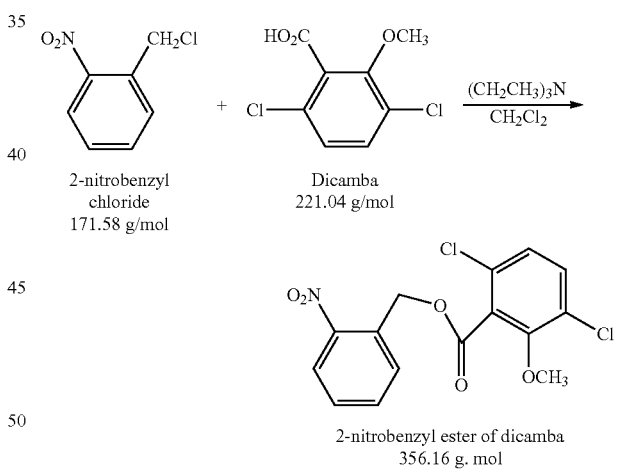

99 g of 2-nitrobenzyl chloride (0.58 mol, Acros), 127 g of dicamba (1.0 equiv), 58 g of triethylamine (1.0 equiv.), and 300 ml of $CH_2Cl_2$ were combined in a 1-liter round-bottom flask equipped with a stirbar. The flask was immersed in a 78° C. oil bath and refluxed for 18 hours with a water-cooled condenser attached. A white precipitate formed during this time $((CH_2CH_3)_3NH^+Cl^-)$.

The reaction mixture was extracted with a solution of 10 g of $NaHCO_3$ in 400 ml of water. The organic phase was isolated by decantation and a separatory funnel and dried over 15 g of $MgSO_4$. After filtration, the solvent was removed using a rotary evaporator. A heavy orange precipitate formed over about an hour. The solid was recovered by filtration and rinsed with methyl-t-butyl ether to remove the orange color. The off-white solid was dried over a weekend at 55° C. under 24" Hg (81.3 kPa) vacuum with nitrogen purge. 126.1 g was recovered (0.35 mol, 61%).

Compound 1c can be synthesized by methods similar to those described above for 1a, except that 3-nitrobenzyl alcohol or 3-nitrobenzyl chloride is used as the starting material.

Example 5: Synthesis of the 6-Nitroveratryl Alcohol Ester of Dicamba, 1b

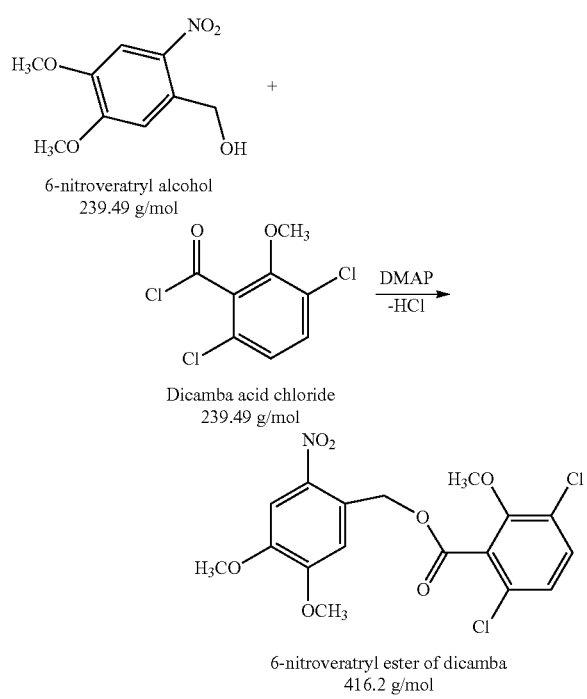

10.7 g of 6-nitroveratryl alcohol (0.050 mol, Alfa Aesar), 12.0 g of dicamba acid chloride (1.0 equiv.), 1.0 equiv of triethylamine, 0.05 equiv. of DMAP and 285 g of CHCl$_3$ were combined in an Erlenmeyer flask. Dissolution of the alcohol was incomplete. The mixture was stirred for 70 hours, wrapped in foil.

After reaction, solution of 1.2 equivalents (6.3 g) of Na$_2$CO$_3$ in 100 ml of water was added to the mixture in order to hydrolyze unreacted dicamba acid chloride and extract it into water. The mixture was stirred for 30-60 minutes and the organic (lower) layer was removed and then washed with 5 g of NaHCO$_3$ in 50 ml of water using a separatory funnel. The CHCl$_3$ solutions stirred over 10 g of MgSO$_4$ in order to remove residual water. The MgSO$_4$ was filtered and the solvent removed on a rotary evaporator.

The concentrate initially gave an oil, but a solid formed upon standing at room temperature. The suspension was rinsed into a fritted Buchner funnel using methyl-t-butyl ether, rinsed with more methyl-t-butyl ether, and transferred to a bottle. 13.0 g of a fine solid was recovered. The dark yellow filtrate was discarded.

The solid was dried under vacuum with nitrogen purge at 60° C. for three hours. 11.6 g of a fine yellow powder was obtained after drying (56% of theoretical).

Example 6: Synthesis of the 2-Nitrophenethyl Ester of Dicamba, 2

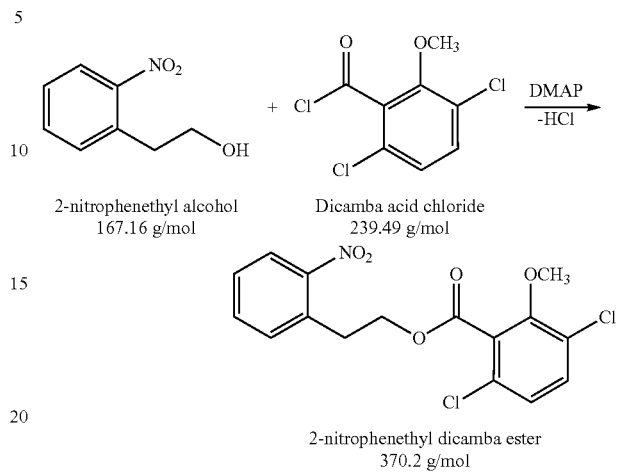

49.8 g of 2-nitrophenethyl alcohol (Aldrich, 0.30 mol), 33.1 g of triethylamine (1.1 equiv.), 74.9 g of dicamba acid chloride (1.05 equiv.), 1.82 g of DMAP (5 mol %), and 150 ml of CH$_2$Cl$_2$ were combined in a 500-ml round-bottom flask equipped with a stirbar and stirred overnight at room temperature. Mild heat evolution was noted initially, but the solution did not boil.

After 15 hours, a heavy precipitate was observed. 15 g of Na$_2$CO$_3$ in 200 ml of water was added to extract the precipitate (HN(CH$_2$CH$_3$)$_3$$^+$Cl$^-$) and hydrolyze residual dicamba acid chloride. The aqueous layer was separated and the organic layer washed with 12 g of NaHCO$_3$ in 150 ml of water to extract DMAP and residual organic salts. The organic layer was then dried over 10 g of MgSO$_4$, filtered, and concentrated on a rotary evaporator. Crystallization occurred on cooling. The product was recovered by filtration, rinsed with methyl-t-butyl ether, and dried under 24" Hg (81.3 kPa) vacuum at 45° C. with nitrogen purge for two hours. 66 g of a light yellow crystalline solid was recovered (0.18 mol, 60% yield).

Example 7: Synthesis of the 2-(2-Nitrobenzoxy)Ethanol Ester of Dicamba, 4

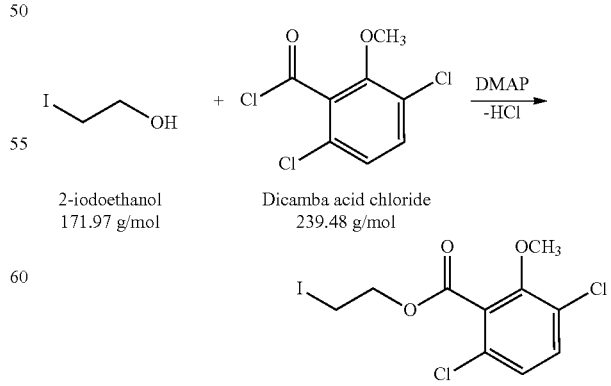

47

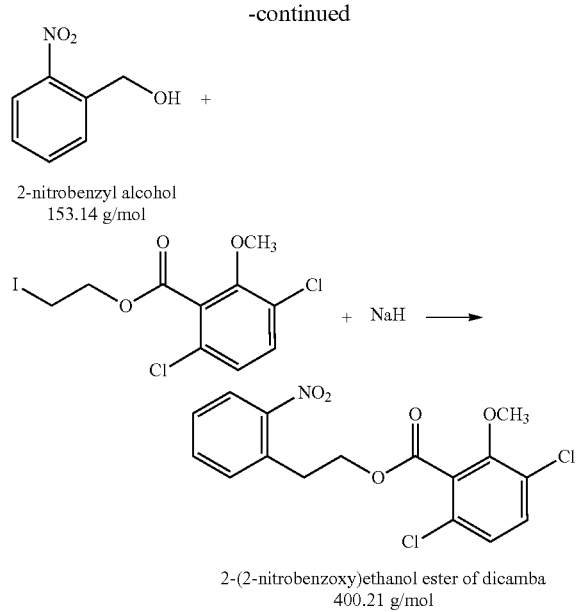

2-nitrobenzyl alcohol
153.14 g/mol 2-(2-nitrobenzoxy)ethanol ester of dicamba
400.21 g/mol 20.64 g of 2-iodoethanol (0.12 mol, Aldrich), 13.4 g of triethylamine (1.1 equiv.), 28.7 g of dicamba acid chloride (1.0 equiv.), 0.73 g of DMAP (0.05 equiv.), and 50 ml of dry $CH_2Cl_2$ were combined in a round-bottom flask equipped with a stirbar. Mild heat evolution was noted immediately after adding the last component, DMAP.

After stirring for three hours, a solution of 5 g of $Na_2CO_3$ in 70 ml of water was added to extract $(CH_2CH_3)_3NH^+Cl^-$ and hydrolyze residual dicamba acid chloride. After stirring for an hour, 5 g of $NaHCO_3$ in 70 ml of water was added and stirred briefly to extract DMAP. The yellow organic phase was isolated using a separatory funnel and dried over $MgSO_4$. After filtration, the solvent was removed using a rotary evaporator to a light orange low-viscosity residue (43.6 g, 97% of theoretical).

The residue was dissolved in 50 ml of $CH_2Cl_2$ in a round-bottom flask. 5.8 g of a 60% suspension of NaH in mineral oil was added. (1.2 equiv. with respect to 2-iodoethanol used in first step, Rohm and Haas via Aldrich). A solution of 18.4 g of 2-nitrobenzyl alcohol (1.0 equiv., Aldrich) in 100 ml of $CH_2Cl_2$ was added over 26 minutes with a dropping funnel. Light hydrogen evolution was observed initially. After five minutes, a heavy precipitate formed, hydrogen evolution accelerated significantly, and the solution grew warm but never refluxed. From this time forward, the solution began to darken.

The mixture was stirred for four hours. Then 8 g of $NaHCO_3$ in 100 ml of water was added to neutralize residual NaH. The mixture was then poured into a flask containing 450 ml of water in order to extract NaI and separate the phases. More water had to be used to isolate the organic layer because both phases were dark in color. Adding water lightened the color of the aqueous phase. The organic phase was dried over $MgSO_4$, filtered, and concentrated on a rotary evaporator. Diethyl ether was added, leading to the formation of a small amount of a gummy precipitate. The product was filtered and the filtrate again concentrated on a rotary evaporator. 30.0 g of a red-purple liquid was collected (62% of theoretical).

48

Example 8: Synthesis of p-methoxy-α-chloroacetophenone and the 4-methoxyphenacyl methyl ester of dicamba, 9

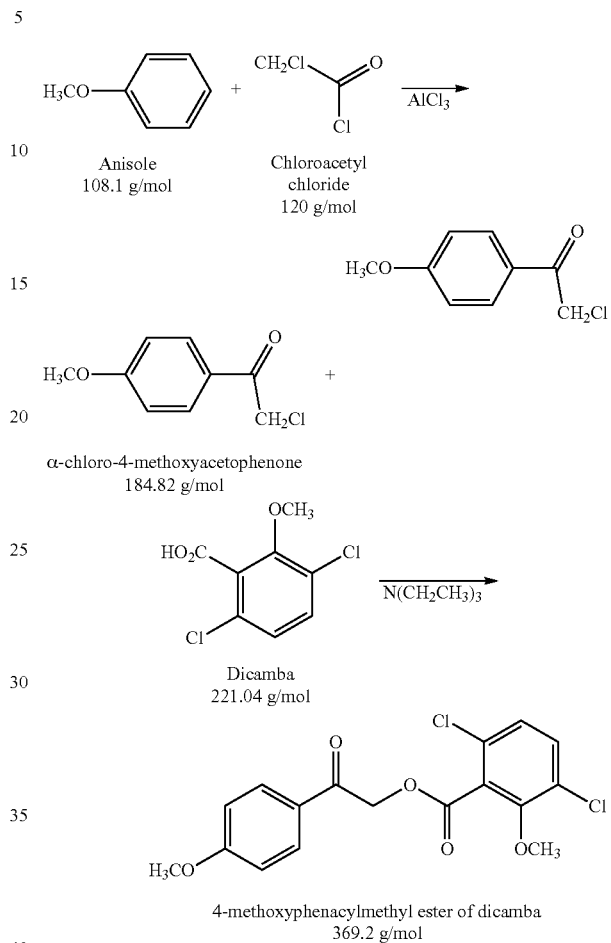

Anisole
108.1 g/mol

Chloroacetyl chloride
120 g/mol

α-chloro-4-methoxyacetophenone
184.82 g/mol

Dicamba
221.04 g/mol 4-methoxyphenacylmethyl ester of dicamba
369.2 g/mol 194.6 g of anisole (1.8 mol, anhydrous, Sigma), 169.4 g of chloroacetyl chloride (1.5 mol, Sigma) and 250 g of $CS_2$ were combined in a 1-liter flanged reaction vessel with a rounded bottom. The mixture was mechanically stirred and 227 g (1.7 mol) of $AlCl_3$ was added over 12 minutes.

After two hours of reaction, the reaction mixture was carefully poured out into a 4-liter beaker containing 1.0 kg of ice and 650 g of concentrated hydrochloric acid. The mixture was agitated with a spatula. A light-colored precipitate formed as the red color was discharged. 200 ml of $CHCl_3$ was used to rinse the reaction vessel and added to the beaker, forming a separate organic layer on the bottom. The aqueous layer was mostly decanted and the mixture was filtered. The water was immediately decanted from the filtrate. More product precipitated in the filter flask and it was recovered in the same Buchner funnel as the original precipitate. The precipitate was rinsed with ethyl acetate and dried overnight at 80° C. under 24" Hg (81.3 kPa) vacuum with nitrogen purge. 220 g were recovered.

150 g (0.81 mol) p-methoxy-α-chloroacetophenone prepared as above was added to a 1-liter round-bottom flask along with 197 g of dicamba acid (1.1 equiv), 90 g of triethylamine (1.1 equiv.) and 400 ml of THF. The mixture was refluxed in a 70° C. oil bath with a reflux condenser attached. Substantial solid formation was visible within 10 minutes and the solution had set up, freezing the stirbar, within 20 minutes.

After 3.7 hours of stirring, the contents of the flask were poured into a beaker containing a solution of 30 g of NaHCO$_3$ in 600 ml of water. The flask was rinsed out with a little more water which was added to the beaker. A dark lower organic layer formed along with a light-colored aqueous layer. After standing for about ten minutes, a heavy white precipitate formed.

The mixture was given at least an hour to complete precipitation. It was then recovered by filtration, rinsed with methyl-t-butyl ether, and dried overnight at 80° C. under 24" Hg (81.3 kPa) vacuum with nitrogen purge. 252 g were recovered (83%).

Example 9: Synthesis of the p-n-Butoxyphenacylmethyl Ester of Dicamba, 10

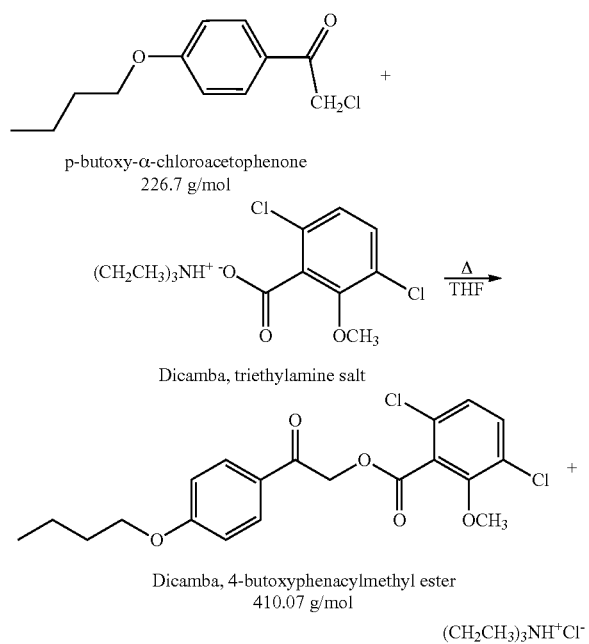

100 g of n-butyl phenyl ether (0.68 mol, Aldrich), 73.2 g of chloroacetyl chloride (0.95 equiv), and 200 g of CS$_2$ were combined in a mechanically-stirred round-bottom reaction vessel equipped with a water-cooled condenser. 100 g of AlCl$_3$ (1.1 equiv.) was added over 10 minutes with stirring. Refluxing began after 3 minutes and subsided after 20 minutes. Stirring was continued for a total of two hours.

The reaction mixture was carefully poured out onto a mixture of 900 g of ice and 400 g of conc. HCl. The mixture was stirred with a spatula to ensure complete hydrolysis, then extracted twice with diethyl ether (250 and 150 ml). The diethyl ether extracts were stirred for 30 minutes with 100 g of conc. HCl. The ether layer was then separated and stirred with a solution of 15 g of Na$_2$CO$_3$ in 200 ml of water to remove HCl and residual chloroacetic acid. It was again separated and dried over 20 g of MgSO$_4$.

110.1 g of liquid product was recovered and combined with 1.0 equivalent of triethylamine and dicamba in THF in a round-bottom flask equipped with a reflux condenser. The mixture was stirred for 15 hours in a 75° C. oil bath. A solution of 15 g of NaHCO$_3$ in 300 ml of water was added and stirred briefly, leading to phase separation.

The dark organic phase was separated and washed with 300 ml of water. Roughly 100 ml each of CH$_2$Cl$_2$ and water were added and stirred to improve phase separation. The organic layer was isolated and the solvent removed using a rotary evaporator. 179 g were recovered (0.44 mol, 90% yield if pure).

Example 10: Synthesis of the 2-Quinoxalinol Ester of Dicamba, 13a

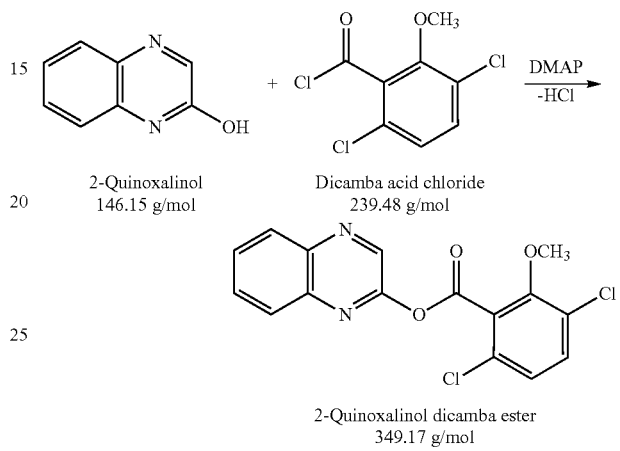

73.1 g of 2-quinoxalinol (0.5 mol, Aldrich), 1.2 g of DMAP (0.02 equiv.), 120 g of dicamba acid chloride (1.0 equiv.), 53.1 g of triethylamine (1.0 equiv.) and 300 ml of anhydrous CH$_2$Cl$_2$ were combined in a 1-liter round-bottom flask. A vigorous reaction ensued, with refluxing occurring within about two minutes and the formation of a yellow color. Refluxing subsided after about 20 minutes. The solubility of 2-quinoxalinol was initially poor, but after 30 minutes the product appeared to be dissolved and the white suspended solid appeared to be (CH$_3$CH$_2$)$_3$NH$^+$Cl$^-$.

The reaction mixture was stirred for three hours. 15 g of NaHCO$_3$ in 300 ml of water was then added to extract (CH$_3$CH$_2$)$_3$NH$^+$Cl$^-$, DMAP, and unreacted dicamba acid chloride. The organic layer was isolated and dried over 35 g of MgSO$_4$. The solution was filtered and the solvent removed with a rotary evaporator. The solid was recovered by filtration, rinsed with ethyl acetate and diethyl ether to remove the orange color, and dried at 60° C. under 24" Hg (81.3 kPa) vacuum with hydrogen purge. 116.0 g of a colorless, crystalline solid was recovered (0.33 mol, 66% yield).

Compound 13b can be synthesized in a similar manner, using 3-methyl-2-quinoxalinol as the starting material.

Example 11: Synthesis of the 2-Hydroxypyridine Ester of Dicamba, 14

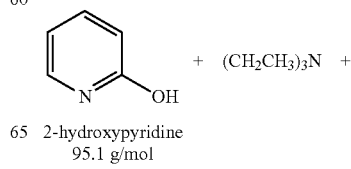

2-hydroxypyridine
95.1 g/mol

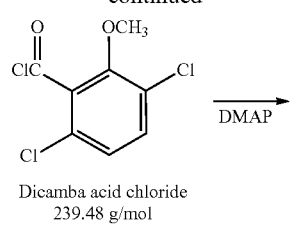

Dicamba acid chloride
239.48 g/mol

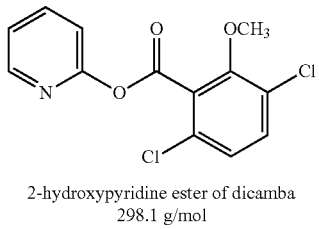

2-hydroxypyridine ester of dicamba
298.1 g/mol 52.1 g of 2-hydroxypyridine (0.55 mol, Alfa Aesar), 55 g of triethylamine (1.0 equiv.), 2.0 g of DMAP (3 mol percent), and 131.1 g of dicamba acid chloride (1.0 equiv.) were combined with 100 ml of $CH_2Cl_2$ in a round-bottom flask equipped with a stirbar. The solution immediately took on a yellow color and boiled vigorously within a minute as heavy white solid precipitated, freezing the stirbar. Boiling subsided within five minutes.

The mixture was held without heating for two hours and then added to a solution of 35 g of $NaHCO_3$ in 500 ml of water to extract unreacted dicamba, DMAP, and $(CH_2CH_3)_3NH^+Cl^-$. The organic layer was separated and concentrated on a rotary evaporator without vacuum. Crystallization of a yellow solid began immediately afterwards. The solid was recovered by filtration, rinsed with acetone and methyl-t-butyl ether and dried overnight at 80° C. under 24"Hg (81.3 kPa) vacuum with nitrogen purge. 105.3 g were recovered (64% yield).

Example 12: Synthesis of the Maleic Hydrazide Diester of Dicamba, 17

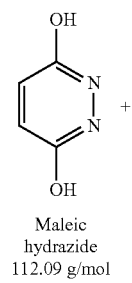

Maleic
hydrazide
112.09 g/mol

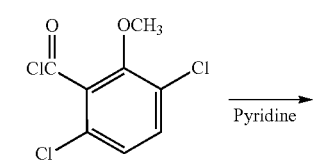

Dicamba acid chloride
239.48 g/mol

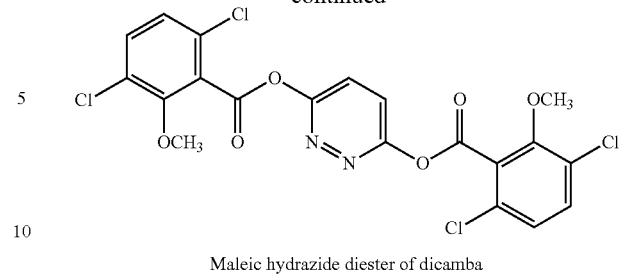

Maleic hydrazide diester of dicamba
518.13 g/mol 11.2 g of maleic hydrazide (0.10 mol, Sigma Aldrich) and 54 g of dicamba acid chloride (2.2 equiv) were combined with 100 mL of pyridine in a round-bottom flask equipped with a stirbar. The reaction mixture was initially lemon yellow with white suspended solid. Heat evolution occurred immediately.

The reaction mixture was stirred for four hours. A solution of 30 g of $Na_2CO_3$ in 300 ml of water was added in order to neutralize any hydrochloride salt of the product and extract pyridine into the aqueous phase. A liquid lower red phase separated initially but a fine white solid crystallized beginning in about half an hour. The mixture was stirred overnight to complete crystallization. The solid recovered by filtration and rinsed with water and methyl-t-butyl ether. The solid was then dried at 90° C. under 24" Hg (81.3 kPa) vacuum with nitrogen purge. Yields varied from 68-84%.

Example 13: Synthesis of the Phthalhydrazide Diester of Dicamba, 18

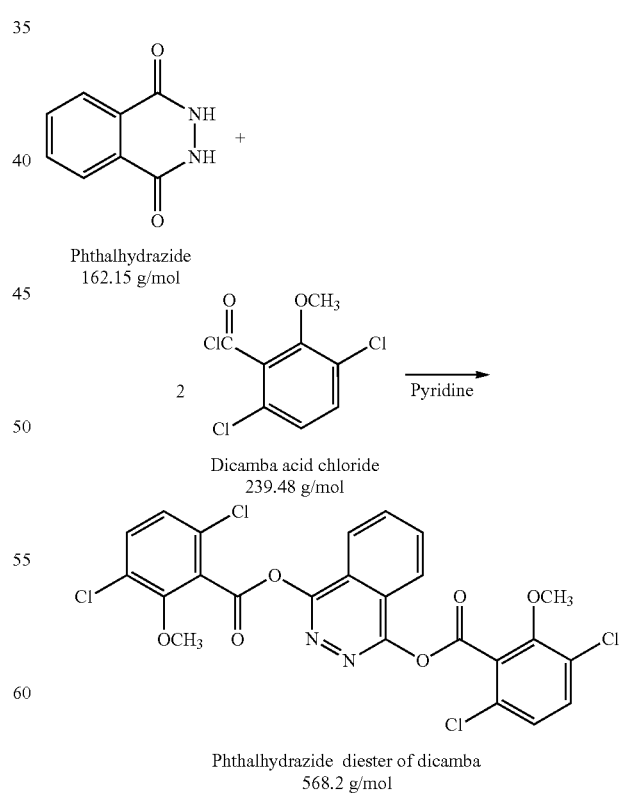

Phthalhydrazide diester of dicamba
568.2 g/mol 8.3 g of phthalhydrazide (0.05 mol, Sigma Aldrich) and 27 g of dicamba acid chloride (2.2 equiv.) were combined with 50 ml of pyridine in a round-bottom flask equipped with a stirbar. Heat evolution occurred immediately along with the formation of a homogeneous orange solution. A precipitate began to form after 11 minutes.

The reaction mixture was stirred overnight (17 hours) and added to a solution of 15 g of NaCO₃ in 120 ml of water to neutralize any hydrochloride salt of the product and extract pyridine into the aqueous phase. Heavy precipitate persisted. The mixture was stirred for two hours, then filtered. The solid was rinsed with water and methyl-t-butyl ether and dried at 90° C. under 24" Hg (81.3 kPa) vacuum with nitrogen purge. 18.7 g of the diester, a light yellow powder, were recovered (66% of theoretical).

Example 14: Synthesis of the 2-Nitrobenzyl Ester of 2,4-D, 5a

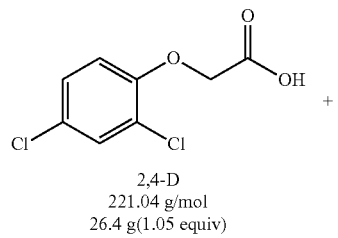

2,4-D
221.04 g/mol
26.4 g(1.05 equiv)

+

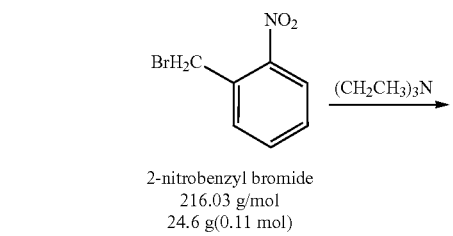

2-nitrobenzyl bromide
216.03 g/mol
24.6 g(0.11 mol)

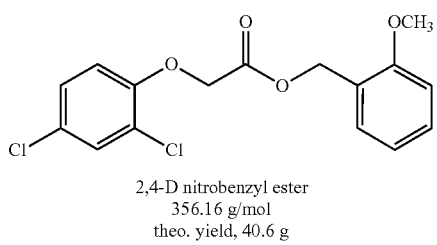

2,4-D nitrobenzyl ester
356.16 g/mol
theo. yield, 40.6 g 26.4 g of 2-nitrobenzyl bromide (0.11 mol, Acros) was combined with 26.4 g of 2,4-D (1.05 equiv), 11.5 g of triethylamine (1.0 equiv.) and 100 ml of dry THF in a 250-ml round-bottom flask. The mixture was refluxed overnight in a 73° C. oil bath with a water-cooled condenser attached, then poured into a flask containing 15 g of NaHCO₃ in 150 ml of water. A white solid precipitated.

The solid was recovered by filtration, rinsed with deionized water, and dried under 24" Hg (81.3 kPa) vacuum with nitrogen purge at 85° C. 40.4 g were recovered (nearly quantitative).

Example 15: Synthesis of the 4-Methoxy-Phenacylmethyl Ester of 2,4-D, 11

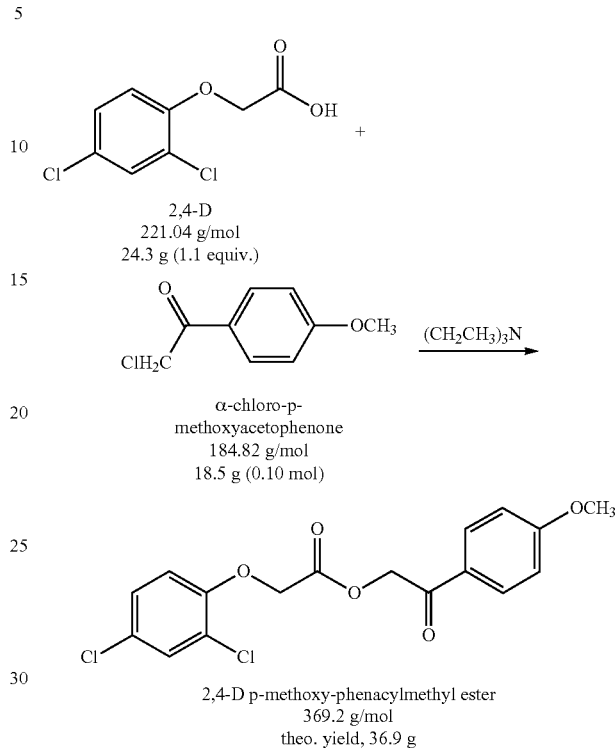

18.5 g of p-methoxy-α-chloroacetophenone from Example 8 was added to a 500 ml round-bottom flask equipped with a stirbar along with 24.3 g of 2,4-D (1.1 equiv), 11.1 g of triethylamine (1.1 equiv.), and 150 ml of THF. A water-cooled reflux condenser was attached and the flask was immersed in a 80° C. oil bath.

The mixture was refluxed for 19 hours with stirring at which time a finely divided white solid was seen in the flask, a mixture of product and (CH₂CH₃)₃NH⁺Cl⁻. 10 of NaHCO₃ in 150 ml of water was then added to dissolve the (CH₂CH₃)₃NH⁺Cl⁻ and extract unreacted 2,4-D and triethylamine. A little CO₂ bubbling was seen, suggesting that some triethylamine had volatilized out. The suspension was filtered, recovering a white product. The solid was rinsed with diethyl ether and dried at 80° C. under 24" Hg (81.3 kPa) vacuum with nitrogen purge. 17.7 g of white solid was recovered (48%).

Example 16: Synthesis of the 2-Quinoxalinol Ester of 2,4-D, 15a

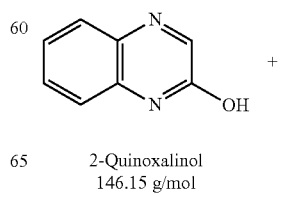

2-Quinoxalinol
146.15 g/mol

+

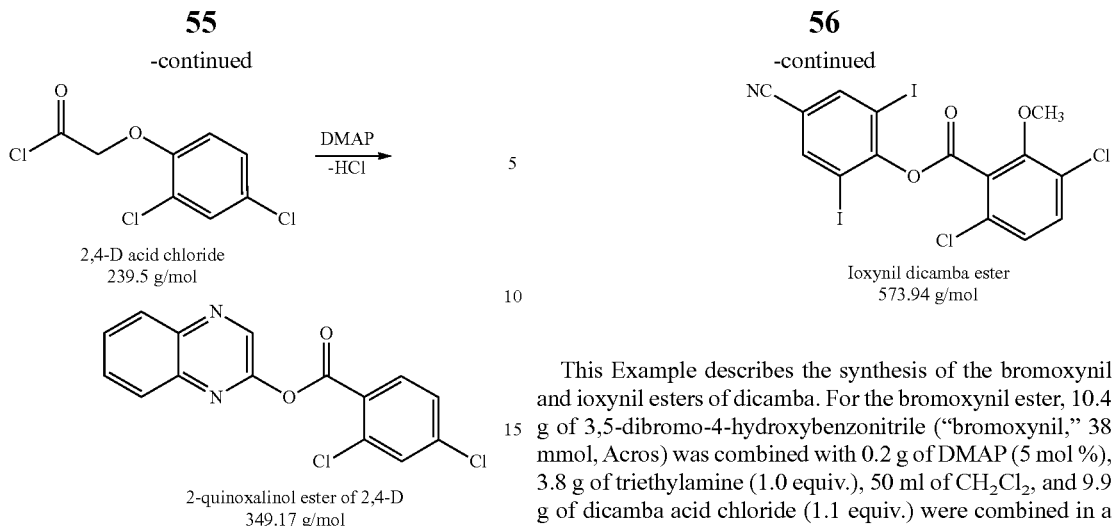

29.2 g of 2-quinoxalinol (Aldrich), 20.2 g of triethylamine (1.0 equiv.), 0.73 g of DMAP (0.03 equiv.), 55.1 g of 2,4-D acid chloride (1.15 equiv), and 200 ml of dry $CH_2Cl_2$ were combined in a 500-ml round-bottom flask equipped with a stirbar. Dissolution of the 2-quinoxalinol was only partial. Mild heat evolution was observed immediately.

After 16 hours, the solution was still heterogeneous. 10 g of $NaHCO_3$ in 150 ml of water was added and stirred in order to dissolve $(CH_2CH_3)_3NH^+Cl^-$ and extract dicamba and DMAP. The off-white solid was recovered by filtration, rinsed with water, methanol, and diethyl ether, and dried under 24" Hg (81.3 kPa) vacuum with nitrogen purge at 80° C. 33.6 g were recovered (45% of theoretical).

Example 17: Synthesis of the Bromoxynil and Ioxynil Esters of Dicamba, 23b and 23c

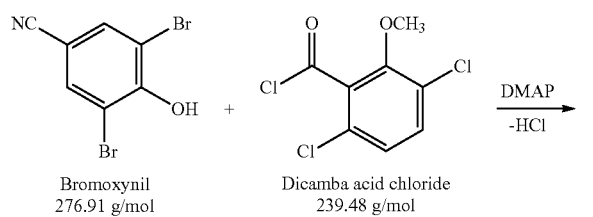

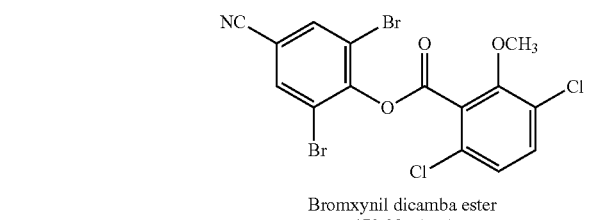

This Example describes the synthesis of the bromoxynil and ioxynil esters of dicamba. For the bromoxynil ester, 10.4 g of 3,5-dibromo-4-hydroxybenzonitrile ("bromoxynil," 38 mmol, Acros) was combined with 0.2 g of DMAP (5 mol %), 3.8 g of triethylamine (1.0 equiv.), 50 ml of $CH_2Cl_2$, and 9.9 g of dicamba acid chloride (1.1 equiv.) were combined in a round-bottom flask equipped with a stirbar. The mixture was stirred at room temperature for 4.5 hours before, a solution of 4 g of $NaHCO_3$ in 60 ml of water was added to hydrolyze residual dicamba acid chloride and extract $(CH_2CH_3)_3NH^+Cl^-$, dicamba, and DMAP. After stirring for an hour, a fine white solid was isolated by filtration, rinsed with methyl-t-butyl ether, and dried overnight at 70° C. under 24" Hg (81.3 kPa) vacuum with nitrogen purge. 11.65 g of a pure white powder was recovered (65% of theoretical).

The ioxynil ester was prepared using the same procedure, combining 11.8 g of 3,5-diiodo-4-hydroxybenzonitrile ("ioxynil," 32 mmol, Acros), 0.2 g of DMAP (5 mol %), 3.2 g of triethylamine (1.0 equiv.), 50 ml of $CH_2Cl_2$, and 8.4 g of dicamba acid chloride (1.1 equiv.). The mixture was stirred for 22 hours before adding a solution of 4 g of $NaHCO_3$ in 60 ml of water. Considerable suspended solid was present which was recovered by filtration after an hour of stirring. The solid was dried for five hours at 80° C. under 24" Hg (81.3 kPa) vacuum with nitrogen purge. 11.7 g of a pure white fine solid was recovered (64% of theoretical).

The chloroxynil ester of dicamba (23a) can be prepared in a similar manner, using 3,5-dichloro-4-hydroxybenzonitrile ("chloroxynil") as the starting material.

Example 18: Synthesis of the 4-Methoxybenzyl Ester of Dicamba, 29a

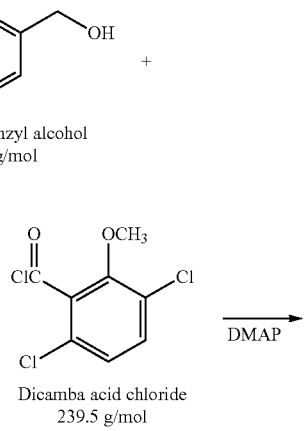

-continued

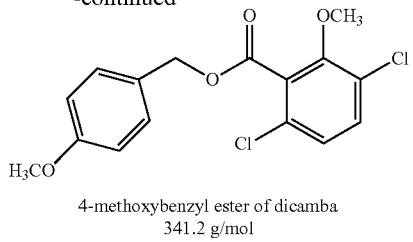

4-methoxybenzyl ester of dicamba
341.2 g/mol 138.2 g of 4-methoxybenzyl alcohol (1.0 mol, Aldrich) was combined with 102 g of triethylamine (1.0 equiv.), 2.4 g of DMAP (2 mol %), 200 ml of acetonitrile, and 264 g of dicamba acid chloride (1.1 equiv.). The mixture turned dark red and grew very hot, but did not boil. Heavy precipitate had accumulated within an hour. The mixture was stirred for 3.6 hours and then added to 60 g of $NaHCO_3$ in 800 ml of water in order to hydrolyze and extract residual dicamba acid chloride and extract acetonitrile, DMAP and $(CH_2CH_3)_3NH^+Cl^-$. The product separated as a dark lower layer. The aqueous layer was decanted and washed with 500 ml of water. It was then concentrated on a rotary evaporator. 358.1 g of product was recovered as a low-viscosity liquid (105% of theoretical).

Example 19: Synthesis of the 4-Methoxyphenol Ester of Dicamba, 30a

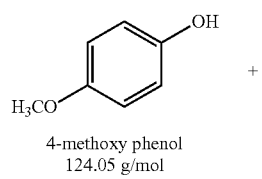

4-methoxy phenol
124.05 g/mol

+

-continued

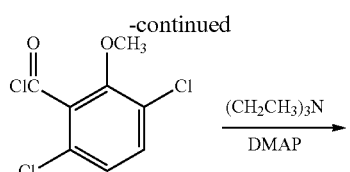

Dicamba acid chloride
239.48 g/mol

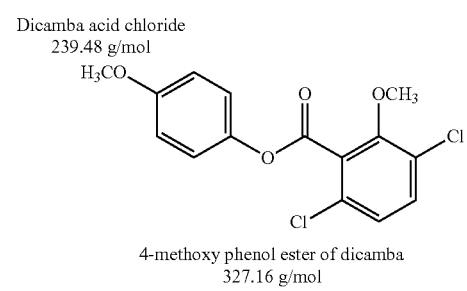

4-methoxy phenol ester of dicamba
327.16 g/mol 112 g of 4-methoxyphenol (0.9 mol, Alfa Aesar), 91 g of triethylamine (1.0 equiv.), 1.1 g of DMAP (3 mol percent), and 216 g of dicamba acid chloride (1.0 equiv) were combined with 600 ml of $CH_2Cl_2$ in a 2-liter Erlenmeyer flask equipped with a stirbar. Boiling and formation of a white precipitate began. After 11 hours of stirring, 40 g of $NaHCO_3$ in 800 ml of water was added to extract $(CH_2CH_3)_3NH^+Cl^-$ and DMAP. The organic phase was isolated using a separatory funnel and the solvent removed with a rotary evaporator. The product was poured into a beaker containing 100 ml of hexane. Crystallization of the product as a white solid began upon cooling. The solid was recovered in a Buchner funnel, washed with hexane, and dried at 50° C. under 24" Hg (81.3 kPa) vacuum with nitrogen purge. 280 g of product was recovered as a fine white crystalline powder (95% of theory).

Example 20: Baylis-Hillman Condensation of Ethyl Acrylate with Ortho, Meta, and Para-Nitrobenzaldehyde and Synthesis of the Dicamba Esters, 31a, 31b, and 31c

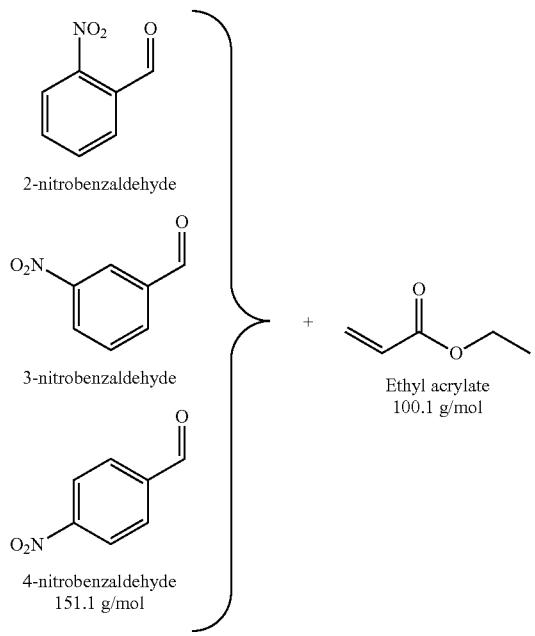

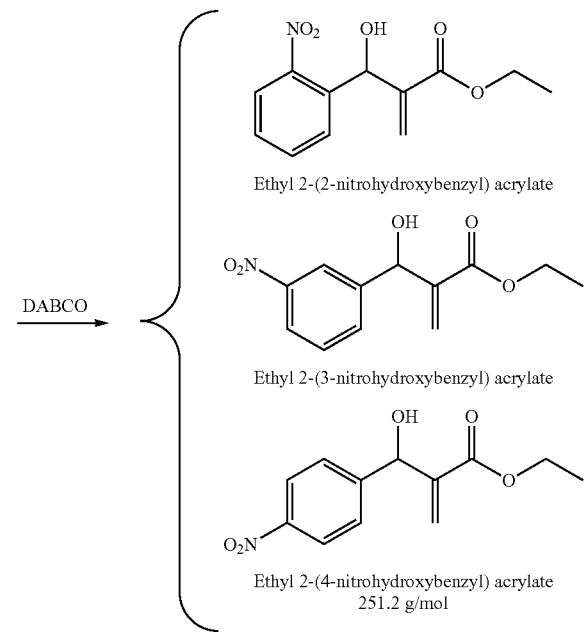

100 g of the nitrobenzaldehyde (0.66 mol, Alfa Aesar) was combined with 80 g of ethyl acrylate (1.2 equiv., Alfa Aesar), 4.5 g of DABCO (6 mol %), and ethanol in a 500-ml flask equipped with a stirbar. The mixtures were stirred for six days. 20 g of $NaHCO_3$ in 250 ml of water was added in order to neutralize and extract DABCO along with most of the solvent and acrylate. A lower organic layer separated which was isolated, dried over 25 g of $MgSO_4$, and concentrated on a rotary evaporator. The products were yellow-orange liquids. Conversion of the aldehydes was complete, but a small amount of residual ethyl acrylate was seen by $^1H$ NMR.

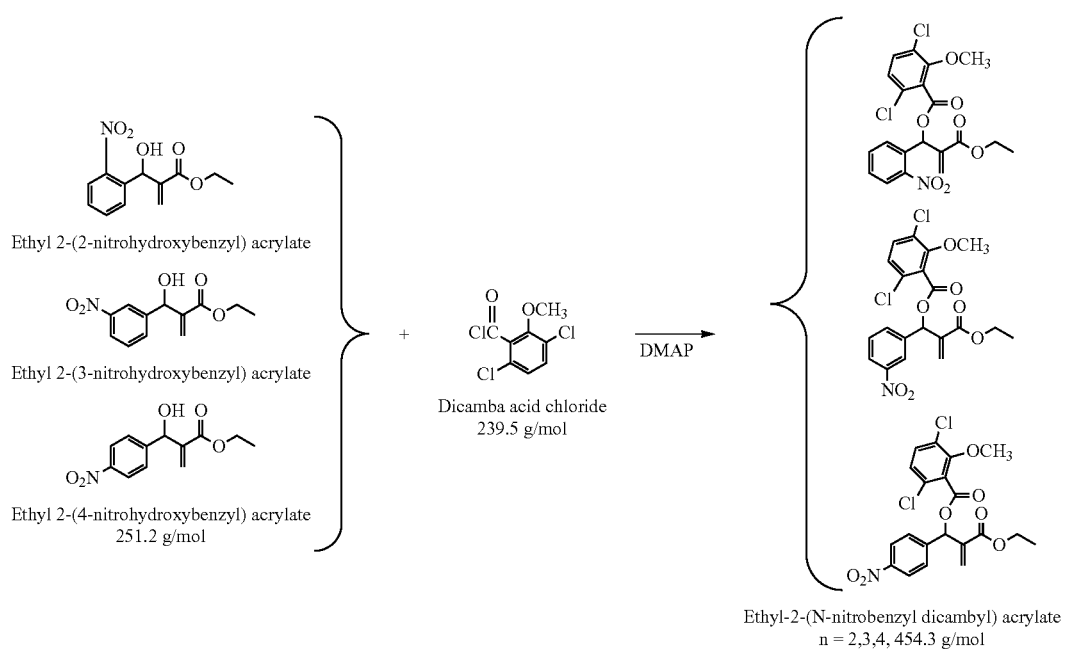

100 g of the three products (0.40 mol) was combined with 1.5 g of DMAP (3 mol %), 40 g of $(CH_2CH_3)_3N$ (1.0 equiv.), 100 ml of $CH_2Cl_2$, and 95 g of dicamba acid chloride (1.0 equiv). Mild heat evolution was observed for the ortho isomer, while the meta and para isomers exhibited mild boiling. A precipitate formed in all three flasks within 30 minutes. The mixtures were stirred overnight (19 hours) at which point the three reaction mixtures were gelatinous. 20 g of $NaHCO_3$ in 500 ml of water was added and the aqueous layer was decanted. Another 500 ml of water added to extract residual $(CH_2CH_3)_3NH^+Cl^-$ and DMAP. The organic layer was isolated and concentrated on a rotary evaporator. The products were viscous liquids. $^1H$ NMR and FTIR confirmed the identity and purity of the three esters.

Example 21: Synthesis of Dicamba Ester 32a Via Michael Addition of Methyl Vinyl Ketone to Maleic Hydrazide

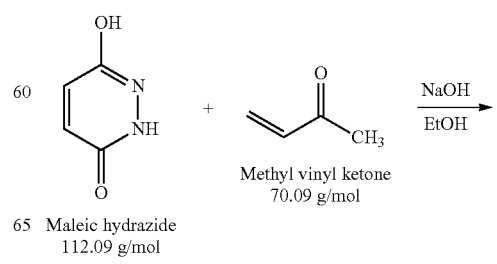

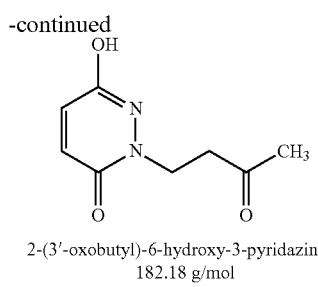

2-(3'-oxobutyl)-6-hydroxy-3-pyridazinone
182.18 g/mol 101 g of maleic hydrazide (0.90 mol, Alfa Aesar), 85 g of methyl vinyl ketone (1.2 mol) and 650 ml of absolute ethanol were combined in a 1-liter flask equipped with a stirbar. 0.5 g of 50% NaOH was added. The flask was immersed in a 100° C. oil bath with a reflux condenser attached. After 7 hours of reaction, as shown in the table below, the homogeneous mixture was poured out into an Erlenmeyer flask and chilled at about 5° C. for about three hours. A heavy white precipitate formed which was recovered by filtration rinsed with methyl-t-butyl ether and dried at 70° C. under 24" Hg (81.3 kPa) vacuum with nitrogen purge overnight. 141 g of product was recovered (86% of theoretical).

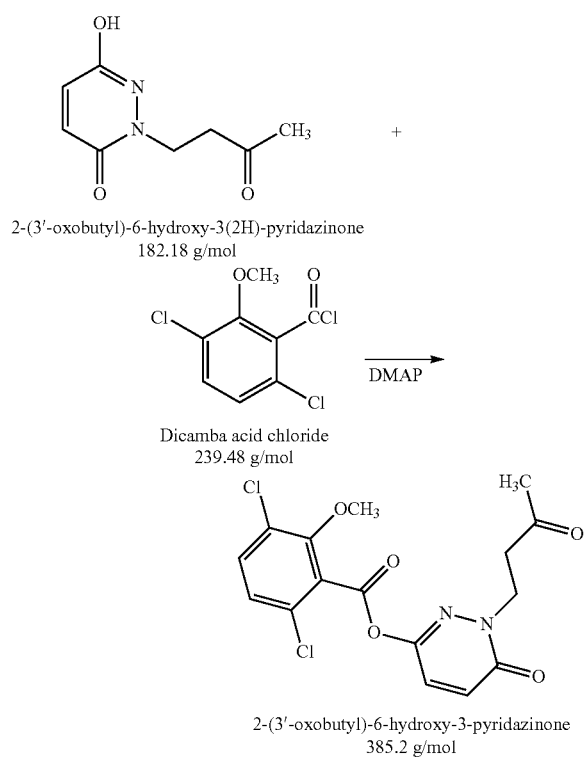

2-(3'-oxobutyl)-6-hydroxy-3(2H)-pyridazinone
182.18 g/mol

Dicamba acid chloride
239.48 g/mol 2-(3'-oxobutyl)-6-hydroxy-3-pyridazinone
385.2 g/mol 170 g of the Michael addition product (0.93 mol) was combined with 94 g of triethylamine (1.0 equiv.), 600 ml of $CH_2Cl_2$, and 235 g of dicamba acid chloride (1.05 equiv) in a 2-liter flask. The mixture boiled and turned yellow within a minute as heavy precipitate formed, freezing the stirbar. It was allowed to stand for 16 hours before a solution of 50 g of $NaHCO_3$ in 600 ml of water was adding, dissolving almost all of the precipitate. The mixture was filtered and the organic layer was isolated and concentrated on a rotary evaporator. 325 g of the product was recovered as a viscous yellow liquid (90% of theoretical).

Example 22: Synthesis of Dicamba Ester 33a Via Michael Addition of Acrolein to Maleic Hydrazide

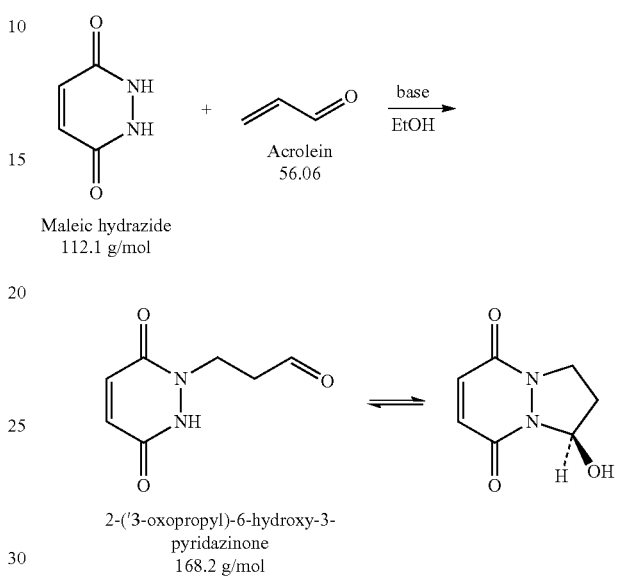

Maleic hydrazide
112.1 g/mol

Acrolein
56.06

2-('3-oxopropyl)-6-hydroxy-3-pyridazinone
168.2 g/mol 39.2 g of maleic hydrazide (0.35 mol, Alfa Aesar), 25.8 g of acrolein (0.46 mol, Aldrich) and 200 ml of absolute ethanol were combined in a 500 ml flask equipped with a stirbar. 0.5 g of 2.5N NaOH was added. The flask was immersed in a 90° C. oil bath with a water-cooled reflux condenser attached. The mixture was refluxed for two hours, at which point a heavy precipitate was seen in the flask. The mixture was allowed to cool and the solid recovered by filtration. The product, a white powder, was rinsed with methyl-t-butyl ether and dried at 80° C. under 24" Hg (81.3 kPa) vacuum with nitrogen purge. 53.7 g were recovered (91% of theoretical). The $^1$H NMR (CDCl$_3$) showed the product to be highly pure and entirely in the hemiaminal form.

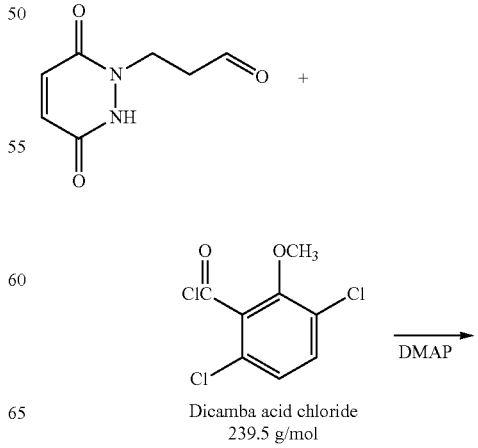

Dicamba acid chloride
239.5 g/mol

-continued

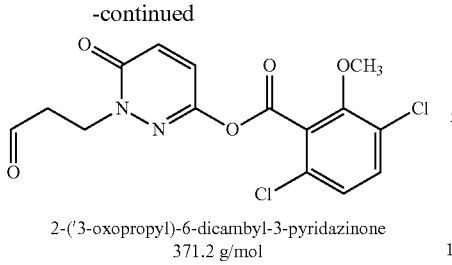

2-('3-oxopropyl)-6-dicambyl-3-pyridazinone
371.2 g/mol 33.6 g of the Michael adduct (0.20 mol) was combined with 0.5 g of DMAP (2 mol %), 20 g of triethylamine (1.0 equiv.) 250 ml of CH$_2$Cl$_2$, and 53 g of dicamba acid chloride (1.1 equiv.). Reaction ensued immediately with the mild boiling and formation of a yellow color. After stirring overnight (16 hours), the mixture was combined with 30 g of NaHCO$_3$ in 400 ml of water and stirred for about 20 minutes. The pale yellow organic layer was isolated and concentrated on a rotary evaporator. A pale yellow, viscous liquid was recovered and placed in an 80° C. vacuum oven for 7 hours under 24" Hg (81.3 kPa) vacuum with nitrogen purge. 81.3 g were recovered (110% of theoretical).

Example 23: Synthesis of Dicamba Ester 34a Via Michael Addition of Acrylonitrile to Maleic Hydrazide

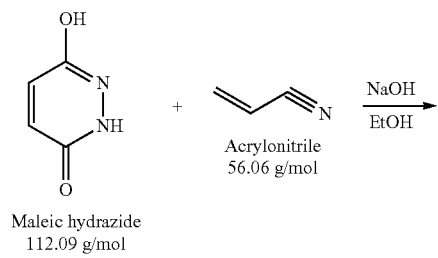

Maleic hydrazide
112.09 g/mol

Acrylonitrile
56.06 g/mol

NaOH / EtOH

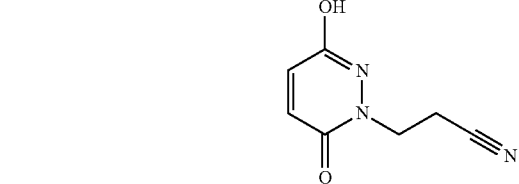

2-(2-cyanoethyl)-6-hydroxy-3(2H)-pyridazinone
165.15 g/mol 44.8 g of maleic hydrazide (0.40 mol, Aldrich), 23.3 g of acrylonitrile (0.44 mol, Aldrich) and 300 ml of absolute ethanol were combined in a 500 ml flask equipped with a stirbar. 8 drops of 2.5N NaOH were added. The flask was immersed in a 100° C. oil bath and a reflux condenser attached. After 14 hours of reaction, the mixture was filtered hot to remove some suspended white solid. Precipitation of a white solid from the filtrate began immediately thereafter. The flask was allowed to stand in a cold room to complete precipitation.

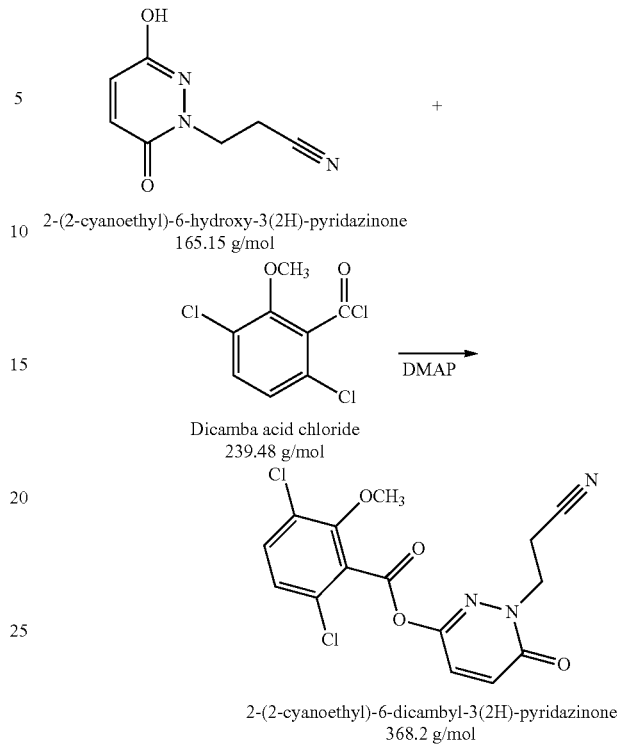

2-(2-cyanoethyl)-6-hydroxy-3(2H)-pyridazinone
165.15 g/mol

Dicamba acid chloride
239.48 g/mol

DMAP 2-(2-cyanoethyl)-6-dicambyl-3(2H)-pyridazinone
368.2 g/mol

The solid was recovered by filtration and dried at 80° C. under 24" Hg (81.3 kPa) vacuum with nitrogen purge. In order to clean up residual water and eliminate the sodium salts, the product was suspended in a mixture of 10 g of acetic acid and 75 ml of water and stirred briefly. The solid was recovered by filtration, rinsed with methyl-t-butyl ether and acetone, and dried at 80° C. under 24" Hg (81.3 kPa) vacuum with nitrogen purge. All of the dry product (7.06 g, 43 mmol) was combined with 4.3 g of triethylamine (1.0 equiv), 0.16 g of DMAP (3 mol %), 100 ml of CH$_2$Cl$_2$, and 11.3 g of dicamba acid chloride (1.1 equiv.) in a roundbottom flask equipped with a stirbar.

After 15 hours of stirring, 6 g of NaHCO$_3$ in 80 ml of water was added to the cloudy solution. A small amount of white solid remained, which was filtered off, and the organic layer was isolated and concentrated on a rotary evaporator. 11.2 g of a viscous, light yellow liquid was recovered, but a good deal of material remained in the flask. Both eventually crystallized and were recovered by filtration and rinsed with CH$_2$Cl$_2$. The off-white powder was dried at 80° C. under 24" Hg (81.3 kPa) vacuum with nitrogen purge.

Example 24: Synthesis of Dicamba Ester 36a

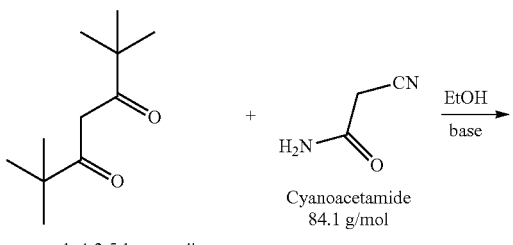

2,2,6,6-tetramethyl-3,5-heptanedione
184.3 g/mol

Cyanoacetamide
84.1 g/mol

EtOH / base

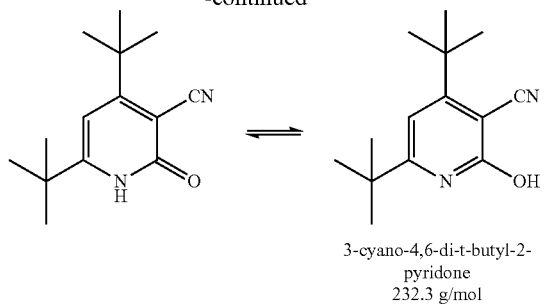

3-cyano-4,6-di-t-butyl-2-pyridone
232.3 g/mol 100 g of 2,2,6,6-tetramethyl-3,5-heptanedione (0.54 mol, Alfa Aesar) was combined with 50 g of cyanoacetamide (1.1 equiv.), 12 g of piperazine (0.25 equiv), and 300 ml of absolute ethanol in a 1-liter roundbottom flask equipped with a stirbar. A reflux condenser was attached and the flask was refluxed in a 90° C. oil bath overnight (15 hours).

The mixture was then added to a solution of 40 g of NaHCO₃ in 600 ml of water in order to protonate the piperazine and extract excess cyanoacetamide. The product separated as a clear upper layer which was isolated. The water layer was rinsed with 200 ml of methyl-t-butyl ether which was isolated and combined with the product. The organic phase was dried over 25 g of MgSO₄, which was then filtered and rinsed with additional methyl-t-butyl ether. The filtrate was concentrated on a rotary evaporator. 130 g was recovered (102% of theoretical).

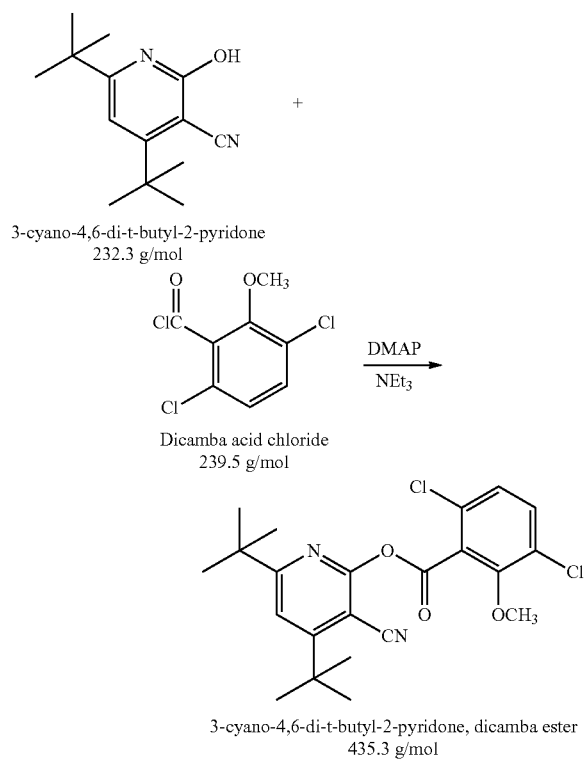

3-cyano-4,6-di-t-butyl-2-pyridone, dicamba ester
435.3 g/mol

All of the product was combined with 55 g of triethylamine (1.0 equiv. if pure), 1.3 g of DMAP (2 mol %), 100 ml of CH₂Cl₂, and 149 g of dicamba acid chloride (1.15 equiv.) and stirred at room temperature for 3 hours. Mild heat evolution was noted and a heavy white precipitate formed within ten minutes. After five hours of reaction, 30 g of NaHCO₃ in 350 ml of water was added. After stirring for a few minutes the organic layer was separated and the solvent removed on a rotary evaporator. 225 g of product was recovered as a dark liquid (95% of theoretical).

Example 25: Synthesis of a Pyridione Diester of Dicamba, 37a

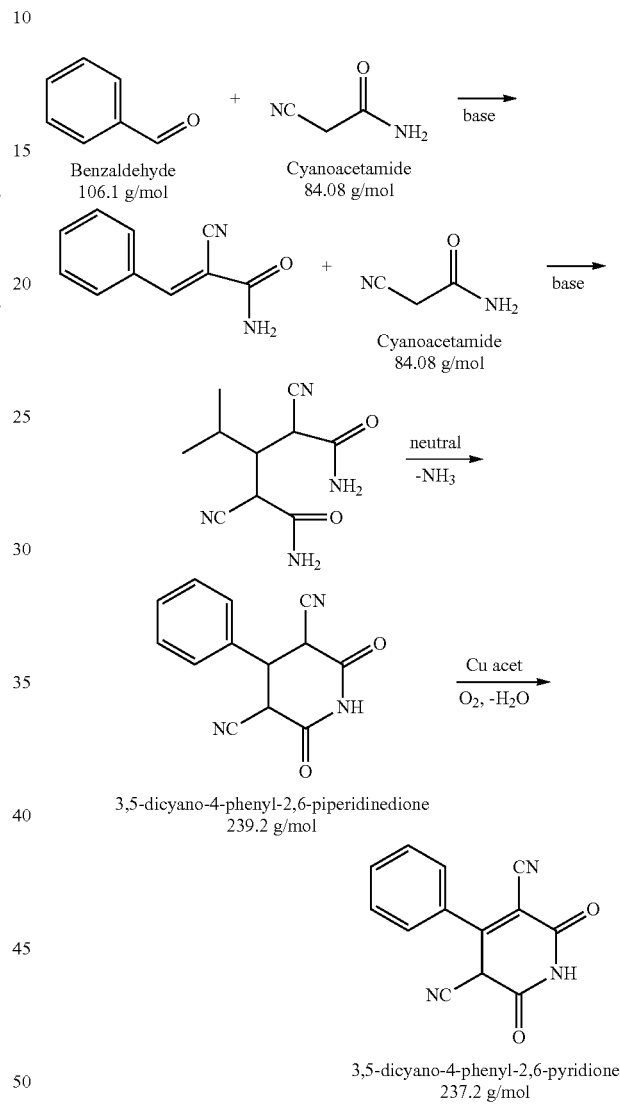

42 g of 2-cyanoacetamide (0.5 mol, Alfa Aesar) and 53 g of benzaldehyde (1.0 equiv., Alfa Aesar) and 1.3 g of 50% NaOH were dissolved in 200 ml of absolute ethanol (enough for complete dissolution at room temperature) in a 3-neck roundbottom flask equipped with a stirbar. A gas dispersion tube was inserted through one side neck, the other side neck was plugged, and a water-cooled reflux condenser was attached to the center neck. The flask was immersed in a 90° C. oil bath and refluxed for 2.5 hours. 50 g of additional cyanoacetamide was then added along with another 100 ml of ethanol. 1 hour after the second cyanoacetamide addition, gentle air bubbling was initiated.

After a further 1.5 hours of reaction (5 hours total), 1.0 g of copper acetate monohydrate (1 mol %) in 5 g of acetic acid were added with a few ml of ethanol used to rinse it into the flask. The acetic acid neutralized the base in order to promote cyclization and to maintain the solubility of the copper. Refluxing was continued for a further 2 hours (7 hours total). The reaction mixture was then poured out into a flask and allowed to cool. The viscous liquid was placed in a vacuum oven at 80° C. under 24" Hg (81.3 kPa) vacuum with nitrogen purge to remove residual ethanol and acetic acid. The resulting material, still highly viscous, was transferred to a jar. 120 g was recovered (101% of theoretical).

Example 26: In Vitro Testing of Dicamba Photo-Release from Photo-Labile Dicamba Esters (Tetrahydrofuran Solvent)

This Example describes in vitro testing of dicamba photo-release by homogeneous solutions of photo-labile dicamba esters. The esters were dissolved in tetrahydrofuran (THF). Ester concentration was 0.1 mM. 25 ml of the solution was transferred to 22 mm tubes fabricated from graded seal

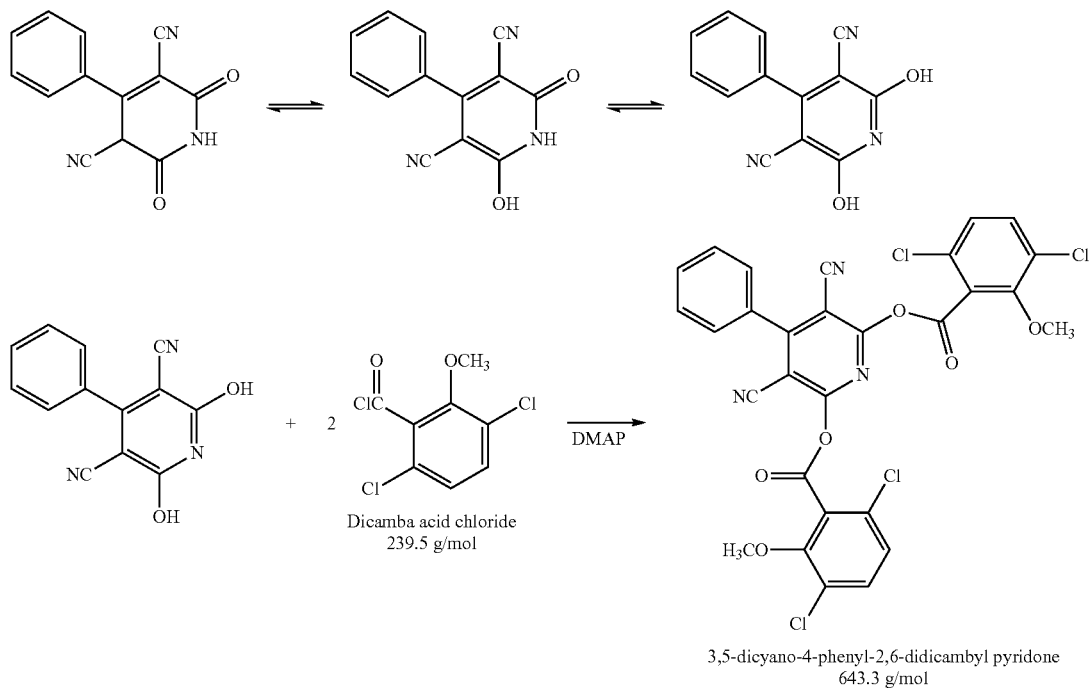

Dicamba acid chloride
239.5 g/mol 3,5-dicyano-4-phenyl-2,6-didicambyl pyridone
643.3 g/mol The product was placed in a 100° C. oven in order to melt it, and 34.7 g (0.15 mol) was transferred to a 1-liter roundbottom flask equipped with a stirbar. 0.5 g of DMAP (3 mol %) was added along with 33 g of triethylamine (2.2 equiv.), 250 ml of $CHCl_3$, and 77 g of dicamba acid chloride (2.2 equiv.). The flask was immersed in a 75° C. oil bath and a water-cooled reflux condenser was attached. The condensation product initially formed a sticky mass in the bottom of the flask but the solution was homogeneous and stirring well with reflux within 20 minutes.

After 4.5 hours of reaction, the mixture was added to a solution of 15 g of $NaHCO_3$ in 300 ml of water. The organic layer was separated, washed with deionized water, and concentrated on a rotary evaporator. 97 g of a dark, viscous liquid was recovered (103% of theoretical). The $^1H$ NMR was consistent with the assigned structure.

quartz tubing with a 19/22 tapered seal at the top, which was closed with a tapered glass plug and secured with a plastic ring clamp. The solution was entirely below the quartz-to-glass transition, ensuring that the entire volume was exposed to the full spectrum.

The sealed tubes were placed in a Growth Chamber where they were exposed to simulated sunlight for 14 hours per day at 35° C. Dicamba concentrations in the solution were measured during the course of the photolysis. As seen below, several esters undergo near-quantitative conversion to dicamba over a period of several days.

The results below, obtained using THF as a solvent, demonstrate high conversion of the photo-labile esters to dicamba. A sample of the initial solution was reserved in a glass vial away from the light source and analyzed at the conclusion of the study, providing a measurement of the amount of dicamba present without illumination of the photolysis solution (the "dark control").

|       |                            | Conversion to dicamba | | | | | | | | |
|-------|----------------------------|-------|--------|--------|--------|--------|--------|---------|---------|---------|
| Ester | Dark Control<br>% dicamba | 1 day | 2 days | 3 days | 5 days | 7 days | 9 days | 11 days | 12 days | 15 days |
| 1a    | 1%                         | 22%   | 33%    | 47%    | 66%    | 76%    |        |         |         |         |
| 2     | 0%                         | 46%   | 54%    | 72%    | 84%    | 88%    | 98%    |         | 96%     | 95%     |
| 9     | 1%                         | 76%   | 91%    | 90%    | 89%    | 89%    |        |         |         |         |

-continued

| | | Conversion to dicamba | | | | | | | | |
|---|---|---|---|---|---|---|---|---|---|---|
| Ester | Dark Control % dicamba | 1 day | 2 days | 3 days | 5 days | 7 days | 9 days | 11 days | 12 days | 15 days |
| 10 | 8% | 16% | 15% | 16% | 19% | 20% | 29% | | 35% | 35% |
| 13a | 11% | 28% | 35% | 43% | 48% | 61% | | 66% | | 68% |

Example 27: In Vitro Testing of Dicamba Photo-Release from Photo-Labile Dicamba Esters (Acetonitrile/10% Water Solvent)

This Example is another photolysis of photo-labile dicamba esters, but using acetonitrile containing 10% water by weight as the solvent. The experimental protocol is otherwise the same as in Example 18.

| | | Conversion to dicamba | | | | | | | |
|---|---|---|---|---|---|---|---|---|---|
| Ester | Dark Control % dicamba | 1 day | 2 days | 3 days | 5 days | 7 days | 11 days | 13 days | 15 days | 19 days |
| 2 | 0% | 33% | 56% | 75% | 93% | 104% | 107% | 108% | 96% | 106% |
| 10 | 8% | 17% | 19% | 20% | 24% | 28% | 32% | 31% | 32% | 33% |
| 14 | 0% | 6% | 9% | 10% | 12% | 12% | 19% | 21% | 25% | 26% |

Example 28: Emulsifiable Concentrate Formulations of Photo-Labile Esters of Dicamba This Example describes formulation of photo-labile esters of dicamba as emulsifiable concentrates. In all cases, the emulsification system was based on a combination of a castor oil ethoxylate, typically SURFONIC CO-54 from Huntsman, and an alkylbenzene sulfonate calcium salt, typically either NANSA EVM/2E, also from Huntsman or WITCONATE P1220EH from Akzo Nobel. Aromatic 200 solvent from Exxon (a complex mixture of aromatic hydrocarbons) was used except in the case of the phenacylmethyl ester whose low solubility made it preferable to use monochlorobenzene, and in the case of 4-n-butoxyphenacymethyl, for which no solvent was used. The formulations and their designations are shown in the table below.

| Ester type | Ester ID | Ester wt % | Solvent† | Surfact. 1‡ | Surfact. 2* |
|---|---|---|---|---|---|
| 2-nitrobenzyl | 1a | 15% | A 200 | P1220, 5% | CO54, 5% |
| 2-nitrophenethyl | 2 | 15% | A 200 | P1220, 5% | CO54, 5% |
| 2-(2-nitrophenoxy)ethanol | 3 | 61% | A 200 | P1220, 5% | CO54, 5% |
| 2-(2-nitrobenzoxy)ethanol | 4 | 63% | A 200 | P1220, 5% | CO54, 5% |
| 4-methoxyphenacymethyl | 9 | 10% | MCB | P1220, 5% | CO54, 5% |
| 4-n-butoxyphenacymethyl | 10 | 90% | None | P1220, 5% | CO54, 5% |
| 2-quinoxalinol | 13a | 17% | A 200 | P1220, 5% | CO54, 5% |

†A200 = Aromatic 200, MCB = monochlorobenzene
‡P1220 = WITCONATE P-1220 EH
*CO54 = SURFONIC CO-54

Example 29: Efficacy of Photo-Labile Ester Formulations for Post-Emergent Control of Velvetleaf The efficacy of some photo-labile ester formulations from Example 28 for post-emergent control of velvetleaf was tested in the greenhouse. All formulations were tested at rates of 140, 280, 420, and 560 g dicamba equivalent per hectare rates and compared to the diglycolamine salt of dicamba (CLARITY®) at the same rates and untreated control plants. The velvetleaf plants were 10-15 cm in height at the time of spraying. Percent control was evaluated three weeks after treatment. The underperformance of the 4-methoxy and 4-n-butoxyphenacyl esters in these data was likely due to screening of ultraviolet light in the greenhouse. Other esters were competitive with conventional salts of dicamba.

| | | % Control of velvetleaf | | | |
|---|---|---|---|---|---|
| Ester type | Ester ID | 140 g/ha | 280 g/ha | 420 g/ha | 560 g/ha |
| Diglycolamine salt | — | 44% | 63% | 68% | 83% |
| 2-nitrobenzyl | 1a | 46% | 60% | 75% | 73% |
| 2-nitrophenethyl | 2 | 50% | 69% | 78% | 90% |
| 4-methoxyphenacymethyl | 9 | 23% | 19% | 28% | 29% |
| 4-n-butoxyphenacymethyl | 10 | 23% | 33% | 28% | 33% |

Example 30: Efficacy of Photo-Labile Ester Formulations for Post-Emergent Control of Velvetleaf The methodology of Example 29 was used to evaluate the efficacy of several photo-labile esters of dicamba for post-emergent control of velvetleaf as emulsifiable concentrate formulations described in Example 28.

| | | % Control of velvetleaf | | | |
|---|---|---|---|---|---|
| Ester type | Ester ID | 140 g/ha | 280 g/ha | 420 g/ha | 560 g/ha |
| Diglycolamine salt | — | 54% | 86% | 96% | 96% |
| 2-(2-nitrophenoxy)ethanol | 3 | 36% | 57% | 40% | 43% |
| 2-(2-nitrobenzoxy)ethanol | 4 | 32% | 52% | 50% | 51% |
| 2-quinoxalinol | 13a | 44% | 69% | 70% | 83% |

Example 31: Emulsifiable Concentrate Formulations of Photo-Labile Dicamba Esters Reduce Volatility Injury to Dicamba-Sensitive Plants This Example demonstrates that emulsifiable concentrate formulations of photo-labile dicamba esters reduce volatility injury to dicamba-sensitive plants compared to the use of dicamba salts under conditions which closely mimic field application. In this case, the diglycolamine salt of dicamba (CLARITY®) was used for comparison.

Dicamba photo-labile ester formulations from Example 28 were mixed with a commercial glyphosate formulation (ROUNDUP POWERMAX®) and diluted to provide a solution with a 0.5% dicamba equivalent concentrate of the ester (or dicamba diglycolamine salt) and 1.5% concentrate of glyphosate. The mixtures were sprayed at a 10 gallon per acre (93.5 liters per hectare) rate on soil in a plastic container ("humidome") with a transparent lid. One soil container was sprayed with water as a control. Four glyphosate-tolerant, dicamba-sensitive soy plants between V2 and V3 stage were immediately placed on the sprayed soil and the domes attached to the trays with binder clips. The soy plants were in pots placed directly on the soil but with aluminum foil wrapped around the bottom to prevent uptake of dicamba or dicamba esters through the roots.

The closed containers were held for 24 hours in a growth chamber which was maintained at 35° C. with 40% relative humidity. The plants were then removed and grown in a greenhouse for three weeks. At this time plant injury and growth stage were assessed compared to the control treated with water only.

Data from this experiment are given below. The use of photo-labile esters largely prevents the retardation of plant development as determined by growth stage while reducing plant injury compared to dicamba salt formulations.

| Ester type | Ester ID | % Injury | Growth Stage |
| --- | --- | --- | --- |
| Diglycolamine salt | — | 38% | 6 |
| 2-nitrobenzyl | 1a | 8% | 8 |
| 2-nitrophenethyl | 2 | 13% | 9 |
| 2-quinoxalinol | 13a | 18% | 8 |
| Untreated | — | 0% | 9 |

Example 32: An Emulsifiable Concentrate Formulation of Dicamba Ester 32a Reduces Volatility Injury to Dicamba-Sensitive Plants The method of Example 31 was used to assess the utility of ester 32a for reducing volatility injury compared to an aqueous dicamba salt solution, except that the dicamba and glyphosate acid equivalents were 0.6% and 1.2% respectively, corresponding to application rates of 0.5 and 1.0 lb/ac (0.56 and 1.12 kg/hectare). Ester 32a was formulated as an emulsifiable concentrate with 30% dicamba acid equivalent as shown below.

| | |
| --- | --- |
| Ester 32a | 52.3% |
| Aromatic 200 (A 200) | 42.7% |
| NINATE 401-A* | 3.5% |
| STEPANTEX CO-40† | 1.5% |

*Alkylbenzene sulfonate (Stepan)
†Castor oil ethoxylate (Stepan)

The average injury to soybeans 14 days after treatment was 19% for dicamba ester 32a versus 60% for the dicamba diglycolamine salt.

Example 33: Suspension Concentrate Formulations of Photo-Labile Esters of Dicamba This Example shows how three dicamba esters of the present invention, 1a, 9, and 13a, can be formulated as suspension concentrates which undergo photo-release of dicamba over a period of several weeks when exposed to sunlight. 1a and 13a underwent preliminary dry milling prior to dispersion, but this was unnecessary for 9. The esters were initially dispersed in a solution containing the dispersing agents, antifoam, and antifreeze using a high shear mixer (Cowles dissolver). Size reduction was then conducted using a horizontal bead mill with ceramic beads. The xanthan gum thickener (KELZAN) was then added as a 1% solution in water.

All formulations contained 0.07% of a silicone antifoam (MAZU DF 100S) and 0.05% of a xanthan gum thickener (KELZAN). The loading of dicamba ester was 35% (wt/wt) in all cases. The other components of the formulations are given in the table below. Water made up the balance of the formulation.

| Ester ID | Mean particle size | Dispersant 1 | Dispersant 2 | Antifreeze |
| --- | --- | --- | --- | --- |
| 1a | 3 μm | MORWET D425, 2.6% | AGRILAN 755, 1.6% | PG, 6.5% |
| 9 | 8 μm | SOKALAN CP-9, 2.1% | INVALON, 5.8% | Glycerin, 11.9% |
| 13a | 3 μm | PLURIOL ES8898, 2.6% | EMULSON AG/TP1 3.3% | PG, 6.5% |

Notes:
PG = propylene glycol. AGRILAN 755 (Akzo Nobel), SOKALAN CP-9 (BASF), PLURIOL ES8898 (BASF) and EMULSON AG/TP1 (Lamberti) are polymeric dispersants. MORWET D-425 (Akzo Nobel) and INVALON are sulfonated naphthalene-formaldehyde condensates.

Example 34: Efficacy of a Photolabile Ester of Dicamba in Reducing Dicamba Volatility Under Realistic Agronomic Conditions This Example illustrates the efficacy of photolabile in reducing the volatility of dicamba under realistic agronomic conditions. An emulsifiable concentrate of the 2-nitrobenzyl ester of dicamba, 1a, was prepared using the Akzo Nobel surfactants SPONTO 334 and 336 along with a castor oil ethoxylated, SURFONIC CO-54, from Huntsman in Aromatic 200 solvent. The composition is given below. The dicamba acid equivalent concentration is 8.84%.

| Component | Weight % |
| --- | --- |
| 2-nitrobenzyl dicamba ester, 1a | 14.25% |
| Aromatic 200 | 80.75% |
| SPONTO EC 334 | 2.25% |
| SPONTO EC 336 | 2.25% |
| SURFONIC CO-54 | 0.50% |

The emulsifiable concentrate of 1a was combined with a commercial glyphosate formulation, ROUNDUP WEATHERMAX®, and sprayed on a test plot at a spray rate of 10 gallons per acre (9.35 liters per hectare). The glyphosate and dicamba rates were 1.0 and 0.5 lb/acre (1.12 and 0.56 kg/hectare) respectively on an acid equivalent basis. The test plot area was approximately 0.05 acre (0.02 hectare) planted with soybeans that were then shortly before flowering. As a comparison, a mixture of the diglycolamine salt of dicamba (CLARITY®) and ROUNDUP WEATHERMAX was sprayed at the same rates.

Immediately after spraying, five air samplers were placed in the four corners and the center of the plots. Airborne dicamba was collected on a polyurethane foam (PUF) trap over the ensuing 24 hours and quantified. The maximum temperature during this period was 86° F. The average dicamba level from the five samplers was 1.2 nanograms per cubic meter of air ($ng/m^3$) compared to 11.1 $ng/m^3$ for the diglycolamine dicamba salt control formulation.

Example 35: In Vitro Testing of Dicamba Photo-Release and Hydrolytic Release from Dicamba Esters in an Aqueous Medium This Example describes the determination of photo-lability and hydrolytic lability of dicamba esters in an aqueous medium. 1 mM solutions of the esters were prepared in acetonitrile (or 0.05 mM solutions of dicamba diesters). The solutions were then diluted with deionized water to a concentration of 0.01 mM (or 0.005 mM for diesters). The solutions were then transferred to quartz tubes and amber bottles and held in a growth chamber by the procedure of Example 26. A 14-hour day was generally used at a constant temperature of 35° C. Hydrolytic activity was assessed by measuring the increase in dicamba concentration after day zero in the amber (dark) bottles. In some cases, due to chromatographic conditions, some dicamba was seen at time zero, but this was an artifact. Photolysis manifested itself as increased conversion in the quartz tubes compared to the dark control. The results of this testing, presented in the table below, show that these dicamba esters convert to dicamba partially or completely by a photochemical mechanism.

| Ester | | Conversion to dicamba | | | | | | | | | | |
|---|---|---|---|---|---|---|---|---|---|---|---|---|
| | | Day 0 | Day 1 | Day 2 | Day 3 | Day 4 | Day 7 | Day 10 | Day 11 | Day 14 | Day 21 | Day 28 |
| 1a | Light | 7% | 13% | 16% | 8% | 21% | 29% | 37% | — | 54% | 75% | 107% |
| | Dark | 7% | 8% | 8% | 8% | 7% | 8% | 8% | — | 8% | 8% | 8% |
| 2 | Light | 3% | 78% | 79% | 75% | 77% | 78% | 84% | — | 82% | 83% | 86% |
| | Dark | 3% | 3% | 3% | 3% | 3% | 3% | 3% | — | 3% | 3% | 3% |
| 13a | Light | 8% | 9% | 12% | 13% | 13% | 15% | — | 19% | 20% | — | — |
| | Dark | 8% | 7% | 7% | 8% | 8% | 9% | — | 11% | 12% | — | — |
| 30a | Light | 6% | — | — | 14% | — | — | — | — | 23% | 29% | 36% |
| | Dark | 6% | — | — | 5% | — | — | — | — | 17% | 17% | 19% |
| 32a | Light | 5% | 14% | 16% | 18% | 22% | 27% | — | — | 44% | 50% | 59% |
| | Dark | 5% | 12% | 14% | 17% | 22% | 34% | — | — | 41% | 55% | 70% |

Example 36: In Vitro Testing of Dicamba Photo-Release and Hydrolytic Release from Dicamba Esters in an Aqueous Medium This Example provides the results of an aqueous lability test following the protocol of Example 35 for several dicamba esters which convert to dicamba primarily by hydrolysis. As shown by the results in the table below, conversion of the dark controls generally equaled or exceeded conversion in the photolysis solutions.

| Ester | | Conversion to Dicamba | | | | | | | | | |
|---|---|---|---|---|---|---|---|---|---|---|---|
| | | Day 0 | Day 1 | Day 2 | Day 3 | Day 4 | Day 7 | Day 10 | Day 14 | Day 21 | Day 28 |
| 14 | Light | 2% | 61% | 63% | 64% | 68% | 67% | — | 71% | 71% | 75% |
| | Dark | 2% | 68% | 81% | 84% | 86% | 92% | — | 90% | 91% | 97% |
| 17 | Light | 6% | 18% | 26% | 33% | 36% | 42% | — | 53% | — | — |
| | Dark | 6% | 16% | 26% | 35% | 41% | 49% | — | 60% | — | — |
| 29a | Light | 27% | 75% | 74% | 75% | 74% | 76% | — | 77% | — | — |
| | Dark | 27% | 81% | 83% | 83% | 80% | 84% | — | 85% | — | — |
| 31a | Light | 16% | 45% | 48% | 46% | 45% | 46% | 50% | 51% | 53% | 53% |
| | Dark | 16% | 37% | 43% | 43% | 44% | 49% | 50% | 51% | 49% | 50% |
| 33a | Light | 13% | 18% | 20% | 19% | 22% | 23% | 30% | 42% | 53% | 57% |
| | Dark | 13% | 15% | 18% | 18% | 22% | 21% | 28% | 37% | 50% | 55% |
| 34a | Light | 3% | 10% | 14% | 16% | 20% | 29% | — | 48% | 60% | 71% |
| | Dark | 3% | 9% | 14% | 18% | 23% | 38% | — | 56% | 71% | 87% |
| 35a | Light | 19% | 57% | 58% | 58% | 62% | 60% | — | 64% | 63% | 65% |
| | Dark | 19% | 66% | 69% | 68% | 71% | 74% | — | 70% | 70% | 74% |
| 36a | Light | 20% | 57% | 60% | 58% | 59% | 63% | — | — | 65% | — |
| | Dark | 20% | 59% | 61% | 60% | 60% | 65% | — | — | 66% | — |

Example 37: Efficacy of Photo-Labile Ester Formulations for Post-Emergent Control of Velvetleaf The methodology of Example 29 was used to evaluate the efficacy of several esters of dicamba which convert to dicamba by hydrolysis for post-emergent control of velvetleaf as emulsifiable concentrate formulations The efficacy of esters which undergo rapid hydrolysis (such as 14, 29a, and 35a) is similar to that of the glycolamine salt, but slower hydrolyzing esters such as (32a and 33a) exhibit reduced post-emergent efficacy.

|  | % Control of velvetleaf | | | |
|---|---|---|---|---|
| Ester ID | 140 g/ha | 280 g/ha | 420 g/ha | 560 g/ha |
| Diglycolamine salt | 43.3% | 65.8% | 87.5% | 90.0% |
| 14 | 40.0% | 58.3% | 80.8% | 85.0% |
| 17 | 23.3% | 41.7% | 75.0% | 73.3% |
| 29a | 30.0% | 55.0% | 74.2% | 81.7% |
| 30a | 19.2% | 12.5% | 18.3% | 15.0% |
| 32a | 12.5% | 19.2% | 33.3% | 37.5% |
| 33a | 15.8% | 27.5% | 22.5% | 30.8% |
| 35a | 35.8% | 60.0% | 85.0% | 87.5% |
| 36a | 15.8% | 26.7% | 32.5% | 66.7% |

Example 38: Field Testing of Emulsifiable Concentrate Formulations of Dicamba Esters 1a, 2, 9, and 13a Four dicamba esters, 1a, 2, 9, and 13a, were formulated as emulsifiable concentrates for field testing. All formulations contained 5% each of a alkylbenzene sulfonate calcium salt (Huntsman NANSA EVM 62/H or Akzo Nobel WITCONATE P-1220 EH) and castor oil ethoxylate (Huntsman SURFONIC CO-54) as the emulsifiers and Aromatic 200 (Exxon) or monochlorobenzene (MCB) as the solvent. The formulations are given in the table below.

| Ester | Ester wt. % | Solvent† | Surfactants‡ | Dicamba ae* |
|---|---|---|---|---|
| 1a | 11.9% | A 200, 78% | P1220/CO54 | 7.4% |
| 2 | 20.6% | A 200, 69% | P1220/CO54 | 12.3% |
| 9 | 9.9% | MCB, 80% | EVM62H/CO54 | 5.9% |
| 13a | 13.6% | A 200 76% | EVM62H/CO54 | 8.6% |

*Dicamba acid equivalent
†A200 = Aromatic 200, MCB = monochlorobenzene
‡P1220 = WITCONATE P-1220 EH, CO54 = SURFONIC CO-54, EVM62H = NANSA EVM 62/H The esters were compared to the diglycolamine salt of dicamba (CLARITY™) for post-emergent control of three broadleaf weeds: velvetleaf, morning glory, and hemp sesbania. Rates of 280 and 420 g dicamba acid equivalent per hectare were used. Nitrophenyl esters 1a and 2 were equivalent to the dicamba salt for post-emergent control of all three types of weeds. Phenacylmethyl ester 9 and quinoxalinol ester 13a were equivalent to the dicamba salt for post-emergent control of morning glory and hemp sesbania, and were nearly equivalent to the dicamba salt for post-emergent control of velvetleaf. Evaluations were conducted at 11 or 21 days after treatment. Locations and timing were identical for all formulations tested.

| Ester | Velvetleaf | Morning glory | Hemp sesbania |
|---|---|---|---|
| | % control, 280 g/ha | | |
| Dicamba DGA salt | 87 | 100 | 81 |
| 1a | 86 | 100 | 95 |
| 2 | 85 | 94 | 92 |
| 9 | 79 | 98 | 86 |
| 13a | 72 | 100 | 95 |
| | % control, 420 g/ha | | |
| Dicamba DGA salt | 91 | 100 | 88 |
| 1a | 92 | 98 | 98 |
| 2 | 92 | 95 | 97 |
| 9 | 80 | 100 | 93 |
| 13a | 84 | 100 | 98 |

Example 39: Field Testing of Dicamba Esters 1a, 9, 13a, 15, and 17 in the Southern Hemisphere Five dicamba esters (1a, 9, 13a, 14, and 17) were tested in the field for post-emergent activity in the Southern Hemisphere. The primary weeds were *Euphorbia* species. Ester 9 was tested as a suspension concentrate using the formulation of Example 33 The other esters were tested as emulsifiable concentrates having the formulations shown in the table below. Akzo Nobel SPONTO EC 334 and SPONTO EC 336 along with SURFONIC CO-54 and NANSA EVM 70/2E (Huntsman) were used as emulsifiers and Aromatic 200 (A 200; Exxon) was used as the solvent.

| Ester | Ester wt. % | Solvent (A 200) † | Surfactants‡ | Dicamba ae* |
|---|---|---|---|---|
| 1a | 14.3% | 81% | EC334, 2.3% EC336, 2.3% CO54, 0.5% | 8.8% |
| 13a | 17.1% | 78% | EC334, 2.3% EC336, 2.3% CO54, 0.5% | 10.8% |
| 14 | 17.2% | 73% | EVM70/2E, 5%, CO-54, 5% | 12.8% |
| 17 | 18.0% | 72% | EVM70/2E, 5%, CO54, 5% | 15.4% |

*Dicamba acid equivalent
† A200 = Aromatic 200
‡EC334 = SPONTO EC 334; EC336 = SPONTO EC 336; CO54 = SURFONIC CO-54; EVM70/2E = NANSA EVM 70/2E The results of field tests at rates of 0.25 and 0.50 lb dicamba acid equivalent (a.e.) per acre (0.28 and 0.56 kg dicamba a.e. per hectare) are given in the table below. The diglycolamine salt of dicamba (CLARITY™) was used as a comparator.

| Ester | % control, 0.25 lb/ac (0.28 kg/hectare) | % control, 0.50 lb/ac (0.56 kg/hectare) |
|---|---|---|
| DGA salt | 53 | 70 |
| 1a | 72 | 78 |
| 9* | 54 | 62 |
| 13a | 46 | 55 |
| 14 | 47 | 56 |
| 17 | 41 | 53 |

*Suspension concentrate

Example 40: Field Testing of Emulsifiable Concentrate Formulations of Dicamba Esters 30a, 32a, and 36a Three dicamba esters, 30a, 32a, and 36a, were formulated as emulsifiable concentrates for field testing. All surfactants are commercial materials from Stepan. The formulations are given in the table below.

| Ester | Ester wt. % | Solvent† | Surfactants‡ | Dicamba ae* |
|---|---|---|---|---|
| 30a | 50.0% | MCB, 45% | TOXIMUL 8320, 5% | 34% |
| 32a | 52.3% | A 200, 43% | NINATE 401-A, 3.5%, STEPANTEX CO-40, 1.5% | 30% |
| 36a | 68.9% | A 200, 26.1% | NINATE 401-A 2.5%, STEPANTEX CO-40, 2.5% | 35% |

*Dicamba acid equivalent
†A200 = Aromatic 200, MCB = monochlorobenzene
‡TOXIMUL 8320 is a butyl block copolymer, NINATE 401-A is an alkylbenzene sulfonate, and STEPANTEX CO-40 is a castor oil ethoxylate The formulations were tested in the field. Locations and timing were identical for the three esters, but differed slightly for the diglycolamine control. The esters were compared to the diglycolamine salt of dicamba (CLARITY™) for post-emergent control of three broadleaf weeds: velvetleaf, morning glory, and hemp sesbania. Rates of 280 and 560 g dicamba acid equivalent per hectare were used. Ester 36a, which converts rapidly to dicamba by hydrolysis has a post-emergent activity similar to the dicamba salt. Ester 30a, which converts relatively slowly by photolysis is less efficacious. Ester 32a, which exhibits an intermediate conversion rate and ultra-low volatility in the closed humidome assay, has an intermediate activity, as expected.

| Ester | Velvetleaf | Morning glory | Hemp sesbania |
|---|---|---|---|
| % control 19 days after treatment, 280 g/ha | | | |
| Dicamba DGA salt | 78 ± 10 | 89 ± 11 | 89 ± 5 |
| 30a | 56 ± 25 | 79 ± 7 | 50 ± 20 |
| 32a | 59 ± 28 | 70 ± 24 | 76 ± 5 |
| 36a | 72 ± 25 | 83 ± 4 | 82 ± 10 |
| % control 19 days after treatment, 560 g/ha | | | |
| Dicamba DGA salt | 91 ± 7 | 94 ± 12 | 96 ± 2 |
| 30a | 65 ± 25 | 78 ± 10 | 67 ± 13 |
| 32a | 68 ± 26 | 87 ± 10 | 91 ± 8 |
| 36a | 84 ± 26 | 93 ± 5 | 98 ± 2 |

In view of the above, it will be seen that the several objects of the invention are achieved and other advantageous results attained.

As various changes could be made in the above compositions and methods without departing from the scope of the invention, it is intended that all matter contained in the above description and shown in the accompanying figures shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An ester of a carboxylic acid agrochemical comprising a labile protecting group and having the formula (XV):

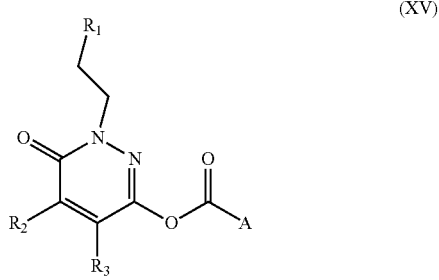

wherein A represents the remainder of the carboxylic acid agrochemical bonded to the carboxylic acid moiety;
$R_1$ is an electron-withdrawing group;
and wherein $R_2$ and $R_3$ are independently H or alkyl.

2. The ester of a carboxylic acid agrochemical of claim 1, wherein the carboxylic acid agrochemical is a herbicide, a fungicide, an insecticide, a plant health agent, or a plant growth regulator.

3. The ester of a carboxylic acid agrochemical of claim 1, wherein the carboxylic acid agrochemical is a herbicide selected from the group consisting of dicamba, 2,4-dichlorophenoxyacetic acid (2,4-D), fenoxaprop, fenoxaprop-P, desmedipham, cyhalofop, carfentrazone, flufenpyr, fluthiacet, fluroglycofen, pyraflufen, flumiclorac, 4-(4-chloro-2-methylphenoxy) butanoic acid (MCPB), fluroxypyr, picloram, quinclorac, benazolin, clodinafop, 4-(2,4-dichlorophenoxy)butanoic acid (2,4-DB), 2,4,5-trichlorophenoxy acetic acid (2,4,5-T), dichlorprop, dichlorprop-P, diethatyl, endothall, fluazifop, flufenpyr, flumiclorac, fluroglycofen, haloxyfop, indole-3-acetic acid, indole-3-butyric acid, mecoprop, mecoprop-P, pyrafluren, fenoprop, triclopyr, aminopyralid, bispyribac, chlorthal, imazamethabenz, pyrothiobac, quinmerac, quizalofop, quizalofop-P, diclofop, and lactofen.

4. The ester of a carboxylic acid agrochemical of claim 1, wherein the carboxylic acid agrochemical is dicamba.

5. The ester of a carboxylic acid agrochemical of claim 1 wherein the carboxylic acid agrochemical is 2,4-dichlorophenoxyacetic acid (2,4-D).

6. The ester of a carboxylic acid agrochemical of claim 1, wherein the carboxylic acid agrochemical is:
  a fungicide selected from the group consisting of benalaxyl and picoxystrobin;
  a plant health agent selected from the group consisting of salicylic acid and 3,6-dichlorosalicylic acid; or
  a plant growth regulator selected from the group consisting of cloprop and 4-chlorophenoxyacetic acid (4-CPA).

7. The ester of a carboxylic acid agrochemical of claim 1, wherein the electron-withdrawing group is selected from nitriles, ketones, aldehydes, esters, carboxylates, and nitro.

8. The ester of a carboxylic acid agrochemical of claim 1, wherein:
  $R_2$ and $R_3$ are both H; or
  one or both of $R_2$ and $R_3$ is alkyl.

9. The ester of a carboxylic acid agrochemical of claim 8, wherein one or both of $R_2$ and $R_3$ is $C_1$-$C_{18}$ alkyl.

10. The ester of a carboxylic acid agrochemical of claim 1, wherein $R_1$ is selected from the group consisting of —COCH$_3$, —CHO, —CN, and, —COOCH$_2$CH$_3$.

11. The ester of a carboxylic acid agrochemical of claim 1, wherein:
R$_1$ is —COCH$_3$ and R$_2$ and R$_3$ are both H;
R$_1$ is —CHO and R$_2$ and R$_3$ are both H;
R$_1$ is —CN and R$_2$ and R$_3$ are both H; or
R$_1$ is —COOCH$_2$CH$_3$ and R$_2$ and R$_3$ are both H.

12. The ester of a carboxylic acid agrochemical of claim 1, wherein the carboxylic acid agrochemical is dicamba or 2,4-dichlorophenoxyacetic acid (2,4-D) and the ester is selected from the group consisting of:

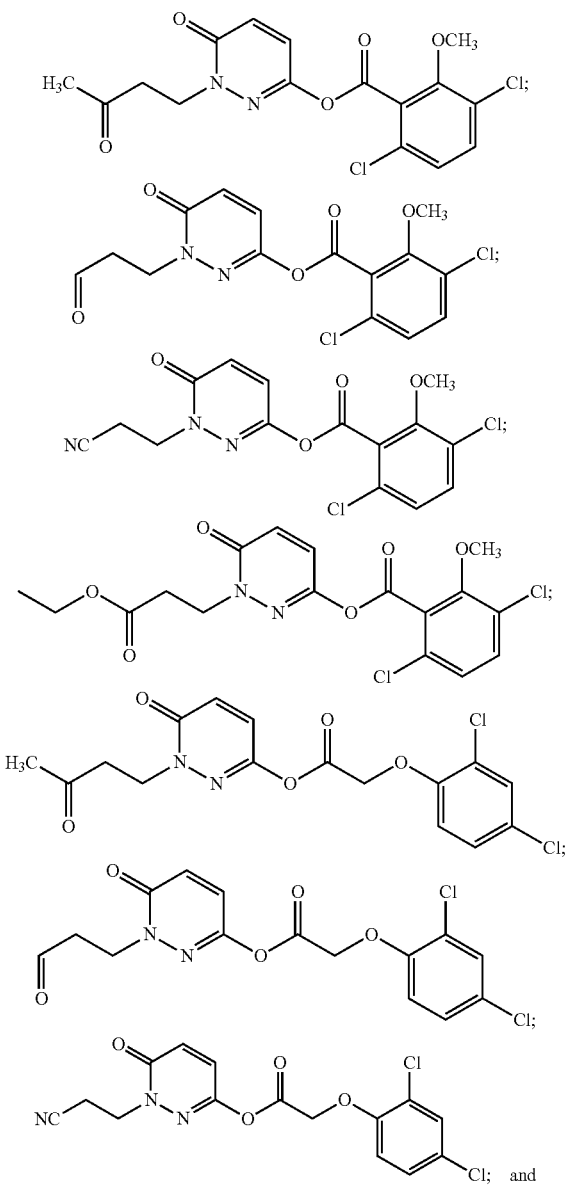

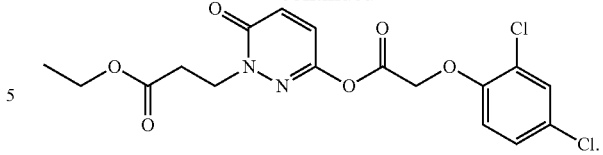

13. A composition comprising an ester of a carboxylic acid agrochemical of claim 1.

14. The composition of claim 13, which is in the form of an emulsifiable concentrate or suspension concentrate.

15. The composition of claim 13, further comprising one or more adjuvants selected from the group consisting of solvents, surfactants, dispersants, antifreeze agents, antifoam agents, thickeners, bacteriostats, wetting agents, dyes, and combinations or mixtures thereof.

16. The composition of claim 13, wherein:
the solvent comprises an aromatic hydrocarbon, monochlorobenzene, a naphthalenic organic solvent, isophorone, a carboxylic acid ester, a carboxylic acid diester, a pyrrolidone, or a combination or mixture thereof;
the surfactant comprises a mixture of a nonionic surfactant and an anionic surfactant;
the surfactant comprises an ethoxylated alkyl alcohol, an ethoxylated vegetable oil, a sulfonate, or a combination or mixture thereof;
the surfactant comprises ethoxylated castor oil, an alkylbenzene sulfonate calcium salt, or a combination or mixture thereof;
the dispersant comprises a lignosulfonate, a sulfonated naphthalene-formaldehyde condensate, a polymeric dispersant, or a combination or mixture thereof;
the antifreeze agent comprises propylene glycol, glycerin, or a combination or mixture thereof;
the antifoam agent comprises a silicone antifoam agent; and/or
the thickener comprises xanthan gum, a silica, a clay, or a combination or mixture thereof.

17. The composition of claim 13, wherein the carboxylic acid agrochemical is dicamba or 2,4-dichlorophenoxyacetic acid (2,4-D).

18. The composition of claim 13, further comprising a second agrochemical.

19. The composition of claim 18, wherein the second agrochemical is an herbicide.

20. A method for the controlled release of a carboxylic acid agrochemical comprising exposing an ester of a carboxylic acid agrochemical of claim 1 to artificial or natural light.

21. A method of controlling unwanted plants comprising applying to the unwanted plants an ester of a carboxylic acid agrochemical of claim 1.

* * * * *